US010745722B2

(12) United States Patent
Nomura et al.

(10) Patent No.: US 10,745,722 B2
(45) Date of Patent: *Aug. 18, 2020

(54) ENGINEERED STRAIN OF *ESCHERICHIA COLI* FOR PRODUCTION OF POLY-R-3-HYDROXYALKANOATE POLYMERS WITH DEFINED MONOMER UNIT COMPOSITION AND METHODS BASED THEREON

(71) Applicant: THE RESEARCH FOUNDATION FOR THE STATE UNIVERSITY OF NEW YORK, Albany, NY (US)

(72) Inventors: Christopher T. Nomura, Syracuse, NY (US); Ryan C. Tappel, Syracuse, NY (US); Qin Wang, Syracuse, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 53 days.

This patent is subject to a terminal disclaimer.

(21) Appl. No.: 15/650,265

(22) Filed: Jul. 14, 2017

(65) Prior Publication Data
US 2018/0010156 A1    Jan. 11, 2018

Related U.S. Application Data

(63) Continuation of application No. 14/371,025, filed as application No. PCT/US2013/020875 on Jan. 9, 2013.

(60) Provisional application No. 61/584,495, filed on Jan. 9, 2012.

(51) Int. Cl.
*C12P 7/62* (2006.01)
*C12N 9/88* (2006.01)
*C12N 9/10* (2006.01)

(52) U.S. Cl.
CPC ............. *C12P 7/62* (2013.01); *C12N 9/1029* (2013.01); *C12N 9/88* (2013.01); *C12P 7/625* (2013.01); *C12Y 203/01* (2013.01); *C12Y 402/01017* (2013.01); *C12Y 402/01055* (2013.01)

(58) Field of Classification Search
None
See application file for complete search history.

(56) References Cited

U.S. PATENT DOCUMENTS 7,183,087 B2    2/2007   Lee et al.
2011/0166318 A1   7/2011   Jiang et al.
2014/0349353 A1   11/2014   Nomura et al.

FOREIGN PATENT DOCUMENTS

| WO | WO9854329 | 12/1998 |
|---|---|---|
| WO | WO-9854329 A1 | 12/1998 |
| WO | 2014/096276 | 6/2014 |
| WO | WO-2014/096276 A1 | 6/2014 |

OTHER PUBLICATIONS

Korean Intellectual Property Office—International Search Report and Written Opinion of the International Searching Authority for International Application No. PCT/US2013/020875 dated Apr. 30, 2013 (14 pages).
Sato, Shun et al., "Poly[(R)-3-Hydroxybutyrate] Formation in *Escherichia coli* from Glucose through an Enoyl-CoA Hydratase-Mediated Pathway," 2007 Journal of Bioscience and Bioengineering, vol. 103, No. 1, pp. 38-44.
Kim, Do Young et al., "Biosynthesis, Modification, and Biodegradation of Bacterial Medium-Chain-Length Polyhydroxyalkanoates," 2007 Journal of Microbiology, vol. 45, No. 2, pp. 87-97.
Jenkins Lauren Sallus et al., "Genetic and Molecular Characterization of the Genes Involved in Short-Chain Fatty Acid Degradation in *Escherichia coli*: the ato System," 1987 Journal of Bacteriology, vol. 169, No. 1, pp. 42-52.
Dirusso, Concetta C. et al., "Characterization of FadR, a Global Transcriptional Regulator of Fatty Acid Metabolism in *Escherichia coli*," 1992 Journal of Biological Chemistry, vol. 267, No. 12, pp. 8685-8691.
Nikel, Pablo I. et al., "Poly(3-Hydroxybutyrate) Synthesis by Recombinant *Escherichia coli* arcA Mutants in Microaerobiosis," 2006 Applied and Environmental Microbiology, vol. 72, No. 4, pp. 2614-2620.
Wang, Hong-Hui et al., "Biosynthesis of polyhydroxyalkanoate homopolymers by *Pseudomonas putida*," 2011 App. Microbiol. Biotechnol., vol. 89, pp. 1497-1507.
Liu, Qian et al., "Biosynthesis of poly(3-hydroxydecanoate) and 3-hydroxydodecanoate dominating polyhydroxyalkanoates by β-oxidation pathway inhibited Pseudomonas putida," 2011 Metabolic Engineering, vol. 13, pp. 11-17.
Nomura, Christopher T. et al., "Effective Enhancement of Short-Chain-Length—Medium-Chain-Length Polyhydroxyalkanoate Copolymer Production by Coexpression of Genetically Engineered 3-Ketoacyl-Acyl-Carrier-Protein Synthase III (*fabH*) and Polyhydroxyalkanoate Synthesis Genes," 2004 Biomacromolecules, vol. 5, pp. 1457-1464.

(Continued)

*Primary Examiner* — Suzanne M Noakes
*Assistant Examiner* — Jae W Lee
(74) *Attorney, Agent, or Firm* — Harris Beach PLLC; Laura W. Smalley

(57) ABSTRACT

Methods and systems for producing prescribed unit size poly(3-hydroxyalkanoate) (PHA) polymers and copolymers are provided. The methods and systems can employ recombinant bacteria that are not native producers of PHA or lack enzymes to degrade PHA once synthesized, metabolize short to long chain fatty acids without induction, and express an (R)-specific enoyl-CoA hydratase and a PHA synthase, the (R)-specific enoyl-CoA hydratase and PHA synthase having wide substrate specificities. The recombinant bacteria are fed at least one fatty acid substrate that is equal in carbon length to the prescribed or desired unit size of the PHA polymer to be produced. The prescribed unit size PHA that is produced is then isolated and/or purified.

10 Claims, 35 Drawing Sheets

Specification includes a Sequence Listing.

(56) References Cited

OTHER PUBLICATIONS

Zhu, Chengjun et al., "Production and Characterization of Poly-3-hydroxybutyrate From Biodiesel-Glycerol by *Burkholderia cepacia* ATCC 17759," 2010 Biotechnol. Prog., vol. 26, No. 2, pp. 424-430.
Lu, Jinghan et al., Mini-Review: Biosysthesis of Poly(hydroxyalkanoates), 2009 Journal of Macromolecular Science, Part C: Polymer Reviews, vol. 49, pp. 226-248.
European Patent Office—Extended European Search Report for EP Application No. 13 735 835.4 dated Nov. 2, 2015 (6 pages).
Tappel, Ryan C. et al., "Precise control of repeating unit composition in biodegradable poly(3-hydroxyalkanoate) polymers synthesized by *Escherichia coli*," 2012 Journal of Bioscience and Bioengineering, vol. 113, No. 4 (pp. 480-486).
Tappel, Ryan C. et al., "Biosynthesis of Poly[(R)-3-hydroxyalkanoate] Copolymers with Controlled Repeating Unit Compositions and Physical Properties," 2012 Biomacromolecules, vol. 11 (pp. 2964-2972).
Tappel, Ryan C. et al., "Supporting Information Biosynthesis poly[(R)-3-hydroxyalkanoate] copolymers with controlled repeating unit composition and physical properties," 2012 Biomacromolecules (11 pgs) XP002748130.
Park, Si Jae et al., "Biosynthesis of lactate-containing polyesters by metabolically engineered bacteria," 2012 Biotechnol., vol. 7, No. 2 (pp. 199-212).
Davis, Mark S. et al., "Overproduction of Acetyl-CoA Carbosylase Activity Increases the Rate of Fatty Acid Biosynthesis in *Escherichia coli*" 2000 The Journal of Biological Chemistry, vol. 275, No. 37 (pp. 25893-25898).
Tsuge Takeharu et al., "Molecular characterization and properties of (R)-specific enoyl-CoA hydratases from *Pseudomonas aeruginoa*: metabolic tools for synthesis of polyhydroxyalkanoates via fatty acid β-oxidation," 2003 International Journal of Biological Macromolecules, vol. 31, pp. 195-205.
Sato, Shun et al., "Expression and characterization of (R)-specific enoyl coenzyme A hydratases making a channeling route to polyhydroxyalkanoate biosnythesis in *Pseudomonas putida*," 2011 Appl. Microbiol. Biotechnol., vol. 90, pp. 951-959.
Fukui, Toshiaki et al., "Co-expression of polyhydroxyalkanoate synthase and (R)-enoyl-CoA hydratase genes of *Aeromonas caviae* establishes copolyester biosynthesis pathway in *Escherichia coli*," 1999 FEMS Microbiology Letters 170, pp. 69-75.
Tsuge, Takeharu et al., "Molecular cloning of two (R)-specific enoyl-CoA hydratase genes from *Pseudomonas aeruginosa* and their use for polyhydroxyalkanoate synthesis," 1999 FEMS Microbiology Letters 184, pp. 193-198.
Matsumoto, Ken'ichiro et al., "Synergistic Effects of Glu130Asp Substitution in the Type II Polyhydroxyalkanoate (PHA) Synthase: Enhancement of PHA Production and Alteration of Polymer Molecular Weight," 2005 Biomacromolecules, vol. 6, pp. 99-104.
ISA/US International Search Report and Written Opinion for corresponding International Application No. PCT/US2016/061596, dated Feb. 1, 2017 (pp. 9).
Lemechko, et al., "Synthesis of dextran-graft-PHBHV amphiphilic copolymer using click chemistry approach," Reactive & Functional Polymers, May 8, 2012, vol. 72, No. 8 (pp. 487-494).
Aldor, et al., "Process design for microbial plastic factories: metabolic engineering of polyhydroxyalkanoates," Current Opinion in Biotechnology, Oct. 31, 2003, vol. 14, No. 5 (pp. 475-483).
Rhie, H. and Dennis, D., "Role of fadR and atoC(Con) mutations in poly(3-hydroxybutyrate-Co-3-hydroxyvalerate) synthesis in recombinant pha+ *Escherichia coli*", 1995, Applied and Environmental Microbiology 1995, vol. 61, No. 7 (pp. 2487-2492).
European Office Action for corresponding European Patent Application 13735835.4, dated May 5, 2017 (48 pages).
Decision of the Enlarged Board of Appeal of Nov. 29, 2016 of the European Patent Office (49 pages).
Matsumoto, et al., (Biosynthesis of glycolate-based polyesters containing medium-chain-lenghth 3-hydroxyalkanoates in recombinant *Escherichia coli* expressing engineered polyhydroxyalkanoate synthase, Journal of biotechnology 156 (2011) 214-217, available online Aug. 31, 2011).
Rehm, et al., "Heterologous expression of the acyl-acyl carrier protein thioesterase gene from the plant Umbellularia californica mediates plyhydroxyalkanoate biosynthesis in recombinant *E. coli*", Appl Microbiol Biotechnol (2001) 55:205-209.
Langenbach, et al., "Functional expression of the PHA synthase gene phaC1 from Pseudomonas aeruginosa in *Escherichia coli* results in poly (3-hydroxyalkanoate) synthesis", FEMS Microbiology Letters 150 (1997) 303-309.
Nomura, et al., "FabG mediates Polyhydroxyalkanoate Production from both Related and Nonrelated Carbon Sources in Recombinant *Escherichia coli* LS5218", Biotechnol. Prog. 2008, 24, 342-351.
UniProt "3-hydroxyacyl-CoA dehydrogenase" (retrieved from teh Internet:<http://www.uniprot.org/uniprot/Q88I88>, retrieved on Jul. 18, 2017.
FadJ 3-hydroxyacyl-CoA dehydrogenase (Retrieve from the Internet:ttps://biocyc.org/gene?orgid-ECOLI&id-G7212>, retrieved on Jul. 18, 2017).

```
                        SEQUENCE LISTING

<160> NUMBER OF SEQ ID NOS: 10

<210> SEQ ID NO 1
<211> LENGTH: 70
<212> TYPE: DNA
<213> ORGANISM: Artificial Sequence
<220> FEATURE:
<223> OTHER INFORMATION: Synthesized sequence.

<400> SEQUENCE: 1
atggaaatga catcagcgtt taccettaat gttcgtctgg acaacattgc gtgtaggctg     60
gagctgcttc                                                            70

<210> SEQ ID NO 2
<211> LENGTH: 70
<212> TYPE: DNA
<213> ORGANISM: Artificial Sequence
<220> FEATURE:
<223> OTHER INFORMATION: Synthesized sequence.

<400> SEQUENCE: 2
ttattgcagg tcagttgcag ttgttttcca aaaactttcc ccacgcgcgc attccgggga     60
tccgtcgacc                                                            70

<210> SEQ ID NO 3
<211> LENGTH: 70
<212> TYPE: DNA
<213> ORGANISM: Artificial Sequence
<220> FEATURE:
<223> OTHER INFORMATION: Synthesized sequence.

<400> SEQUENCE: 3
atgctttaca aaggcgacac cctgtacctt gactggctgg aagatggcat gtgtaggctg     60
gagctgcttc                                                            70

<210> SEQ ID NO 4
<211> LENGTH: 70
<212> TYPE: DNA
<213> ORGANISM: Artificial Sequence
<220> FEATURE:
<223> OTHER INFORMATION: Synthesized sequence.

<400> SEQUENCE: 4
```

```
ttaagccgtt ttcaggtcgc caaccggacg ggctggctca accggaggat catatgaata      60
tcctccttag                                                             70
```

<210> SEQ ID NO 5
<211> LENGTH: 20
<212> TYPE: DNA
<213> ORGANISM: Artificial Sequence
<220> FEATURE:
<223> OTHER INFORMATION: Synthesized sequence.

<400> SEQUENCE: 5

```
ggtttagtta ccgcctgtgc                                                  20
```

<210> SEQ ID NO 6
<211> LENGTH: 20
<212> TYPE: DNA
<213> ORGANISM: Artificial Sequence
<220> FEATURE:
<223> OTHER INFORMATION: Synthesized sequence.

<400> SEQUENCE: 6

```
agcgcggatt catatagctt                                                  20
```

<210> SEQ ID NO 7
<211> LENGTH: 20
<212> TYPE: DNA
<213> ORGANISM: Artificial Sequence
<220> FEATURE:
<223> OTHER INFORMATION: Synthesized sequence.

<400> SEQUENCE: 7

```
gcgagtccgt tcttgtaagg                                                  20
```

<210> SEQ ID NO 8
<211> LENGTH: 20
<212> TYPE: DNA
<213> ORGANISM: Artificial Sequence
<220> FEATURE:
<223> OTHER INFORMATION: Synthesized sequence.

<400> SEQUENCE: 8

```
cgaattgcat cgacaatgac                                                  20
```

<210> SEQ ID NO 9
<211> LENGTH: 29
<212> TYPE: DNA
<213> ORGANISM: Artificial Sequence
<220> FEATURE:
<223> OTHER INFORMATION: Synthesized sequence.

<400> SEQUENCE: 9

```
attggtaccc aactgacaac ccggagagt                                        29
```

<210> SEQ ID NO 10
<211> LENGTH: 28
<212> TYPE: DNA
<213> ORGANISM: Artificial Sequence
<220> FEATURE:
<223> OTHER INFORMATION: Synthesized sequence.

<400> SEQUENCE: 10

```
attgatatcc tggcagttta cgcgagtg                                         28
```

ENGINEERED STRAIN OF ESCHERICHIA COLI FOR PRODUCTION OF POLY-R-3-HYDROXYALKANOATE POLYMERS WITH DEFINED MONOMER UNIT COMPOSITION AND METHODS BASED THEREON

CROSS-REFERENCE TO RELATED APPLICATIONS

This application is a continuation of co-pending U.S. patent application Ser. No. 14/371,025, filed Jul. 8, 2014, entitled Engineered Strain of *Escherichia coli* for Production of Poly-R-3-Hydroxyalkanoate Polymers with Defined Monomer Unit Composition and Methods Based Thereon, which is a national stage application under 35 U.S.C. § 371 of PCT Application No. PCT/US2013/020875, which claims priority to and the benefit of U.S. provisional patent application Ser. No. 61/584,495, entitled "Engineered Strain of *Escherichia coli* for Production of R-3-Hydroxyalkanoic Acids and Poly-R-3-Hydroxyalkanoate Polymers with Defined Monomer Unit Composition," filed Jan. 9, 2012, which is incorporated herein by reference in its entirety.

STATEMENT REGARDING FEDERALLY SPONSORED RESEARCH OR DEVELOPMENT

This invention was made with government support under grant DMR0907085 awarded by the National Science Foundation. The government has certain rights in the invention.

1. TECHNICAL FIELD

The present invention relates to biodegradable poly(3-hydroxyalkanoate) polymers and copolymer and methods for synthesizing biodegradable poly(3-hydroxyalkanoate) polymers and copolymers.

2. BACKGROUND OF THE INVENTION

Poly(3-hydroxyalkanoates) (PHAs) are biodegradable plastics and carbon storage materials that are synthesized by a myriad of microorganisms. PHAs are divided into groups based on repeating unit size. PHAs with repeating units of three to five carbons in length are short-chain-length (SCL) PHAs, and PHAs with repeating units of six to fourteen carbons in length are medium-chain-length (MCL) PHAs. Differences in repeating unit composition influence the physical properties of PHAs. SCL PHA homopolymers such as poly-3-hydroxybutyrate (PHB) have been previously produced, but methods to control the repeating unit composition of the MCL PHAs have been limited. Previous attempts to control MCL PHA synthesis in native and recombinant PHA-producing organisms have resulted in narrow ranges of repeating unit control. Typically, control is limited to only a couple of repeating units within one organism or control is lost once the number of carbons in the repeating unit exceeds seven Thus, the composition of medium-chain-length (MCL) poly(3-hydroxyalkanoate) (PHA) biopolymers is normally an uncontrollable random mixture of repeating units with differing side chain lengths. Attempts to generate MCL PHA homopolymers and gain control of the repeating unit composition have been reported for native or natural PHA-producing organisms but have limited ranges for the different sizes of repeating units that can be synthesized.

Citation or identification of any reference in Section 2, or in any other section of this application, shall not be considered an admission that such reference is available as prior art to the present invention.

3. SUMMARY OF THE INVENTION

A method is provided for producing a prescribed unit size poly(3-hydroxyalkanoate) (PHA) polymer comprising the steps of:
providing a recombinant bacterium, wherein the bacterium:
metabolizes short to long chain fatty acids without induction, and expresses an (R)-specific enoyl-CoA hydratase and a PHA synthase;
feeding at least one fatty acid substrate to the recombinant bacterium, the at least one fatty acid substrate being of equal carbon length to the prescribed unit size of the PHA polymer to be produced; and
isolating and/or purifying the PHA from the recombinant bacterium, thereby producing the PHA polymer.

A prescribed unit size refers to the desired number of carbon atoms that are in the unit.

In one embodiment of the method, the (R)-specific enoyl-CoA hydratase and PHA synthase have wide substrate specificities.

In another embodiment of the method, the PHA polymer is a PHA homopolymer, a PHA copolymer or a PHA-co-polylactic acid (PLA) polymer.

In another embodiment of the method, at least one lactic acid substrate is co-fed to the bacterium and a PHA-co-PLA polymer is produced.

In another embodiment of the method, the recombinant bacterium is a recombinant *E. coli*.

In another embodiment of the method, the step of providing a recombinant bacterium comprises the step of constructing a plasmid comprising an (R)-specific enoyl-CoA hydratase gene and a PHA synthase gene and transforming the plasmid into the recombinant bacterium.

In another embodiment of the method, the recombinant bacterium is a recombinant *E. coli* and the plasmid is pBBR-C1J4SII.

In another embodiment of the method, β-oxidation is blocked in the recombinant bacterium, thereby causing a buildup of enoyl-CoA intermediates.

In another embodiment of the method, at least one gene encoding an enzyme for β-oxidation is inactive or deleted from the chromosome of the recombinant bacterium.

In another embodiment of the method, the at least one gene encoding an enzyme for β-oxidation is a gene encoding an (S)-specific enoyl-CoA hydratase.

In another embodiment of the method, the at least one gene encoding an enzyme for β-oxidation is a fad gene.

In another embodiment of the method, the recombinant bacterium is recombinant *E. coli* and an (S)-specific enoyl-CoA hydratase fadB gene and/or a fadJ gene is deleted from the chromosome of the recombinant *E. coli*.

In another embodiment of the method, the recombinant bacterium constitutively expresses a positive regulator of an operon, wherein the operon promotes uptake of short chain fatty acids for β-oxidation.

In another embodiment of the method, the recombinant bacterium is a recombinant *E. coli* and wherein the recombinant *E. coli* constitutively expresses a positive regulator of the ato operon, thereby promoting uptake of short chain fatty acids for β-oxidation.

In another embodiment of the method, the recombinant *E. coli* constitutively expresses AtoC.

In another embodiment of the method, the recombinant bacterium is a recombinant *E. coli*, the (R)-specific enoyl-CoA hydratase is PhaJ4 and the PHA synthase is PhaC1 (STQK).

In another embodiment of the method, the recombinant bacterium expresses propionyl-CoA transferase (PCT).

In another embodiment of the method, the recombinant bacterium has gene deletions for a negative transcriptional regulator of the β-oxidation pathway.

In another embodiment of the method, the negative transcriptional regulator is arcA or ompR.

In another embodiment of the method, the recombinant bacterium has gene deletions for arcA and ompR.

In another embodiment of the method, at least two different types of fatty acid substrates of desired length are fed to the recombinant bacteria in a desired ratio, thereby producing a PHA polymer, PHA copolymer or PHA-co-PLA polymer of desired (or controlled) repeating unit composition.

A method for producing the recombinant bacterium is also provided, wherein the bacterium:
  metabolizes short to long chain fatty acids without induction, and
  expresses an (R)-specific enoyl-CoA hydratase and a PHA synthase.

In one embodiment of the method, the recombinant bacterium is not a native or natural producer of PHA or lacks enzymes to degrade PHA once synthesized.

In another embodiment the method, the (R)-specific enoyl-CoA hydratase and PHA synthase have wide substrate specificities.

A system is provided for producing a prescribed unit size poly(3-hydroxyalkanoate) (PHA) polymer comprising a recombinant (genetically engineered) bacterium, wherein the bacterium:
  metabolizes short to long chain fatty acids without induction, and
  expresses an (R)-specific enoyl-CoA hydratase and a PHA synthase.

A prescribed unit size refers to the desired number of carbon atoms that are in the unit.

In one embodiment of the system, the PHA polymer is a PHA homopolymers, a PHA copolymer or a PHA-co-PLA polymer.

In another embodiment of the system, the (R)-specific enoyl-CoA hydratase and PHA synthase have wide substrate specificities.

In another embodiment of the system, the recombinant bacterium is a recombinant *E. coli*.

In another embodiment of the system, the recombinant bacterium comprises a plasmid comprising an (R)-specific enoyl-CoA hydratase gene and a PHA synthase gene.

In another embodiment of the system, the recombinant bacterium is a recombinant *E. coli* and the plasmid is pBBR-C1J4SII.

In another embodiment of the system, β-oxidation is blocked in the recombinant bacterium, thereby causing a buildup of enoyl-CoA intermediates.

In another embodiment of the system, at least one gene encoding an enzyme for β-oxidation is inactive or deleted from the chromosome of the recombinant bacterium.

In another embodiment of the system, the at least one gene encoding an enzyme for β-oxidation is a gene encoding an (S)-specific enoyl-CoA hydratase.

In another embodiment of the system, the at least one gene encoding the enzymes for β-oxidation is a fad gene.

In another embodiment of the system, the recombinant bacterium is recombinant *E. coli* and an (S)-specific enoyl-CoA hydratase fadB gene and/or a fadJ gene is deleted from the chromosome of the recombinant *E. coli*.

In another embodiment of the system, the recombinant bacterium constitutively expresses a positive regulator of an operon, wherein the operon promotes uptake of short chain fatty acids for β-oxidation.

In another embodiment of the system, the recombinant bacterium is a recombinant *E. coli* and wherein the recombinant *E. coli* constitutively expresses a positive regulator of the ato operon, thereby promoting uptake of short chain fatty acids for β-oxidation.

In another embodiment of the system, the recombinant *E. coli* constitutively expresses AtoC.

In another embodiment of the system, the recombinant bacterium is a recombinant *E. coli*, the (R)-specific enoyl-CoA hydratase is PhaJ4 and the PHA synthase is PhaC1 (STQK).

In another embodiment of the system, the recombinant bacterium expresses propionyl-CoA transferase (PCT).

In another embodiment of the system, the recombinant bacterium has gene deletions for a negative transcriptional regulator of the β-oxidation pathway.

In another embodiment of the system, the negative transcriptional regulator is arcA or ompR.

In another embodiment of the system, the recombinant bacterium has gene deletions for arcA and ompR.

Recombinant bacteria and genetic constructs for producing the bacteria are also provided.

A recombinant bacterium is provided, wherein the bacterium:
  metabolizes short to long chain fatty acids without induction, and
  expresses an (R)-specific enoyl-CoA hydratase and a PHA synthase.

In one embodiment of the recombinant bacterium, the recombinant bacterium is a recombinant *E. coli*.

In another embodiment of the recombinant bacterium, the (R)-specific enoyl-CoA hydratase and PHA synthase have wide substrate specificities.

In another embodiment of the recombinant bacterium, the bacterium comprises a plasmid comprising an (R)-specific enoyl-CoA hydratase gene and a PHA synthase gene.

In another embodiment of the recombinant bacterium, the recombinant bacterium is a recombinant *E. coli* and the plasmid is pBBR-C1J4SII.

In another embodiment of the recombinant bacterium, β-oxidation is blocked in the recombinant bacterium.

In another embodiment of the recombinant bacterium, at least one gene encoding an enzyme for β-oxidation is inactive or deleted from the chromosome of the recombinant bacterium.

In another embodiment of the recombinant bacterium, the at least one gene encoding an enzyme for β-oxidation is a gene encoding an (S)-specific enoyl-CoA hydratase.

In another embodiment of the recombinant bacterium, the at least one gene encoding an enzyme for β-oxidation is a fad gene.

In another embodiment of the recombinant bacterium, the recombinant bacterium is recombinant *E. coli* and an (S)-specific enoyl-CoA hydratase fadB gene and/or a fadJ gene is deleted from the chromosome of the recombinant *E. coli*.

In another embodiment of the recombinant bacterium, the recombinant bacterium constitutively expresses a positive regulator of an operon, wherein the operon promotes uptake of short chain fatty acids for β-oxidation.

In another embodiment of the recombinant bacterium, the recombinant bacterium is a recombinant *E. coli* and wherein the recombinant *E. coli* constitutively expresses a positive regulator of the ato operon, thereby promoting uptake of short chain fatty acids for β-oxidation.

In another embodiment of the recombinant bacterium, the recombinant *E. coli* constitutively expresses AtoC.

In another embodiment of the recombinant bacterium, the recombinant bacterium is a recombinant *E. coli*, the (R)-specific enoyl-CoA hydratase is PhaJ4 and the PHA synthase is PhaC1(STQK).

In another embodiment of the recombinant bacterium, the recombinant bacterium expresses propionyl-CoA transferase (PCT).

In another embodiment of the recombinant bacterium, the recombinant bacterium has gene deletions for a negative transcriptional regulator of the β-oxidation pathway.

In another embodiment of the recombinant bacterium, the negative transcriptional regulator is arcA or ompR.

In another embodiment of the recombinant bacterium, the recombinant bacterium has gene deletions for arcA and ompR.

A plasmid (or vector) is provided comprising an (R)-specific enoyl-CoA hydratase gene and a PHA synthase gene.

In one embodiment of the plasmid, the plasmid comprises phaJ4 and phaC1(STQK).

In another embodiment of the plasmid, the (R)-specific enoyl-CoA hydratase and PHA synthase have wide substrate specificities.

In another embodiment of the plasmid, the plasmid is pBBR-C1J4SII.

In another embodiment of the plasmid, the plasmid comprises a pct gene.

A SCL or MCL PHA is also provided comprising a fatty acid with a terminal vinyl group (alkene and/or alkyne).

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated, enlarged, exploded, or incomplete to facilitate an understanding of the invention.

FIG. 1. Production of various poly[(R)-3-hydroxyalkanoates] (PHAs) in *Escherichia coli* LSBJ. The β-oxidation pathway of *Escherichia coli* LS5218 was altered to obtain repeating unit control in synthesis of poly(3-hydroxyalkanoates) (PHAs). The gene for the (S)-specific enoyl-CoA hydratase fadB and its homologue fadJ (formerly yfcX) were eliminated on the chromosome of *E. coli* LS5218. The new strain was named *E. coli* LSBJ. An (R)-specific enoyl CoA hydratase (PhaJ4) and PHA synthase [PhaC1(STQK)] can convert fatty acids that enter the β-oxidation pathway to PHAs at the enoyl-CoA step. The fadB and fadJ gene knockouts prevent degradation of the substrate via carbon removal, and subsequent PHAs produced contain repeating units with the same number of carbons as the starting fatty acid substrate. By feeding various ratios of fatty acids to the strain, production of PHA copolymers with specific repeating unit compositions and physical properties were achieved. See Examples 1 and 2 for details.

FIGS. 2A-B. (A) Map of *Escherichia coli* genome at the genes fadB and fadJ before and after removal of the genes. The knockout of fadB was carried out by the insertion of a chloramphenicol acetyltransferase (cat). The knockout of fadJ was carried out by insertion of a neomycin phosphotransferase and subsequent removal, leaving behind a short scar sequence. The numbers next to each map represents approximate PCR product sizes with the "check" primers in Table 2. Half arrows indicate approximate ligation sites for primers a (fadB.F.check), b (fadB.R.check), x (fadJ.F.check), and y (fadJ.R.check). (B) Agarose electrophoresis gel of PCR products of fadB and fadJ regions of *E. coli* LS5218 and *E. coli* LSBJ. Lane 1, 1 kb ladder (New England Biolabs); Lane 2, PCR from *E. coli* LS5218 using fadB.F.check and fadB.R.check primers; Lanes 3 and 4, PCR from *E. coli* LSBJ using fadB.F.check and fadB.R.check primers; Lane 5, PCR from *E. coli* LS5218 using fadJ.F.check and fadJ.R.check primers; and Lanes 6 and 7, PCR from *E. coli* LSBJ using fadJ.F.check and fadJ.R.check primers. See Examples 1 and 2 for details.

FIG. 3. H-$^{13}$C HSQC-DEPT NMR spectroscopy results for poly(3-hydroxyoctanoate) synthesized in *E. coli* LSBJ expressing the pBBR-C1J4SII plasmid. See Example 1 for more details.

FIG. 4. $^1$H-$^{13}$C HSQC-DEPT NMR spectroscopy results for poly3-hydroxydecanoate) synthesized in *E. coli* LSBJ expressing the pBBR-C1J4SII plasmid. See Example 1 for more details.

FIG. 5. H-$^{13}$C HSQC-DEPT NMR spectroscopy results for poly(3-hydroxy-10-undecenoate) synthesized in *E. coli* LSBJ expressing the pBBR-C1J4SII plasmid. See Example 1 for more details.

FIG. 6. $^1$H-$^{13}$C HSQC-DEPT NMR spectroscopy results for poly(3-hydroxydodecanoate) synthesized in *E. coli* LSBJ expressing the pBBR-C1J4SII plasmid. See Example 1 for more details.

FIGS. 7A-B. Thermal analysis of purified medium-chain-length poly(3-hydroxyalkanoates). See Example 1 for more details.

FIG. 8. 300 MHz 1H NMR spectrum of a poly[(R)-3-hydroxyoctanoate-co-(R)-3-hydroxybutyrate] sample synthesized in *E. coli* LSBJ. Cells for this sample were grown in the presence of sodium octanoate and sodium butyrate at a mole ratio of 10:90 to generate a copolymer consisting of two repeating units with eight carbons and four carbons, respectively. 3HO, (R)-3-hydroxyoctanoate; 3HB, (R)-3-hydroxybutyrate. Based on the peak integrals, this polymer sample was determined to have a 21.8:78.2 mole ratio of 3HO to 3HB. FIG. 10 (below) shows $^1$H-$^{13}$C HSQC-DEPT NMR spectroscopy results for poly(3-hydroxyoctanoate) synthesized in *E. coli* LSBJ expressing the pBBR-C1J4SII plasmid. See Example 2 for more details.

FIGS. 9A-D Summary of tensile strength analyses for various poly[(R)-3-hydroxyoctanoate-co-(R)-3-hydroxybutyrate] samples. A) Young's modulus B) strain to failure C) yield strength D) ultimate tensile strength. The x-axes of all charts represent repeating unit ratios of (R)-3-hydroxyoctanoate to (R)-3-hydroxybutyrate in the polymer samples. Values represent averages of between 4-7 experiments plus or minus standard deviations about those averages.

FIG. 10. $^1$H-$^{13}$C HSQC-DEPT NMR spectroscopy results for poly(3-hydroxyoctanoate) synthesized in *E. coli* LSBJ expressing the pBBR-C1J4SII plasmid. See Example 2 for more details.

FIG. 11. $^1$H-$^{13}$C HSQC-DEPT NMR spectroscopy results for poly(3-hydroxydecanoate) synthesized in *E. coli* LSBJ expressing the pBBR-C1J4SII plasmid.

FIG. 12. $^1$H-$^{13}$C HSQC-DEPT NMR spectroscopy results for poly(3-hydroxy-10-undecenoate) synthesized in *E. coli* LSBJ expressing the pBBR-C1J4SII plasmid. See Example 2 for more details.

FIG. 13. $^1$H-$^{13}$C HSQC-DEPT NMR spectroscopy results for poly(3-hydroxydodecanoate) synthesized in *E. coli* LSBJ expressing the pBBR-C1J4SII plasmid. See Example 2 for more details.

FIGS. 14A-B. Thermal analysis of purified medium-chain-length poly(3-hydroxyalkanoates). See Example 2 for more details.

FIG. 15. The mol ratio of repeating units in poly[(R)-3-hydroxydodecanoate-co-(R)-3-hydroxydecanoate] polymer samples in relation to the starting fatty acid substrate ratio. See Example 2 for more details.

FIG. 16. The mol ratio of repeating units in poly[(R)-3-hydroxydodecanoate-co-(R)-3-hydroxyoctanoate] polymer samples in relation to the starting fatty acid substrate ratio. See Example 2 for more details.

FIG. 17. The mol ratio of repeating units in poly[(R)-3-hydroxydecanoate-co-(R)-3-hydroxyoctanoate] polymer samples in relation to the starting fatty acid substrate ratio. See Example 2 for more details.

FIG. 18. The mol ratio of repeating units in poly[(R)-3-hydroxyoctanoate-co-(R)-3-hydroxybutyrate] polymer samples in relation to the starting fatty acid substrate ratio. See Example 2 for more details.

FIG. 19. TGA scans of various poly[(R)-3-hydroxyoctanoate-co-(R)-3-hydroxybutyrate] samples synthesized in *E. coli* LSBJ containing the pBBR-C1J4SII plasmid. See Example 2 for more details.

FIG. 20. DSC scans of various poly[(R)-3-hydroxyoctanoate-co-(R)-3-hydroxybutyrate] samples synthesized in *E. coli* LSBJ containing the pBBR-C1J4SII plasmid. See Example 2 for more details.

FIG. 21. Examples of data generated in tensile strength analysis experiments with poly[(R)-3-hydroxyoctanoate-co-(R)-3-hydroxybutyrate] samples. See Example 2 for more details.

FIG. 22. Fitted line plot of the natural logarithm of Young's modulus values (LN_Yng) against the percent of 3HO (C8_Proportion) in of poly[(R)-3-hydroxyoctanoate-co-(R)-3-hydroxybutyrate] samples. LN_Yng=5.724–0.1157 Plot was made in the MINITAB software program. See Example 2 for more details.

FIG. 23. Fitted line plot of the natural logarithm of ultimate tensile strength values (LN_Tens) against the percent of 3HO (C8_Proportion) in of poly[(R)-3-hydroxyoctanoate-co-(R)-3-hydroxybutyrate] samples. LN_Tens=2.779–0.07740. Plot was made in the MINITAB software program. See Example 2 for more details.

FIGS. 24A-C. $^1$H NMR spectra of poly[(R)-3-hydroxyoctanoate-co-(R)-3-hydroxybutyrate] containing 68.7% PHB prior to and after acetone fractionation. A, sample spectra prior to acetone fractionation. B, acetone soluble fraction. C, acetone insoluble fraction. See Example 2 for more details.

FIG. 25. DSC results of poly[(R)-3-hydroxyoctanoate-co-(R)-3-hydroxybutyrate] containing 68.7% PHB before and after acetone fractionation. Scans were offset for clarity. The top scan is of the sample prior to acetone fractionation. The middle scan is the acetone soluble fraction. The bottom scan is the acetone insoluble fraction.

FIG. 26. Synthetic pathways for the production of PHA polymers from fatty acids in *E. coli*. A. Fatty acids are activated for degradation by the acyl-CoA ligase, FadD where they enter the β-oxidation pathway. B. 3-Ketoacyl reductases such as FabG and RhlG can be overexpressed to convert 3-ketoacyl-CoA to (R)-3-hydroxyacyl-CoA. C. (R)-specific enoyl-CoA hydratases can be overexpressed to convert enoyl-CoA to (R)-3-hydroxyacyl-CoA. D. PhaC polymerizes the precursors generated by the two pathways into PHA.

FIG. 27. Engineering *E. coli* to produce PHA polymers with defined repeating unit compositions. Several modifications in this strain result in the production of PHA polymers with defined repeating unit compositions: (i) fadR mutation results in constitutive expression of the fad genes, (ii) atoC(Con) results in constitutive expression of the ato genes, (iii) deletion of the fadB and fadJ genes results in the pooling of enoyl-CoA intermediates of defined carbon lengths from fed fatty acids, (iv) expression of phaJ results in the conversion of specific enoyl-CoA substrates to (R)-3-hydroxyacyl-CoA substrates, and (v) expression of phaC1 (STQK) results in polymerization of the (R)-3-hydroxyacyl-CoA substrates into PHA polymers dependent on the ratio of fatty acids fed to the strain.

FIG. 28. The mol ratio of repeating units in poly[(R)-3-hydroxyoctanoateco-(R)-3-hydroxybutyrate] polymer samples in relation to starting fatty acid substrate ratios. The fatty acid substrates were used by *E. coli* LSBJ. All values were determined by 1H NMR and represent average integrations of three separate peaks in the 1H NMR spectra. These integrations were compared to the integration of a peak unique to the 8-carbon repeating unit. Error bars represent standard deviations about those averages.

FIG. 29. Gene rearrangement to control molecular weights of MCL PHA-co-PLA polymers. Synthetic operons for MCL PHA-co-PLA polymer production will be made via Gibson assembly. Overlaying primers will be designed to rearrange all monomer-supplying genes (pct, phaG, and alkK) relative to the PHA synthase gene encoding phaC1 (STQK) shown here as phaC1.

FIG. 30. Engineering transcriptional regulators in *E. coli* for enhanced fatty acid uptake. Regulation of the *E. coli* fad regulon responds to several environmental stimuli including: long chain fatty acids (LCFA), glucose, oxygen, and osmotic stress. These external stimuli influence a number of regulatory proteins (in bold) including FadR, catabolite repression protein, ArcA-P, and OmpR. The fad regulon components are in italics and are either positively regulated as indicated by a black arrow "↓" or repressed as denoted by a gray "⊥".

FIG. 31. Engineering *E. coli* for precise control of MCL PHA and PLA repeating unit composition. *E. coli* LSBJ has mutations [atoC(Con), fadR, fadB, fadJ] for the acquisition and conversion of small organic acids like lactic acid and fatty acids. With the co-expression of the (R)-specific enoyl-CoA hydratase, PhaJ, PHA synthase, PhaC, and propionyl-CoA transferase, PCT, the strain can easily be engineered for the production of PHA-co-PLA polymers. The ratio of PHA to PLA incorporated into the copolymer will be dependent on the ratio of feedstocks (fatty acids:lactic acid) available to the strain. By feeding different ratios of lactic acid and fatty acid to the cells and determining the polymer composition, copolymers with desired ratios of PHA to PLA repeating units can be made. The system shown here is for MCL PHA-co-PLA polymer production but can be readily adapted for the production of SCL PHA-co-PLA polymers with desired repeating unit compositions.

FIG. 32. Poly[(R)-3-hydroxy-10-undecenoate-co-(R)-3-hydroxyoctanoate] production in *E. coli* LSBJ harboring the pBBR-C1J4SII plasmid. The (R)-3-hydroxy-10-undecenoate repeating units were provided by 10-undecenoate, and the (R)-3-hydroxyoctanoate repeating units were provided by sodium octanoate. The relative concentration of fatty acid substrates was varied to demonstrate the corresponding change in terminal alkenes present in the polymer product (determined by NMR). This plot portrays the change in concentration of terminal alkenes in repeating units of PHAs as a function of starting concentration of 10-undecenoate relative to total fatty acid content.

FIG. 33. 300 MHz $^1$H NMR spectrum of a poly[(R)-3-hydroxy-10-undecenoate-co-(R)-3-hydroxyoctanoate] sample synthesized by *E. coli* LSBJ carrying the pBBR-C1J4SII plasmid. Cells were grown with 10-undecenoate and sodium octanoate at a mole ratio of 50:50 to generate this sample. 3HUnΔ10, (R)-3-hydroxy-10-undecenoate; 3HO, (R)-3-hydroxyoctanoate. Based on the peak integrations, it was determined that this polymer had a 3HUnΔ10:C8 mole ratio of 72.3:27.7.

5. DETAILED DESCRIPTION OF THE INVENTION

An *Escherichia coli*-based system is provided for producing PHA polymers (also referred to herein as "PHAs") with defined repeating unit composition. The system can be used to control repeating unit composition in PHAs. Methods for producing PHA polymers using the system are also provided. Recombinant bacteria and genetic constructs for producing the bacteria are also provided.

The system and method can be used for producing desired PHAs of virtually any repeating unit composition desired, including long-chain length (LCL), medium-chain length (MCL) and short-chai-length (SCL). Over 150 PHA monomers are known in the art, and the system and methods disclosed herein can produce virtually any desired combination of repeating unit composition, millions of different types of PHAs with different physical properties, can be produced.

In a specific embodiment, a method for producing PHAs with defined repeating unit composition is also provided. In one embodiment, the method utilizes *E. coli* and comprises the step of providing an *E. coli* chromosome in which the eliminating the fadB and fadJ genes from the β-oxidation pathway have been eliminated. In a specific embodiment, the *E. coli* chromosome LS5218.

The subsequent blockage in β-oxidation causes a buildup of enoyl-CoA intermediates. The method also comprises the step of converting the enoyl-CoA intermediates PHAs by an (R)-specific enoyl-CoA hydratase (PhaJ4) and PHA synthase [PhaC1 (STQK)] expressed from a plasmid DNA construct.

In another embodiment, the method can comprise the step of providing fatty acid substrates and converting fatty acid substrates to PHAs with repeating units equal in the number of carbon atoms to the fatty acid substrates. The broad substrate specificities of the PhaJ4 and PhaC1(STQK) enzymes allows for the production of homopolymers with strict control over the repeating unit composition.

In another embodiment, a modified *Escherichia coli* strain is provided to allow for control over repeating unit composition of poly(3-hydroxyalkanoate) (PHA) polymers. In one embodiment, *E. coli* LS5218 is used as the parent strain. *E. coli* LS5218 metabolizes short to long chain fatty acids without induction. In one embodiment, the β-oxidation pathway of *E. coli* LS5218 is blocked at the enoyl-CoA intermediate by gene deletion of (S)-specific enoyl-CoA hydratases, fadB and fadJ. PHAs are synthesized from enoyl-CoA intermediates in the β-oxidation pathway by an (R)-specific enoyl-CoA hydratase (PhaJ4) and PHA synthase (PhaC1(STQK)) expressed from a plasmid construct.

A repeating unit of desired (or prescribed) length in carbon atoms is selected by providing the modified *E. coli* with a fatty acid equal in number of carbons. Both PHA homopolymer and PHA copolymer repeating unit compositions may be controlled. In a specific embodiment, PHA homopolymer biosynthesis produces repeating units from four to twelve carbons in length. In other embodiments, PHA copolymer composition can be controlled via manipulation of different fatty acid ratios made available to the *E. coli*.

For clarity of disclosure, and not by way of limitation, the detailed description of the invention is divided into the subsections set forth below.

5.1 Method for Producing a Prescribed Unit Size poly(3-hydroxyalkanoate) (PHA) Polymer and Recombinant Bacterium for use therein A method is provided for producing a prescribed unit size poly(3-hydroxyalkanoate) (PHA) polymer. A recombinant bacterium for use in the method is also provided.

In one embodiment of the method, the method comprises the steps of:

providing a recombinant (i.e., genetically engineered) bacterium, wherein the bacterium:
  metabolizes short to long chain fatty acids without induction, and
  expresses an (R)-specific enoyl-CoA hydratase and a PHA synthase;

feeding at least one fatty acid substrate to the recombinant bacterium, the at least one fatty acid substrate being of equal carbon length to the prescribed unit size of the PHA polymer to be produced; and isolating and/or purifying the PHA from the recombinant bacterium, thereby producing the PHA polymer.

A prescribed unit size refers to the desired number of carbon atoms that are in the unit.

In one embodiment, the (R)-specific enoyl-CoA hydratase and PHA synthase have wide substrate specificities.

The PHA polymer can be a PHA homopolymer or a PHA copolymer. More than 150 PHA monomers are known in the art. PHA homopolymers or copolymers can be produced from any PHA monomer and/or combination of monomers known in the art. PHA copolymers can consist of random mixtures of repeating units of different sizes, where the composition depends upon the carbon source, the growth conditions, and the organism chosen for producing the PHAs.

In a preferred embodiment of the method, the recombinant bacterium is a recombinant *E. coli*. In other embodiments, other bacteria known in the art to be suitable for bacterial fermentation, such as *Ralstonia eutropha, Cupriavidus necator, Alcaligenes lattus, Pseudomonas* spp., (e.g., *Pseudomonas putida, Pseudomonas oleovorans, Pseudomonas aeruginosa*), *Aeromonas cavia, Burkholderia cepacia, Bacillus subtilis, Pseudomonas* sp. 61-3, *Corynebacterium glutamicum* and *Bacillus* spp. can be used.

In another embodiment of the method, the step of providing a recombinant bacterium comprises the step of constructing a plasmid comprising an (R)-specific enoyl-CoA hydratase gene and a PHA synthase gene and transforming the plasmid into the recombinant bacterium. Methods for transforming bacteria with plasmids are well known in the art.

Genetic constructs and vectors are also provided. In one embodiment, a plasmid is provided comprising an (R)-specific enoyl-CoA hydratase gene and a PHA synthase gene. In a specific embodiment, the plasmid is pBBR-C1J4SII, as described in Examples 1 and 2.

In a specific embodiment of the method, the recombinant bacterium is a recombinant *E. coli* and the plasmid is pBBR-C1J4SII, described in Examples 1 and 2 below. Plasmids can be constructed using methods well known in the art. To construct pBBR-C1J4SII, for example, the phaJ4 gene from *Pseudomonas putida* KT2440 is PCR amplified using the phaJ4 primers "phaJ4 left EcoRV" and "phaJ4 right KpnI" (Table 2), PrimeSTAR HS DNA polymerase (Takara), and an iCycler thermal cycler (Bio-Rad). The PCR product is gel-purified and cloned into the pCR-Blunt (Invitrogen) vector with T4 DNA ligase (New England Biolabs). Successful ligations are confirmed via sequencing from Genewiz. The resulting Blunt-phaJ4 vector is digested with KpnI and the excised piece phaJ4 DNA is ligated into the KpnI site of the plasmid pBBRSTQKAB, creating pBBRSTQKABJ4. Correct orientation of the phaJ4 gene on the pBBRSTQKABJ4 plasmid is confirmed by restriction enzyme digest with BamHI. pBBRSTQKABJ4 is then digested with SacII to excise the unnecessary genes phaA and phaB. The linearized DNA fragment is gel-purified and ligated together at the SacII site with T4 DNA ligase, generating pBBR-C1J4SII. pBBR-C1J4SII can be transformed into *E. coli* LSBJ following standard procedures and grown on LB agar plates with kanamycin. Single colonies are added to 50 ml LB cultures with kanamycin and grown for 12-16 hours in a 30° C. incubator with shaking at 250 rpm. One milliliter of the overnight culture is used to inoculate 100 ml of LB with kanamycin, a fatty acid substrate at 2 g $L^{-1}$, and the surfactant Brij-35 (Fisher Scientific) at 4 g $L^{-1}$ in a baffled flask. The flasks are incubated at 30° C. with shaking at 250 rpm for 48 hours. Cells are incubated, harvested and dried via lyophilization.

To ensure repeating unit control of PHA synthesis could be ascertained over a large range of repeating unit lengths, the (R)-specific enoyl-CoA hydratase and PHA synthase preferably both have wide substrate specificities. In one embodiment, PhaJ4 from *Pseudomonas putida* KT2440 can be used for converting the enoyl-CoA intermediate of β-oxidation to (R)-3-hydroxyacyl-CoA.

In another embodiment of the method, β-oxidation is blocked in the recombinant bacterium, thereby causing a buildup of enoyl-CoA intermediates.

In another embodiment of the method, at least one gene encoding an enzyme for β-oxidation is inactive or deleted from the chromosome of the recombinant bacterium. Such methods are known in the art, examples of which are described in Examples 1 and 2.

In another embodiment of the method, a plurality of genes encoding enzymes for β-oxidation is inactive or deleted from the chromosome of the recombinant bacterium.

In another embodiment of the method, the at least one gene encoding an enzyme for β-oxidation is a gene encoding an (S)-specific enoyl-CoA hydratase.

In another embodiment of the method, the at least one gene encoding an enzyme for β-oxidation is a fad gene.

In a preferred embodiment of the method, the recombinant bacterium is recombinant *E. coli* and an (S)-specific enoyl-CoA hydratase fadB gene and/or a fadJ gene is deleted from the chromosome of the recombinant *E. coli*.

Deletions of enzymes involved in fatty acid degradation and expression of PHA synthesis enzymes with broad substrate specificities allow for controlled PHA synthesis utilizing fatty acid substrates equal in length to the desired repeating unit. The fatty acid starting materials enter the β-oxidation pathway but are stopped at the enoyl-CoA intermediate (FIG. 1). Instead of proceeding through β-oxidation and degrading, the enoyl-CoA intermediate accumulates due to elimination of the (S)-specific enoyl-CoA hydratasefadB and its homologue fadJ (formerly yfcX). Deletion of these genes from *E. coli* eliminates the ability of the organism to grow on fatty acids. Since the β-oxidation pathway is stopped prior to degradation of the fatty acid, any fatty acids that enter the pathway are converted to PHA substrates equal in length as the starting fatty acid.

In a specific embodiment, the enoyl-CoA intermediates are converted to (R)-3-hydroxyacyl-CoA by the (R)-specific enoyl-CoA hydratase (PhaJ4) and polymerized by a PHA synthase [PhaC1(STQK)].

In another embodiment of the method, the recombinant bacterium constitutively expresses a positive regulator of an operon, wherein the operon promotes uptake of short chain fatty acids for β-oxidation.

In another embodiment of the method, the recombinant bacterium is a recombinant *E. coli* and the recombinant *E. coli* constitutively expresses a positive regulator of the ato operon, thereby promoting uptake of short chain fatty acids for β-oxidation. In a specific embodiment, the recombinant *E. coli* constitutively expresses AtoC.

In another embodiment of the method, the recombinant bacterium is a recombinant *E. coli*, the (R)-specific enoyl-CoA hydratase is PhaJ4 and the PHA synthase is PhaC1 (STQK).

Any suitable fatty acid known in the art can be used as a substrate. Suitable fatty acids preferably do not have substituents that prevent it from entering or being taken up by the recombinant bacterium. Two or more (i.e., a plurality) of fatty acid substrates can be co-fed to the bacteria at varying ratios for incorporation into a PHA polymer or copolymer with a desired or controlled repeating unit composition. In a specific embodiment, the fatty acid substrates are 3-12 carbons in length. In another embodiment, the fatty acid substrates are 3-16 carbons in length.

Thus, in another embodiment of the method, at least two different types of fatty acid substrates of desired length are fed to the recombinant bacteria in a desired ratio, thereby producing a PHA polymer or PHA copolymer of desired (or controlled) repeating unit composition. Methods for selecting substrates of desired length in a desired ratio to produce a PHA polymer or PHA copolymer of desired (or controlled) repeating unit composition are described in Examples 1 and 2.

Methods for culturing recombinant bacteria (e.g., bacterial fermentation) to produce a bacterially produced (fermentation) product are also well known in the art.

In one embodiment of the method, PHA is isolated or purified from the recombinant bacteria, thereby producing a PHA polymer. Methods for recovering PHAs from recombinant bacteria are described herein.

In a specific embodiment, the recombinant bacteria are cultured (e.g., in batch fermentation or culture) and the PHA recovered from the cultured bacteria. Such methods are well known in the art.

Characterization and determination of physical properties of PHAs produced by the method and system disclosed herein can be performed using techniques well known in the art. Repeating unit compositions of PHAs can be determined by gas chromatography (GC) and gas chromatography-mass spectroscopy (GC-MS). The number-average molecular weight ($M_n$) and the weight-average molecular weight ($M_w$) can be determined by gel permeation chromatography (GPC). Nuclear magnetic resonance can be performed for further structural analysis Thermal analysis can be performed to determine such characteristics as decomposition temperatures ($T_d$), glass-transition temperatures ($T_g$), melting temperatures ($T_m$), and crystallization temperatures ($T_c$).

In other embodiments, growth and polymer production can also be performed using undecylenic acid and lactic acid at similar ratios. Undecylenic acid is an 11-carbon fatty acid with a terminal alkene, allowing the insertion of a chemically reactive handle into the polymers produced. PHA polymers containing repeating units with terminal alkenes have been chemically modified to expand the number of applications for drug delivery and shape-memory polymers.

5.2 System for Producing a Prescribed Unit Size poly(3-hydroxyalkanoate) (PHA) Polymer A system is provided for producing a prescribed unit size poly(3-hydroxyalkanoate) (PHA) polymer. The system comprises the recombinant bacterium described above in Section 5.1

Thus in one embodiment of the system, the system comprises a recombinant (genetically engineered) bacterium, wherein the bacterium:
  metabolizes short to long chain fatty acids without induction, and
  expresses an (R)-specific enoyl-CoA hydratase and a PHA synthase In one embodiment, the (R)-specific enoyl-CoA hydratase and PHA synthase have wide substrate specificities.

A prescribed unit size refers to the desired number of carbon atoms that are in the unit.

In another embodiment of the system, the PHA polymer is a PHA homopolymer or a PHA copolymer.

In another embodiment of the system, the recombinant bacterium is a recombinant E. coli.

In another embodiment of the system, the recombinant bacterium comprises a plasmid comprising an (R)-specific enoyl-CoA hydratase gene and a PHA synthase gene.

In another embodiment of the system, the recombinant bacterium is a recombinant E. coli and the plasmid is pBBR-C1J4SII.

In another embodiment of the system, β-oxidation is blocked in the recombinant bacterium, thereby causing a buildup of enoyl-CoA intermediates.

In another embodiment of the system, at least one gene encoding an enzyme for β-oxidation is inactive or deleted from the chromosome of the recombinant bacterium.

In another embodiment of the system, the at least one gene encoding the enzymes for β-oxidation are is a fad gene.

In another embodiment of the system, a plurality of genes encoding enzymes for β-oxidation is inactive or deleted from the chromosome of the recombinant bacterium.

In another embodiment of the system, the at least one gene encoding an enzyme for β-oxidation is a gene encoding an (S)-specific enoyl-CoA hydratase.

In another embodiment of the system, the at least one gene encoding an enzyme for β-oxidation is a fad gene.

In another embodiment of the system, the recombinant bacterium is recombinant E. coli and an (S)-specific enoyl-CoA hydratase fadB gene and/or a fadJ gene is deleted from the chromosome of the recombinant E. coli.

In another embodiment of the system, the recombinant bacterium constitutively expresses a positive regulator of an operon, wherein the operon promotes uptake of short chain fatty acids for β-oxidation.

In another embodiment of the system, the recombinant bacterium is a recombinant E. coli and wherein the recombinant E. coli constitutively expresses a positive regulator of the ato operon, thereby promoting uptake of short chain fatty acids for β-oxidation.

In another embodiment of the system, the recombinant E. coli constitutively expresses AtoC.

In another embodiment of the system, the recombinant bacterium is a recombinant E. coli, the (R)-specific enoyl-CoA hydratase is PhaJ4 and the PHA synthase is PhaC1 (STQK).

5.3 Poly(3-hydroxyalkanoates) (PHAs) Produced by the Method and System

Poly(3-hydroxyalkanoate) (PHA) polymers and copolymers are provided with prescribed unit size repeating units.

Poly(3-hydroxyalkanoates) (PHAs) are biodegradable plastics and carbon storage materials that are synthesized by a myriad of microorganisms. PHAs are divided into groups based on repeating unit size. PHAs with repeating units of three to five carbons in length are short-chain-length (SCL) PHAs, and PHAs with repeating units of six to fourteen carbons in length are medium-chain-length (MCL) PHAs. Differences in repeating unit composition influence the physical properties of PHAs. Both short-chain-length (SCL) PHAs and medium-chain-length (MCL) PHAs are provided.

In specific embodiments, SCL and MCL PHAs comprising fatty acids with terminal vinyl groups (alkenes and alkynes) are provided.

Gaining control over such a broad range of repeating units in PHAs, as provided by the method and system described herein, is useful for numerous applications in which PHAs can be used, particularly for the production of MCL PHAs that can then be analyzed for medical uses. Various SCL-co-MCL PHA copolymers have been tested for heart valve engineering, nerve regeneration, skin regeneration, drug delivery and more. These applications require specific physical properties that can be attained with the proper ratio of repeating units within PHAs, as described in more detail in Examples 1 and 2. The method and system disclosed herein allows for selection of repeating unit sizes and ratios aids in synthesis of PHAs with medically relevant physical properties.

The following examples are offered by way of illustration and not by way of limitation.

6. EXAMPLES

6.1 Example 1

Precise Control of Repeating Unit Composition in Biodegradable poly[(R)-3-hydroxyalkanoate] Polymers Synthesized by *Escherichia coli*

The composition of medium-chain-length (MCL) poly(3-hydroxyalkanoate) (PHA) biopolymers is normally an uncontrollable random mixture of repeating units with differing side chain lengths. Attempts to generate MCL PHA homopolymers and gain control of the repeating unit composition have been published in native PHA-producing organisms but have limited ranges for the different sizes of repeating units that can be synthesized. This example describes an *Escherichia coli*-based system that exhibits control over repeating unit composition of both MCL and short-chain-length (SCL) PHAs, covering an unprecedented range of repeating units. The fadB and fadJ genes from the β-oxidation pathway were eliminated from the chromosome of *E. coli* LS5218. The subsequent blockage in β-oxidation caused a buildup of enoyl-CoA intermediates, which were converted to PHAs by an (R)-specific enoyl-CoA hydratase (PhaJ4) and PHA synthase (PhaC1(STQK)) expressed from a plasmid DNA construct. Fatty acid substrates were converted to PHAs with repeating units equal in the number of carbon atoms to the fatty acid substrate. The broad substrate specificities of the PhaJ4 and PhaC1(STQK) enzymes allowed for the production of homopolymers with strict control over the repeating unit composition from substrates of four to twelve carbons in length. Polymers were purified and analyzed by GC, GC-MS, and NMR for structural composition and by DSC, TGA, and GPC for thermal and physical characteristics. This study marks the development of the first single biological system to achieve consistent repeating unit control over such a broad range of repeating units in PHAs.

Introduction

Poly(3-hydroxyalkanoates) (PHAs) are biodegradable plastics and carbon storage materials that are synthesized by a myriad of microorganisms (1). PHAs are divided into groups based on repeating unit size. PHAs with repeating units of three to five carbons in length are short-chain-length (SCL) PHAs, and PHAs with repeating units of six to fourteen carbons in length are medium-chain-length (MCL) PHAs. Differences in repeating unit composition influence the physical properties of PHAs (2,3). Production of SCL PHA homopolymers such as poly-3-hydroxybutyrate (PHB) is well studied (4,5). Previous attempts to control MCL PHA synthesis in native and recombinant PHA-producing organisms, however, have resulted in narrow ranges of repeating unit control (6-9). Typically, control is limited to only a couple of repeating units within one organism, (6,7,9) or control is lost once the number of carbons in the repeating unit exceeds seven (8). In this example, Escherichia coli LS5218 has been engineered to develop a new PHA-production system capable of synthesizing PHAs with repeating unit compositions based solely on the carbon chain length of fatty acid substrates fed to the strain. PHA synthesis control is demonstrated for repeating units from four and up to twelve carbons long, spanning both SCL and MCL PHAs.

Gaining control over such a broad range of repeating units in PHAs is useful for a number of applications for which PHAs can be used, particularly for the production of MCL PHAs for medical uses. Various SCL-co-MCL PHA copolymers have been tested for heart valve engineering, nerve regeneration, skin regeneration, drug delivery and more (10). These applications require specific physical properties that may be attained with the proper ratio of repeating units within PHAs. The system disclosed herein allows for selection of repeating unit sizes and ratios aids in synthesis of PHAs with medically relevant physical properties.

In this example, PHAs with homogenous repeating units were synthesized to demonstrate control over repeating unit size selection. This work demonstrates an engineered microbial system capable of controlling the molecular composition of PHA polymers over a broad range of repeating unit sizes including MCL and SCL PHAs.

Deletions of enzymes involved in fatty acid degradation and expression of PHA synthesis enzymes with broad substrate specificities allow for controlled PHA synthesis utilizing fatty acid substrates equal in length to the desired repeating unit. The fatty acid starting materials enter the β-oxidation pathway but are stopped at the enoyl-CoA intermediate (FIG. 1). Instead of proceeding through β-oxidation and degrading, the enoyl-CoA intermediate accumulates due to elimination of the (S)-specific enoyl-CoA hydratase fadB and its homologue fadJ (formerly yfcX). Deletion of these genes from E. coli eliminates the ability of the organism to grow on fatty acids (11). Numerous studies have been carried out that utilize β-oxidation mutations to promote PHA synthesis in vivo (12-16). However, no work has been presented with mutations of both fadB and fadJ for the production of PHAs comprised of specific repeating units as displayed here. Since the β-oxidation pathway is stopped prior to degradation of the fatty acid, any fatty acids that enter the pathway are converted to PHA substrates equal in length as the starting fatty acid. The enoyl-CoA intermediates were converted to (R)-3-hydroxyacyl-CoA by the (R)-specific enoyl-CoA hydratase (PhaJ4) and polymerized by a PHA synthase [PhaC1(STQK)].

E. coli LS5218 was chosen as the parental strain for generating this system because of its abilities to uptake and degrade a broad range of fatty acids. Normally, the E. coli genes responsible for uptake and degradation of medium to long-chain fatty acids via the β-oxidation pathway require induction by fatty acids of at least fourteen carbons in length (17). E. coli LS5218 has a mutated fadR gene, which leads to constitutive expression of the fad genes encoding the enzymes for β-oxidation (12,18). E. coli LS5218 also has an atoC(Con) mutation allowing for constitutive expression of AtoC, a positive regulator of the ato operon, which is responsible for uptake of short chain fatty acids for β-oxidation (19,20). These mutations allow LS5218 to readily metabolize short to very long chain fatty acids without induction.

To ensure repeating unit control of PHA synthesis could be ascertained over a large range of repeating unit lengths, the (R)-specific enoyl-CoA hydratase and PHA synthase must both have wide substrate specificities. Therefore, PhaJ4 from Pseudomonas putida KT2440 was selected for converting the enoyl-CoA intermediate of β-oxidation to (R)-3-hydroxyacyl-CoA. PhaJ4 from P. putida KT2440 has 78% amino acid identity to PhaJ4 from Pseudomonas aeruginosa, which was reported to have relatively high activity for enoyl-CoA substrates ranging in size from four to twelve carbons (21,22). (R)-specific enoyl-CoA hydratases have been used numerous times to synthesize PHAs (14, 21-25), but none of the studies demonstrated the ability to control PHA repeating unit composition as the system generated here.

The PHA synthase used in this work was PhaC1(STQK), an engineered PHA synthase derived from the native Pseudomonas sp. 61-3 PHA synthase (26). The wild type PHA synthase was unique in its ability to incorporate both SCL and MCL units in PHAs (27) and was engineered to increase its ability to incorporate SCL units. This PHA synthase has been used successfully to produce PHAs containing repeat units of four to twelve carbons in length (28,29), making it a suitable partner for the PhaJ4 enzyme for synthesizing a wide range of PHAs with varying side chain lengths.

The unique E. coli repeating unit control system developed in this study allows for unprecedented control of PHA repeating unit composition within one bacterial strain. The desired repeating unit(s) can be selected for incorporation into PHAs simply by selecting the fatty acid substrate of equal carbon length. This system has several advantages over previous attempts at producing PHA homopolymers. The E. coli strain made in this study is capable of utilizing a wide range of fatty acids, without induction, and converting them to PHA polymers with uniform repeating unit composition. Another advantage is that E. coli is not a native producer of PHAs and lacks the enzymes to degrade the PHAs once synthesized. This study demonstrates, for the first time within one biological system, PHA production with the ability to tightly control repeating unit composition for repeating units from four and up to twelve carbons.

Example 2 describes the next step in this work, which is the production of specified short-chain-length and mediumchain-length single repeating units in poly[(R)-3-hydroxy-alkanoates] synthesized in E. coli using fatty acid substrates.

Example 3 describes synthesis of SCL-MCL PHA, MCL PHA-co-PLA, or SCL-MCL PHA-co-PLA co-polymers from fatty acid substrates.

Materials and Methods
Media and Cultivation

Strains and plasmids used in this example are listed in Table 1. All E. coli strains were grown on Lennox Broth (LB; composition per liter: 10 g tryptone, 5 g yeast extract, and 5 g sodium chloride) at 30° C. and 250 rpm on a rotary shaker. The following antibiotics were added as appropriate to growth media: kanamycin at 50 µg ml$^{-1}$, ampicillin at 100 µg ml$^{-1}$, and chloramphenicol at 30 µg ml$^{-1}$. Any further additions to the media or culture conditions were as described below.

TABLE 1

Strains and plasmids

| Strain of Plasmid | Relevant Characteristics | Source or Reference |
|---|---|---|
| Strains | | |
| E. coli LS5218 | fadR601, atoC(Con) | Coli Stock Center |
| E. coli JM109 | recA1 endA1 gyrA96 thi-1 hsdR17 ($r_K^-m_K^+$) supE44 relA1 l-lac [F' proAB lacI$^q$ ZDM15] | Promega |
| E. coli LSBJ | E. coli LS5218 fadB::Cm, fadJ(−) | This Example |
| Plasmids | | |
| pKD46 | λ Red recombinase expression plasmid; expresses exo, β, and γ genes from λ phage; P$_{araB}$ promoter; araC; Amp$^r$; temperature sensitive replicon | Datsenko & Wanner, 2000 |
| pKD3 | Chloramphenicol acetyltransferase flanked by FLP recombinase recognition targets, Amp$^r$, Cm$^r$ | Datsenko & Wanner, 2000 |
| pKD13 | Neomycin phosphotransferase flanked by FLP recombinase recognition targets, Km$^r$, Amp$^r$ | Datsenko & Wanner, 2000 |
| pCP20 | FLP recombinase expression plasmid, Amp$^r$, temperature sensitive replicon | Datsenko & Wanner, 2000 |
| pBBRSTQKAB | pBBR1MCS-2 derivative, phaC1 (STQK), phaAB | Nomura et al., 2004 |
| pBBRSTQKABJ4 | pBBRSTQKAB derivative, phaJ4 | This Example |
| pBBR-C1J4SII | SacII digest of pBBRSTQKABJ4 (to remove phaAB), phaJ4, phaC1 (STQK) | This Example |
| pCR-Blunt | Cloning vector for blunt PCR-cloning, ccdB-lacZfusion, Km$^r$ | Invitrogen |
| Blunt-J4 | pCR-Blunt derivative, phaJ4 | This Example |

Gene Knockouts in E. coli LS5218

The method for chromosomal gene inactivation in E. coli developed by Datsenko and Wanner (30) was used to inactivate the fadB and fadJ genes in E. coli LS5218. Primers for the antibiotic genes within plasmids pKD13 and pKD3 contained ends homologous to fadJ and fadB, respectively (Table 2). Knockout cassettes were amplified from appropriate plasmid templates using PrimeSTAR HS DNA polymerase (Takara) and an iCycler thermal cycler (Bio-Rad) following manufacturers' recommendations. E. coli LS5218 carrying the pKD46 plasmid was grown in LB with 0.3% (w/v) L-arabinose to induce expression of the λ Red system. Cells that had expressed the λ Red system from the pKD46 plasmid and grown to an OD$_{600}$ of ~0.6 were made electrocompetent and transformed with PCR knockout cassettes via an ECM 399 electroporator (BTX) at 1500 volts following the manufacturer's protocols for E. coli. Transformants were selected on LB-agar plates with the appropriate antibiotic. Elimination of the genes from the chromosome was confirmed by PCR (FIGS. 2A-B). The temperature-sensitive plasmid pKD46 was expelled from the cells by growth at 37° C.

The gene encoding fadJ was eliminated from E. coli LS5218 first by insertion of the gene expressing kanamycin resistance into the fadJ gene on the chromosome. This insert was removed by expression of FLP recombinase from the pCP20 plasmid. Successful removal was confirmed by PCR and loss of kanamycin resistance. The temperature-sensitive plasmid pCP20 was expelled from the cells by growth at 37° C. After fadJ was eliminated, fadB was eliminated by insertion of the chloramphenicol acetyltransferase cassette from pKD3. All deletions were confirmed by PCR (FIGS. 2A-B).

TABLE 2

Oligonucleotide primers

| Primers | Sequence$^a$ (5' to 3') |
|---|---|
| Gene Knockout | |
| pKD13.F. fadJ | ATGGAAATGACATCAGCGTTTACCCTTAATGTTCGTCT GGACAACATTGCGTGTAGGCTGGAGCTGCTTC (SEQ ID NO: 1) |
| pKD13.R. fadJ | TTATTGCAGGTCAGTTGCAGTTGTTTTCCAAAAACTTT CCCCACGCGCGCATTCCGGGGATCCGTCGACC (SEQ ID NO: 2) |
| pKD3.F. fadB | ATGCTTTACAAAGGCGACACCCTGTACCTTGACTGGCT GGAAGATGGCATGTGTAGGCTGGAGCTGCTTC (SEQ ID NO: 3) |

TABLE 2-continued

Oligonucleotide primers

| Primers | Sequence[a] (5' to 3') |
|---|---|
| pKD3.R. fadB | TTAAGCCGTTTTCAGGTCGCCAACCGGACGGGCTGGCT<br>CAACCGGAGGATCATATGAATATCCTCCTTAG<br>(SEQ ID NO: 4) |
| fadJ.F. check | GGTTTAGTTACCGCCTGTGC<br>(SEQ ID NO: 5) |
| fadJ.R. check | AGCGCGGATTCATATAGCTT<br>(SEQ ID NO: 6) |
| fadB.F. check | GCGAGTCCGTTCTTGTAAGG<br>(SEQ ID NO: 7) |
| fadB.R. check | CGAATTGCATCGACAATGAC<br>(SEQ ID NO: 8) |
| PHA-Expression | |
| phaJ4 F KpnI | ATTGGTACCCAACTGACAACCCGGAGAGT<br>(SEQ ID NO: 9) |
| phaJ4 R EcoRV | ATTGATATCCTGGCAGTTTACGCGAGTG<br>(SEQ ID NO: 10) |

[a]Underlined sequences are homologous to genes to be knocked out and sequences in bold are restriction enzyme sites Construction of pBBR-C1J4SII Vector for PHA Production The phaJ4 gene from *Pseudomonas putida* KT2440 (22, 31) was PCR amplified using the phaJ4 primers "phaJ4 left EcoRV" and "phaJ4 right KpnI" (Table 2), PrimeSTAR HS DNA polymerase (Takara), and an iCycler thermal cycler (Bio-Rad). The PCR product was gel-purified and cloned into the pCR-Blunt (Invitrogen) vector with T4 DNA ligase (New England Biolabs). Successful ligations were confirmed via sequencing from Genewiz. The resulting Blunt-phaJ4 vector was digested with KpnI and the excised piece phaJ4 DNA was ligated into the KpnI site of the plasmid pBBRSTQKAB (28), creating pBBRSTQKABJ4. Correct orientation of the phaJ4 gene on the pBBRSTQKABJ4 plasmid was confirmed by restriction enzyme digest with BamHI. pBBRSTQKABJ4 was then digested with SacII to excise the unnecessary genes phaA and phaB. The linearized DNA fragment was gel-purified and ligated together at the SacII site with T4 DNA ligase, generating pBBR-C1J4SII. All restriction enzymes were purchased from New England Biolabs. All cloning transformations and plasmid preparations were performed in *E. coli* JM109.

PHA Production in *E. coli* LSBJ pBBR-C1J4SII was transformed into *E. coli* LSBJ following standard procedures (32) and grown on LB agar plates with kanamycin. Single colonies were added to 50 ml LB cultures with kanamycin and grown for 12-16 hours in a 30° C. incubator with shaking at 250 rpm. One milliliter of the overnight culture was used to inoculate 100 ml of LB with kanamycin, a fatty acid substrate at 2 g $L^{-1}$, and the surfactant Brij-35 (Fisher Scientific) at 4 g $L^{-1}$ in 500 ml baffled flasks. The flasks were incubated at 30° C. with shaking at 250 rpm for 48 hours. The fatty acids used were sodium butyrate (Alfa Aesar), sodium octanoate (Sigma), decanoic acid (Alfa Aesar), 10-undecenoic acid (SAFC), or lauric acid (Acros Organics).

Flasks to produce PHB from sodium butyrate also contained 6 g $L^{-1}$ monobasic potassium phosphate and 13.24 g $L^{-1}$ dibasic potassium phosphate. Half of the total sodium butyrate for PHB production was added after cells grew for eight hours and the second half at twenty-four hours. After incubation was complete, the cells were harvested by centrifugation at 3,716×g for 15 min. Pelleted cells were washed with 70% (v/v) ethanol, pelleted again, and then washed with Nanopure water (Barnstead). The cells were then dried via lyophilization.

Purification of PHAs

The purification of PHAs produced in *E. coli* LSBJ was based on the work published by Jiang et al. (33). Dried cells were suspended in methanol at 22 ml methanol per gram of dried cells and mixed by stirring at room temperature for five minutes. Cells were collected by centrifugation, washed with Nanopure water (Barnstead), and dried via lyophilization. PHAs were then extracted from the cells in a soxhlet extractor with 120 ml of refluxing acetone for five hours. The extract was concentrated in a rotovap and cast in a glass Petri dish.

Gas Chromatography (GC) and Gas Chromatography-Mass Spectroscopy (GC-MS) Analysis of PHAs Produced Repeating unit compositions of PHAs were determined by GC and GC-MS. For GC analysis, either dried cells (15-20 mg) or purified polymers (5-10 mg) were dissolved in 2 ml chloroform and 2 ml sulfuric acid:methanol (15:85) and heated at 100° C. for 140 minutes. After cooling the samples to room temperature, 1 ml of water was added to each sample. Samples were mixed by vortexing, and the aqueous and organic layers were separated by centrifugation at 863×g for 3 min. The organic layer containing the 3-hydroxymethyl esters was passed through a 0.45 μm polytetrafluoroethylene (PTFE) syringe filter (Restek). A total of 500 μl of the filtered sample was mixed with 500 μl of caprylic acid (1 g $L^{-1}$) in chloroform in a GC vial. Samples were then loaded by 1 μl split injection at 280° C. into a GC 2010 Gas Chromatograph with a flame ionization detector at 310° C. (Shimadzu). Samples were separated in a 30 m Rtx®-5 column (Restek, 0.25 mm id and 0.25 μmd$_f$). The heating profile for the column oven was as follows: 100° C. initial temperature, ramp to 280° C. at 8° C. $min^{-1}$, hold for 2 min, ramp to 310° C. at 20° C. $min^{-1}$, and hold for 2 min. Isolated polymers and fatty acid feedstocks were also analyzed by GC-MS, which was performed as previously described (34). Methyl/ethyl esters corresponding to PHA repeating units were determined based on retention times of known standards and resulting mass spectra when available.

Gel Permeation Chromatography (GPC) Analysis of PHAs Produced

The number-average molecular weight ($M_n$) and the weight-average molecular weight ($M_w$) were determined by GPC using a LC-20AD Liquid Chromatograph equipped with a SIL-20A auto-sampler and RID-10A refractive index detector (Shimadzu). Purified PHA samples were dissolved in chloroform at 0.7 mg/ml and passed through a 0.45 μm PTFE syringe filter. 50 μl of each sample were passed through a styrenedivinylbenzene (SDV) 8×300 mm column with 5 μm porosity (Polymer Standards Service). The column oven was maintained at 40° C. Chloroform was the mobile phase with a flow rate of 1 ml $min^{-1}$. Molecular weights were determined based on polystyrene standards as determined previously (4).

Nuclear Magnetic Resonance of PHAs Produced

For further structural analysis, 10-15 mg of purified PHAs from *E. coli* LSBJ were dissolved in 1 ml of deuterated chloroform and analyzed by gradient-enhanced-HSQC-DEPT NMR spectroscopy. All spectra were acquired at 30° C. with a Bruker AVANCE 600 spectrometer (600 MHz $^1$H frequency) equipped with a 5 mm triple resonance z-gradient probe. Data were acquired and processed in TOPSPIN v1.3 from Bruker BioSpin. The ge-HSQC-DEPT experiment had spectral widths of 4800 Hz and 25000 Hz with 2k×256 data points collected for $^1$H and $^{13}$C spectra, respectively.

Thermal Analysis of PHAs Produced

Purified polymers were kept at room temperature for at least one week prior to thermal analysis experiments. The decomposition temperatures ($T_d$) of the PHAs produced were determined by thermogravimetric analysis (TGA) using a TGA Q5000IR (TA Instruments). Approximately 10 mg of a sample were heated to 500° C. at a rate of 20° C. min$^{-1}$. The $T_d$ was taken at the temperature when sample degradation was initiated. The PHA samples were subsequently checked for glass-transition temperatures ($T_g$), melting temperatures ($T_m$), and crystallization temperatures ($T_c$) by differential scanning calorimetry (DSC) with a DSC Q200 (TA Instruments). Approximately 10 mg of polymer were heated to 200° C. at 10° C. min$^{-1}$ in a nitrogen atmosphere. Samples were then cooled to −80° C. at a rate of 5° C. min$^{-1}$ and subsequently reheated to 200° C. at 10° C. min$^{-1}$. The $T_g$ and $T_m$ were recorded during the second heating of the sample. The $T_c$ was taken during the cooling of the sample from 200° C. to −80° C.

Results

PHA Production and Composition in *E. coli* LSBJ

To develop a bacterial strain capable of producing PHA polymers with defined repeating unit composition, *E. coli* LSBJ was made from *E. coli* LS5218 by eliminating the (S)-specific enoyl-CoA hydratase fadB and its homologue fadJ on the chromosome (FIGS. 2A-B).

FIG. 2A shows a map of the *Escherichia coli* genome at the genes fadB and fadJ before and after removal of the genes. The knockout of fadB was carried out by the insertion of a chloramphenicol acetyltransferase (cat). The knockout of fadJ was carried out by insertion of a neomycin phosphotransferase and subsequent removal, leaving behind a short scar sequence. The numbers next to each map represents approximate PCR product sizes with the "check" primers in Table 2. Half arrows indicate approximate ligation sites for primers a (fadB.F.check), b fadB.R.check), x (fadJ.F.check), and y (fadJ.R.check).

FIG. 2B shows agarose electrophoresis gel of PCR products of fadB and fadJ regions of *E. coli* LS5218 and *E. coli* LSBJ. Lane 1, 1 kb ladder (New England Biolabs); Lane 2, PCR from *E. coli* LS5218 using fadB.F.check and fadB.R.check primers; Lanes 3 and 4, PCR from *E. coli* LSBJ using fadB.F.check and fadB.R.check primers; Lane 5, PCR from *E. coli* LS5218 using fadJ.F.check and fadJ.R.check primers; and Lanes 6 and 7, PCR from *E. coli* LSBJ using fadJ.F.check and fadJ.R.check primers.

*E. coli* LSBJ then produced PHAs with defined repeating unit composition from fatty acids while expressing PhaJ4 and PhaC1(STQK). The fatty acids used to produce the defined polymers were the SCL fatty acid sodium butyrate (C4) and the MCL fatty acids, sodium octanoate (C8), decanoic acid (C10), 10-undecenoic acid (C11:1, Δ10), and dodecanoic acid (C12). The repeating units of the PHAs produced were representative of the fatty acid substrate in number of carbons (Table 3). Gas chromatography (GC) initially showed each of the PHAs to be comprised entirely of repeating units equal in number of carbons as the starting fatty acid. For example, samples grown in the presence of sodium octanoate were comprised of 3-hydroxyoctanoate repeating units and no other MCL repeating units.

The only potential contaminants seen in the initial GC experiments of samples produced from the medium chain fatty acids were seen as peaks with retention times that matched 3-hydroxybutyrate (3HB). To confirm the absence or presence of 3HB in the PHAs not produced from sodium butyrate, polymer samples were analyzed by HSQC-DEPT NMR (FIGS. 3-6).

FIG. 3 shows $^1$H-$^{13}$C HSQC-DEPT NMR spectroscopy results for poly(3-hydroxyoctanoate) synthesized in *E. coli* LSBJ expressing the pBBR-C1J4SII plasmid. Purified polymer was dissolved in deuterated chloroform and checked for contaminating repeating units, specifically poly(3-hydroxybutyrate) (PHB). CH and CH$_3$ carbons are shown in black, and CH$_2$ signals are shown in gray. In addition to comparison of the spectra with previous works of NMR on PHAs, the HSQC-DEPT NMR experiments were performed to confirm the absence of 3-hydroxybutyrate (3HB) repeating units in the various MCL-PHAs. 3HB within the polymer would be differentiated from the desired MCL repeating units by looking for the chiral carbon (the third carbon) and the methyl carbon's (the fourth carbon) signals. The chiral carbon of 3HB would be slightly shielded compared to that of the MCL-PHAs (67-68 ppm vs. 70-71 ppm) in the $^{13}$C portion of the spectra. The methyl carbon would give a black signal in the area of 1.30 ppm for $^1$H and 19-20 ppm for $^{13}$C. The signals in the poly(3-hydroxyoctanoate) sample that do not correspond to signals found in other MCL-PHA samples with fully saturated side chains are believed to be residual fatty acid substrate (octanoate) that was not fully removed from extracted polymer. This sample does not show detectable PHB.

FIG. 4 shows $^1$H-$^{13}$C HSQC-DEPT NMR spectroscopy results for poly(3-hydroxydecanoate) synthesized in *E. coli* LSBJ expressing the pBBR-C1J4SII plasmid. Purified polymer was dissolved in deuterated chloroform and checked for contaminating repeating units, specifically poly(3-hydroxybutyrate). CH and CH$_3$ carbons are shown in black, and CH$_2$ signals are shown in gray. In addition to comparison of the spectra with previous works of NMR on PHAs, the HSQC-DEPT NMR experiments were performed to confirm the absence of 3-hydroxybutyrate (3HB) repeating units in the various MCL-PHAs. 3HB within the polymer would be differentiated from the desired MCL repeating units by looking for the chiral carbon (the third carbon) and the methyl carbon's (the fourth carbon) signals. The chiral carbon of 3HB would be slightly shielded compared to that of the MCL-PHAs (67-68 ppm vs. 70-71 ppm) in the $^{13}$C portion of the spectra. The methyl carbon would give a black signal in the area of 1.30 ppm for $^1$H and 19-20 ppm for $^{13}$C. This sample does not show detectable PHB.

FIG. 5 shows $^1$H-$^{13}$C HSQC-DEPT NMR spectroscopy results for poly(3-hydroxy-10-undecenoate) synthesized in *E. coli* LSBJ expressing the pBBR-C1J4SII plasmid. Purified polymer was dissolved in deuterated chloroform and checked for contaminating repeating units, specifically poly (3-hydroxybutyrate). CH and CH$_3$ carbons are shown in black, and CH$_2$ signals are shown in gray. In addition to comparison of the spectra with previous works of NMR on PHAs, the HSQC-DEPT NMR experiments were performed to confirm the absence of 3-hydroxybutyrate (3HB) repeating units in the various MCL-PHAs. 3HB within the polymer would be differentiated from the desired MCL repeating units by looking for the chiral carbon (the third carbon) and the methyl carbon's (the fourth carbon) signals. The chiral carbon of 3HB would be slightly shielded compared to that of the MCL-PHAs (67-68 ppm vs. 70-71 ppm) in the $^{13}$C portion of the spectra. The methyl carbon would give a black signal in the area of 1.30 ppm for $^1$H and 19-20 ppm for $^{13}$C. The fatty acid substrates were found to have detectable amounts of different fatty acids in GC-MS experiments. This may have been the cause for detectable amounts of repeating units (GC-MS) in PHAs not equal in size to the starting substrate. The fatty acid substrate for production of poly(3-hyroxy-10-undecenoate) (PHUn), 10-undecenoic acid, was listed as 95% pure by the manufacturer (SAFC). The contaminating materials likely contain fully saturated fatty acids. These fully saturated fatty acids would also be incorporated into PHAs synthesized by this system. These potential contaminants can be seen in the $^1$H spectrum of the PHUn sample at ~0.8 ppm. This is the same chemical shift seen for the terminal methyl groups of the polymers containing fully saturated side chains in the repeating units (FIGS. 3, 4 and 6). This sample does not show detectable PHB.

the substrates were also found to have detectable amounts of contaminating fatty acids. Fully saturated fatty acids were present in large enough quantities in the 10-undecenoic acid substrate that the subsequent incorporation of the contaminants in the PHAs could be detected in HSQC-DEPT NMR of the poly(3-hydroxy-10-undecenoate) (PHUn) sample (FIG. 5).

PHB was also synthesized using this system. Sodium butyrate was added to the cell media to generate the SCL PHA. Table 3 shows that PHB was accumulated at 7.81% of the cell dry weight in *E. coli* LSBJ. The PHB synthesized was not in large enough quantities for further purification and testing. After successful synthesis of PHB in this system, it is inferred that all repeating units can be synthesized and controlled from four and up to twelve carbons in length.

TABLE 3

PHA yield and composition from single fatty acid substrates

| | | | PHA Composition (mol %)** | | | | | | | |
|---|---|---|---|---|---|---|---|---|---|---|
| PHA Substrate | CDW (g L$^{-1}$) | PHA (wt %) | 3HB (C4) | 3HHx (C6) | 3HO (C8) | 3HN (C9) | 3HD (C10) | 3HUn (C11) | 3HDD (C12) | 3HTD (C13) |
| Sodium Butyrate | 1.29 ± 0.03 | 7.81 ± 0.21 | 100 | 0 | 0 | 0 | 0 | 0 | 0 | 0 |
| Sodium Octanoate | 0.86 ± 0.02 | 47.3 ± 5.0 | 0 | 0 | ≤100* | 0 | trace | 0 | trace | 0 |
| Decanoic Acid | 1.03 ± 0.01 | 25.7 ± 0.9 | 0 | 0 | trace | 0 | ≤100* | 0 | trace | 0 |
| 10-Undecenoic Acid | 1.07 ± 0.03 | 41.0 ± 8.0 | 0 | 0 | 0 | 0 | 0 | ≤100* | 0 | trace |
| Dodecanoic Acid | 1.03 ± 0.05 | 28.6 ± 8.0 | 0 | 0 | 0 | 0 | trace | 0 | ≤100* | 0 |

*Values shown determined by GC. GC-MS data showed qualitatively detectable amounts (labeled "trace") of other repeating units.
**3HB, 3-hydroxybutyrate; 3HHx, 3-hydroxyhexanoate; 3HO, 3-hydroxyoctanoate; 3HN, 3-hydroxynonanoate; 3HD, 3-hydroxydecanoate; 3HUn, 3-hydroxy-10-undecenoate; 3HDD, 3-hydroxydodecanoate; 3HTD, 3-hydroxytridecanoate.
All values are averages of triplicate experiments plus or minus the standard deviation about those averages.

FIG. 6 shows $^1$H-$^{13}$C HSQC-DEPT NMR spectroscopy results for poly(3-hydroxydodecanoate) synthesized in *E. coli* LSBJ expressing the pBBR-C1J4SII plasmid. Purified polymer was dissolved in deuterated chloroform and checked for contaminating repeating units, specifically poly(3-hydroxybutyrate). CH and CH$_3$ carbons are shown in black, and CH$_2$ signals are shown in gray. In addition to comparison of the spectra with previous works of NMR on PHAs, the HSQC-DEPT NMR experiments were performed to confirm the absence of 3-hydroxybutyrate (3HB) repeating units in the various MCL-PHAs. 3HB within the polymer would be differentiated from the desired MCL repeating units by looking for the chiral carbon (the third carbon) and the methyl carbon's (the fourth carbon) signals. The chiral carbon of 3HB would be slightly shielded compared to that of the MCL-PHAs (67-68 ppm vs. 70-71 ppm) in the $^{13}$C portion of the spectra. The methyl carbon would give a black signal in the area of 1.30 ppm for $^1$H and 19-20 ppm for $^{13}$C. This sample does not show detectable PHB.

Chemical shifts were compared to previous works utilizing NMR to analyze PHAs (28,35,36). Chemical shifts corresponding to the 3HB repeating unit were not observed in the NMR experiments.

Extracted PHAs were also analyzed by gas chromatography-mass spectroscopy (GC-MS), and MCL repeating units not equal in carbon length to the starting fatty acid were found. However, these minor fractions were in amounts lower than the GC detection limit and only qualitatively detected with GC-MS (Table 3). The carbon sources for the PHAs (i.e. fatty acids) were also analyzed by GC-MS, and Physical and Thermal Characterization of MCL PHAs Produced in *E. coli* LSBJ To examine the physical properties of the PHA polymers produced, the weight average molecular weights ($M_w$), number average molecular weights ($M_n$), and polydispersities ($M_w/M_n$) were determined by gel permeation chromatography (GPC) (Table 4). The decomposition temperatures ($T_d$) for each of the MCL PHAs produced were determined by thermogravimetric analysis (TGA); and the glass-transition temperatures ($T_g$), melting temperatures ($T_m$), and crystallization temperatures ($T_c$) were determined by differential scanning calorimetry (DSC). These results are shown in Table 4. The DSC and TGA scans are displayed in FIGS. 7A-B.

TABLE 4

PHA physical properties

| | Molecular Weight | | | $T_g$ | $T_m$ | $T_c$ | $T_d$ |
|---|---|---|---|---|---|---|---|
| PHA* | Mw (kDa) | Mn (kDa) | Mw/Mn | (° C.) | (° C.) | (° C.) | (° C.) |
| PHO | 224 | 104 | 2.2 | −42.1 | ND | ND | 236.8 |
| PHD | 270 | 111 | 2.4 | −39.8 | 57.7 | 23.1 | 245.3 |
| PHUn | 233 | 76 | 3.1 | −61.6 | ND | ND | 244.4 |
| PHDD | 65 | 40 | 1.6 | ND | 71.9 | 41.3 | 242.2 |

*PHO, poly(3-hydroxyoctanoate); PHD, poly(3-hydroxydecanoate); PHUn, poly(3-hydroxy-10-undecenoate); PHDD, poly(3-hydroxydodecanoate), ND, not detected.

FIGS. 7A-B show thermal analysis of purified medium-chain-length poly(3-hydroxyalkanoates). Differential scanning calorimetry scans are shown in (A), and thermogravimetric analysis results are shown in (B) for purified poly(3-hydroxyoctanoate) (PHO), poly(3-hydroxydecanoate) (PHD), poly(3-hydroxy-10-undecenoate) (PHun), and poly(3-hydroxydodecanoate) (PHDD).

Discussion

The *E. coli* LSBJ strain developed here in combination with the PHA production plasmid pBBR-C1J4SII allows strict control of repeating unit composition of PHAs for both MCL and SCL PHAs. The desired PHAs can be synthesized based simply on selecting a fatty acid substrate of equal carbon length. As shown in Table 3, PHAs were synthesized in sizes ranging from four to twelve carbons. Because of the native enoyl-CoA hydratase knockouts, the resulting PHAs were near homopolymers based on GC, GC-MS, and NMR analysis. GC-MS analysis found detectable amounts of repeating units different in carbon lengths than the starting fatty acid substrate, but this is likely due to impurities of the substrates and media (Table 3 and FIG. 5).

*E. coli* LSBJ is particularly useful for MCL PHA production from fatty acids. The parent strain, *E. coli* LS5218, is known to have increased uptake and metabolism for a broad range of fatty acids without the need for transcriptional induction of the appropriate fad genes by FadR (17,18). The PhaJ4 and PhaC1(STQK) introduced to synthesize the PHAs have high activity towards MCL substrates. This allowed for the strain to generate MCL PHAs at 25% cell dry weight or greater (Table 3).

Although the system created here was designed with MCL PHA repeating unit control in mind, control can also be extended to SCL PHAs. The advantages of *E. coli* LSBJ extend to SCL sized fatty acids, and thus PHB was synthesized from sodium butyrate. This was expected as the uptake for shorter fatty acids does not need to be induced in this strain (18), and the PhaJ4 and PhaC1(STQK) enzymes selected for PHA synthesis have reported or inferred activity for four carbon substrates (21,22,26). The PHB yield was much lower than the MCL PHAs. This could be because of enzyme substrate specificity favoring MCL substrates.

This system offers the broadest range of repeating unit control of PHAs in a single organism. Other work has been reported to control repeating unit composition in *Pseudomonas putida* KT2442 (8). The polymer yields here were lower compared to the *Pseudomonas* system developed by Wang et al., but the *Pseudomonas* system was unable to synthesize homopolymers with repeating units greater than seven carbons. The *E. coli* LSBJ system developed in this study was shown to maintain repeating unit control up to and including repeating units of twelve carbons. The size limits for repeating unit control of this system have not been determined as of this writing.

The thermal properties of the MCL PHAs produced here have similarities and differences when compared to other works that have produced MCL PHA homopolymers (8,9). Poly(3-hydroxyoctanoate) (PHO), for example, showed a $T_g$ of −42.1° C., which is lower than other works producing polymers of ≥98 mol % PHO (8,9). No melting temperature was seen here for PHO, which is not the case for reports of the other studies with ≥98 mol % PHO polymers (8,9). However, the other studies report very different melting temperatures. The study by Wang et al. reports a melting temperature of 66.06° C., but a melting endothermic peak cannot be seen on the DSC curve (8). The study by Rai et al. reported a range of melting temperatures between 39° C. and 50° C., but DSC curves are not presented (9). DSC curves for this work can be found in the FIGS. 7A-B. There are many differences in these works for producing, purifying, and characterizing the polymers, which may account for the lack of consistency in reported thermal properties of PHO homopolymers.

Another MCL PHA homopolymer that was produced in this example was poly(3-hydroxydecanoate) (PHD) (7). Both the work presented here and the work by Liu et al. report glass transitions between −37° C. and −40° C. The previously produced PHD homopolymer had a reported melting temperature of 72.2° C. compared to the melting temperature of 57.7° C. for the PHD produced in this work. Once again, differences in synthesis, purification, and characterization methods could play a role in the differences in reported thermal properties.

Melting, crystallization, and glass transition temperatures can be predicted for MCL PHA homopolymers based on repeating unit size in PHAs. The $T_g$ for these polymers may decrease with increasing side chain length as has been suggested by another work developing MCL PHA homopolymers (8). If this is true, the glass-transition temperature for poly(3-hydroxydodecanoate) (PHDD) may be near or below the −80° C. minimum of the DSC scans performed. There was no definitive trend in the degradation temperatures of all the polymers tested (Table 4 and FIGS. 7A-B). The thermal properties and trends of polymers here did not coincide with the properties of the polymers reported by Wang et al. (8). However, this could be the result of differing polymer purification, polymer storage conditions, molecular weights, and/or experimental conditions for DSC and TGA.

The molecular weights varied for the MCL PHAs, and the polydispersities determined by GPC ranged from 1.6 to 3.1 (Table 4). The molecular weights ($M_n$) were varied with PHD and PHO having noticeably larger molecular weights than PHUn and PHDD. The PHO molecular weight ($M_n$) and polydispersity are comparable to previous work with this polymer (9). The PHD molecular weight ($M_n$) is more than twice as small as a previous work producing PHD homopolymer, and the polydispersity is greater in this example (7). The PHUn and PHDD homopolymers have not been synthesized bacterially prior to this work.

Comparison of polymer molecular weights and polydispersities from this example to other works is difficult due to the differences in bacterial production. Other works have relied on native *Pseudomonas* PHA synthesis enzymes. The polymers in this example were made in *E. coli* expressing an enzyme with naturally broad substrate specificity (PhaJ4) and an enzyme with engineered broad substrate specificity [PhaC1(STQK)]. The substrate specificities of the PHA synthesis enzymes, particularly the PHA synthase, could have a significant effect on the molecular weights of the polymers. Some in vitro characterization of the substrate specificity of the PhaC1(STQK) synthase used in this example is available but limited to substrates with four to ten carbons (37). Because the relationship of substrate specificity to molecular weight of the polymer produced by PHA synthase enzymes is not completely defined, there is not sufficient information to draw conclusions as to why there are differences in the molecular weights of the PHA polymers produced in this example. However, the differences in the substrate specificity of engineered and native PHA synthases may be responsible for the differences in the molecular weights of polymers.

The strain *E. coli* LSBJ was developed to allow for repeating unit control in PHA biosynthesis. Knockouts of the genes fadB and fadJ created a dam in the β-oxidation pathway (FIG. 1). Instead of being degraded, fatty acid substrates were converted to PHAs by PhaJ4 and PhaC1 (STQK). This allowed for control of repeating unit composition simply by selecting the fatty acid that matches the desired repeating unit in carbon length. This strain successfully demonstrated repeating unit control in PHAs with repeating units of four, eight, ten, eleven, and twelve carbons. This represents the first bacterial strain to achieve such diversity in repeating unit control of PHAs.

REFERENCES

1. Lu J., Tappel R. C., and Nomura C. T.: Mini-review: Biosynthesis of poly(hydroxyalkanoates). Pol. Rev., 49, 226-248 (2009).
2. Sudesh, K., Abe, H., and Doi, Y.: Synthesis, structure and properties of polyhydroxyalkanoates: Biological polyesters. Prog. Polym. Sci., 25, 1503-1555 (2000).
3. Abe, H. and Doi, Y.: Side-chain effect of second monomer units on crystalline morphology, thermal properties, and enzymatic degradability for random copolyesters of (R)-3-hydroxybutyric acid with (R)-3-hydroxyalkanoic acids. Biomacromolecules, 3, 133-138 (2002).
4. Zhu, C., Nomura, C. T., Perrotta, J. A., Stipanovic, A. J., and Nakas, J. P.: Production and characterization of poly-3-hydroxybutyrate from biodiesel-glycerol by *Burkholderia cepacia* ATCC 17759. Biotechnol. Prog., 26, 424-430 (2010).
5. Steinbüchel, A., Valentin, H. E., and Schönebaum, A.: Application of recombinant gene technology for production of polyhydroxyalkanoic acids: Biosynthesis of poly (4-hydroxybutyric acid) homopolyester. J. Polym. Environ., 2, 67-74 (1994).
6. Wang, H.-H., Li, X.-T., and Chen, G.-Q.: Production and characterization of homopolymer polyhydroxyheptanoate (P3HHp) by a fadBA knockout mutant *Pseudomonas putida* KTOY06 derived from *P. putida* KT2442. Process Biochem., 44, 106-111 (2009).
7. Liu, Q., Luo, G., Zhou, X. R., and Chen, G.-Q.: Biosynthesis of poly(3-hydroxydecanoate) and 3-hydroxydodecanoate dominating polyhydroxyalkanoates by β-oxidation pathway inhibited *Pseudomonas putida*. Metab. Eng., 13, 11-17 (2011).
8. Wang, H.-H., Zhou, X-R., Liu, Q., and Chen, G.-Q.: Biosynthesis of polyhydroxyalkanoate homopolymers by *Pseudomonas putida*. Appl. Microbiol. Biotechnol., 89, 1497-1507 (2011).
9. Rai, R., Yunos, D. M., Boccaccini, A. R., Knowles, J. C., Barker, I. A., Howdle, S. M., Tredwell, G. D., Keshavarz, T., and Roy, I.: Poly-3-hydroxyoctanoate P(3HO), a Medium Chain Length Polyhydroxyalkanoate Homopolymer from *Pseudomonas mendocina*. Biomacromolecules, 12, 2126-2136 (2011).
10. Rai, R., Keshavarz, T., Roether, J. A., Boccaccini, A. R., and Roy, I.: Medium chain length polyhydroxyalkanoates, promising new biomedical materials for the future. Mat. Sci. Eng. R., 72, 29-47 (2011).
11. Campbell, J. W., Morgan-Kiss, R. M., and Cronan Jr., J. E.: A new *Escherichia coli* metabolic competency: Growth on fatty acids by a novel anaerobic β-oxidation pathway. Mol. Microbiol., 47, 793-805 (2003).
12. Rhie, H. G. and Dennis, D.: Role of fadR and atoC(Con) mutations in poly(3-hydroxybutyrate-Co-3-hydroxyvalerate) synthesis in recombinant pha+ *Escherichia coli*. Appl. Environ. Microbiol., 61, 2487-2492 (1995).
13. Ren, Q., Sierro, N., Kellerhals, M., Kessler, B., and Witholt, B.: Properties of engineered poly-3-hydroxyalkanoates produced in recombinant *Escherichia coli* strains. Appl. Environ. Microbiol., 66, 1311-1320 (2000).
14. Fiedler, S., Steinbüchel, A., and Rehm, B. H.: The role of the fatty acid β-oxidation multienzyme complex from *Pseudomonas oleovorans* in polyhydroxyalkanoate biosynthesis: Molecular characterization of the fadBA operon from *P. oleovorans* and of the enoyl-CoA hydratase genes phaJ from *P. oleovorans* and *Pseudomonas putida*. Arch. Microbiol., 178, 149-160 (2002).
15. Snell, K. D., Feng, F., Zhong, L., Martin, D., and Madison, L. L.: YfcX enables medium-chain-length poly (3-hydroxyalkanoate) formation from fatty acids in recombinant *Escherichia coli* fadB strains. J. Bacteriol., 184, 5696-5705 (2002).
16. Park, S. J., Park, J. P., Lee, S. Y., and Doi, Y.: Enrichment of specific monomer in medium-chain-length poly(3-hydroxyalkanoates) by amplification of fadD and fadE genes in recombinant *Escherichia coli*. Enzyme Microb. Technol., 33, 62-70 (2003).
17. DiRusso, C. C., Heimert, T. L., and Metzger, A. K.: Characterization of FadR, a global transcriptional regulator of fatty acid metabolism in *Escherichia coli*. Interaction with the fadB promoter is prevented by long chain fatty acyl coenzyme As. J. Biol. Chem., 267, 8685-8691 (1992).
18. Spratt, S. K., Ginsburgh, C. L., and Nunn, W. D.: Isolation and genetic characterization of *Escherichia coli* mutants defective in propionate metabolism. J. Bacteriol., 146, 1166-1169 (1981).
19. Pauli, G. and Overath, P.: ato Operon: a highly inducible system for acetoacetate and butyrate degradation in *Escherichia coli*. Eur. J. Biochem., 29, 553-562 (1972).
20. Jenkins, L. S. and Nunn, W. D.: Genetic and molecular characterization of the genes involved in short-chain fatty acid degradation in *Escherichia coli*: The ato system. J. Bacteriol., 169, 42-52 (1987).
21. Tsuge, T., Taguchi, K., Taguchi, S., and Doi, Y.: Molecular characterization and properties of (R)-specific enoyl-CoA hydratases from *Pseudomonas aeruginosa*: Metabolic tools for synthesis of polyhydroxyalkanoates via fatty acid β-oxidation. Int. J. Biol. Macromol., 31, 195-205 (2003).
22. Sato, S., Kanazawa, H., and Tsuge, T.: Expression and characterization of (R)-specific enoyl coenzyme A hydratases making a channeling route to polyhydroxyalkanoate biosynthesis in *Pseudomonas putida*. Appl. Microbiol. Biotechnol., 90, 951-959 (2011).
23. Fukui, T., Yokomizo, S., Kobayashi, G., and Doi, Y.: Co-expression of polyhydroxyalkanoate synthase and (R)-enoyl-CoA hydratase genes of *Aeromonas caviae* establishes copolyester biosynthesis pathway in *Escherichia coli*. FEMS Microbiol. Lett., 170, 69-75 (1999).
24. Tsuge, T., Fukui, T., Matsusaki, H., Taguchi, S., Kobayashi, G., Ishizaki, A., and Doi, Y.: Molecular cloning of two (R)-specific enoyl-CoA hydratase genes from *Pseudomonas aeruginosa* and their use for polyhydroxyalkanoate synthesis. FEMS Microbiol. Lett., 184, 193-198 (2000).
25. Budde, C. F., Riedel, S. L., Willis, L. B., Rha, C., and Sinskey, A. J.: Production of poly(3-hydroxybutyrate-co-3-hydroxyhexanoate) from plant oil by engineered *Ralstonia eutropha* strains. Appl. Environ. Microbiol., 77, 2847-2854 (2011).
26. Takase, K., Taguchi, S., and Doi, Y.: Enhanced synthesis of poly(3-hydroxybutyrate) in recombinant *Escherichia coli* by means of error-prone PCR mutagenesis, saturation mutagenesis, and in vitro recombination of the type II polyhydroxyalkanoate synthase gene. J. Biochem., 133, 139-145 (2003).

27. Matsusaki, H., Manji, S., Taguchi, K., Kato, M., Fukui, T., and Doi, Y.: Cloning and molecular analysis of the poly(3-hydroxybutyrate) and poly(3-hydroxybutyrate-co-3-hydroxyalkanoate) biosynthesis genes in *Pseudomonas* sp. strain 61-3. J. Bacteriol., 180, 6459-6467 (1998).
28. Nomura, C. T., Tanaka, T., Gan, Z., Kuwabara, K., Abe, H., Takase, K., Taguchi, K., and Doi, Y.: Effective enhancement of short-chain-length—Medium-chain-length polyhydroxyalkanoate copolymer production by coexpression of genetically engineered 3-ketoacyl-acyl-carrier-protein synthase III (fabH) and polyhydroxyalkanoate synthesis genes. Biomacromolecules, 5, 1457-1464 (2004).
29. Nomura, C. T., Tanaka, T., Eguen, T. E., Appah, A. S., Matsumoto, K., Taguchi, S., Ortiz, C. L., and Doi, Y.: FabG mediates polyhydroxyalkanoate production from both related and nonrelated carbon sources in recombinant *Escherichia coli* LS5218. Biotechnol. Prog., 24, 342-351 (2008).
30. Datsenko, K. A. and Wanner, B. L.: One-step inactivation of chromosomal genes in *Escherichia coli* K-12 using PCR products. Proc. Natl. Acad. Sci. U.S.A., 97, 6640-6645 (2000).
31. Wang, Q. and Nomura, C. T.: Monitoring differences in gene expression levels and polyhydroxyalkanoate (PHA) production in *Pseudomonas putida* KT2440 grown on different carbon sources. J. Biosci. Bioeng., 110, 653-659 (2010).
32. Sambrook, J. J. and Russell, D. W.: Molecular cloning: a laboratory manual. Cold Spring Harbor Laboratory Press, Cold Spring Harbor, N.Y. (2001).
33. Jiang, X., Ramsay, J. A., and Ramsay, B. A.: Acetone extraction of mcl-PHA from *Pseudomonas putida* KT2440. J. Microbiol. Methods, 67, 212-219 (2006).
34. Arai, Y., Nakashita, H., Suzuki, Y., Kobayashi, Y., Shimizu, T., Yasuda, M., Doi, Y., and Yamaguchi, I.: Synthesis of a novel class of polyhydroxyalkanoates in *Arabidopsis peroxisomes*, and their use in monitoring short-chain-length intermediates of β-oxidation. Plant Cell Physiol., 43, 555-562 (2002).
35. Matsusaki, H., Abe, H., Taguchi, K., Fukui, T., and Doi, Y.: Biosynthesis of poly(3-hydroxybutyrate-co-3-hydroxyalkanoates) by recombinant bacteria expressing the PHA synthase gene phaC1 from *Pseudomonas* sp. 61-3. Appl. Microbiol. Biotechnol., 53, 401-409 (2000).
36. Sparks, J. and Scholz, C.: Synthesis and characterization of a cationic Poly(β-hydroxyalkanoate). Biomacromolecules, 9, 2091-2096 (2008).
37. Matsumoto, K., Takase, K., Aoki, E., Doi, Y., and Taguchi, S.: Synergistic effects of Glu130Asp substitution in the type II polyhydroxyalkanoate (PHA) synthase: Enhancement of PHA production and alteration of polymer molecular weight. Biomacromolecules, 6, 99-104 (2005).

6.2 Example 2

Production of Specified Short-Chain-Length and Medium-Chain-Length Single Repeating Units in poly[(R)-3-hydroxyalkanoate] Copolymers Synthesized in *Escherichia coli* Using Fatty Acid Substrates This example describes extension of the work described in Example 1. The production of specified short-chain-length and medium-chain-length single repeating units in poly[(R)-3-hydroxyalkanoates] were synthesized in *E. coli* using fatty acid substrates. This example also provides an overview and summary of the results obtained in Example 1.

Introduction

Poly(3-hydroxyalkanoates) (PHAs) are biodegradable plastics and carbon storage materials that are synthesized by a myriad of microorganisms. PHAs are divided into groups based on repeating unit size. PHAs with repeating units of three to five carbons in length are short-chain-length (SCL) PHAs, and PHAs with repeating units of six to fourteen carbons in length are medium-chain-length (MCL) PHAs. Differences in repeating unit composition influence the physical properties of PHAs. SCL PHA homopolymers such as poly-3-hydroxybutyrate (PHB) have been previously produced, but methods to control the repeating unit composition of the MCL PHAs have been limited. Previous attempts to control MCL PHA synthesis in native and recombinant PHA-producing organisms have resulted in narrow ranges of repeating unit control (6-9). Typically, control is limited to only a couple of repeating units within one organism (6,7,9) or control is lost once the number of carbons in the repeating unit exceeds seven (8).

In this example, *Escherichia coli* LS5218 was engineered to develop a PHA-production system capable of synthesizing PHAs with repeating unit compositions based solely on the carbon chain length of fatty acid substrates fed to the strain. PHA synthesis control is demonstrated for repeating units from four and up to twelve carbons long, spanning both SCL and MCL PHAs.

Gaining control over such a broad range of repeating units in PHAs is useful for a number of applications for which PHAs are being considered, particularly for the production of MCL PHAs being analyzed for medical uses. Various SCL-co-MCL PHA copolymers have been tested for heart valve engineering, nerve regeneration, skin regeneration, drug delivery and more (10). These applications require specific physical properties that can be attained with the proper ratio of repeating units within PHAs. A system that allows for selection of repeating unit sizes and ratios aids in synthesis of PHAs with medically relevant physical properties.

This example demonstrates an engineered microbial system capable of controlling the molecular composition of PHA polymers over a broad range of repeating unit sizes including MCL and SCL PHAs. PHAs with homogenous repeating units were synthesized and control over repeating unit size selection was demonstrated.

Deletions of enzymes involved in fatty acid degradation and expression of PHA synthesis enzymes with broad substrate specificities allow for controlled PHA synthesis utilizing fatty acid substrates equal in length to the desired repeating unit. The fatty acid starting materials enter the β-oxidation pathway but are stopped at the enoyl-CoA intermediate (FIG. 1). Instead of proceeding through β-oxidation and degrading, the enoyl-CoA intermediate accumulates due to elimination of the (S)-specific enoyl-CoA hydratase fadB and its homologue fadJ (formerly yfcX). Deletion of these genes from *E. coli* eliminates the ability of the organism to grow on fatty acids (11). Numerous studies have been carried out that utilize β-oxidation mutations to promote PHA synthesis in vivo (12-16). However, no work has been presented with mutations of both fadB and fadJ for the production of PHAs comprised of specific repeating units as displayed here. Since the β-oxidation pathway is stopped prior to degradation of the fatty acid, any fatty acids that enter the pathway are converted to PHA substrates equal in length as the starting fatty acid. The enoyl-CoA intermediates were converted to (R)-3-hydroxyacyl-CoA by the (R)-specific enoyl-CoA hydratase (PhaJ4) and polymerized by a PHA synthase [PhaC1(STQK)].

E. coli LS5218 was chosen as the parental strain for generating this system because of its abilities to uptake and degrade a broad range of fatty acids. Normally, the E. coli genes responsible for uptake and degradation of medium to long-chain fatty acids via the β-oxidation pathway require induction by fatty acids of at least fourteen carbons in length (17). E. coli LS5218 has a mutated fadR gene, which leads to constitutive expression of the fad genes encoding the enzymes for β-oxidation (12,18). E. coli LS5218 also has an atoC(Con) mutation allowing for constitutive expression of AtoC, a positive regulator of the ato operon, which is responsible for uptake of short chain fatty acids for β-oxidation (19,20). These mutations allow LS5218 to readily metabolize short to very long chain fatty acids without induction.

To ensure repeating unit control of PHA synthesis could be ascertained over a large range of repeating unit lengths, the (R)-specific enoyl-CoA hydratase and PHA synthase preferably have wide substrate specificities. Therefore, PhaJ4 from *Pseudomonas putida* KT2440 was selected for converting the enoyl-CoA intermediate of β-oxidation to (R)-3-hydroxyacyl-CoA. PhaJ4 from *P. putida* KT2440 has 78% amino acid identity to PhaJ4 from *Pseudomonas aeruginosa*, which was reported to have relatively high activity for enoyl-CoA substrates ranging in size from four to twelve carbons (21,22). (R)-specific enoyl-CoA hydratases have been used numerous times to synthesize PHAs (14, 21-25),but none of the studies demonstrated the ability to control PHA repeating unit composition as the system generated here.

The PHA synthase used in this work was PhaC1(STQK), an engineered PHA synthase derived from the native *Pseudomonas* sp. 61-3 PHA synthase (26). The wild type PHA synthase was unique in its ability to incorporate both SCL and MCL units in PHAs (27) and was engineered to increase its ability to incorporate SCL units. This PHA synthase has been used successfully to produce PHAs containing repeat units of four to twelve carbons in length(28, 29), making it a suitable partner for the PhaJ4 enzyme for synthesizing a wide range of PHAs with varying side chain lengths.

The unique E. coli repeating unit control system developed in this study allows for unprecedented control of PHA repeating unit composition within one bacterial strain. The desired repeating unit(s) can be selected for incorporation into PHAs simply by selecting the fatty acid substrate of equal carbon length. This system has several advantages over previous attempts at producing PHA homopolymers. The E. coli strain made in this study is capable of utilizing a wide range of fatty acids, without induction, and converting them to PHA polymers with uniform repeating unit composition. Another advantage is that E. coli is not a native producer of PHAs and lacks the enzymes to degrade the PHAs once synthesized. This study demonstrates, for the first time within one biological system, PHA production with the ability to tightly control repeating unit composition for repeating units from four and up to twelve carbons.

Background

In 2010, 310 million tons of plastics were generated within the United States alone (30). The vast majority of these materials are made from non-renewable fossil fuels and are neither biodegradable nor recovered for recycling at a high rate (8.2% in 2010)(30). Biodegradable plastics such as PHAs offer the potential for relief from the numerous environmental problems associated with the production and disposal of this class of material (1,2,31,32). PHAs are produced in a myriad of microorganisms (1), exhibit great structural diversity in terms of the chemical compositions of the possible repeating units(1), and undergo facile degradation in numerous settings (33-35). In addition to their use as replacements for petroleum-based plastics for bulk commodity uses, PHAs are under consideration for several more specialized applications, including the production of enantiomerically pure materials for use in the synthesis of other valuable molecules (36) and numerous medical applications using PHAs as substrates (10, 37-39). As the number of applications and the demand for biorenewable plastics grow and become more specialized, it becomes increasingly critical that methods be established that permit greater control over the physical properties of such biologically synthesized plastics (including PHAs).

The physical properties of PHAs are greatly influenced by the repeating unit composition of the polymer. Each repeating unit of a natively-produced PHA polymer can typically vary in size from four to fourteen carbons. PHA copolymers can consist of random mixtures of repeating units of different sizes, where the composition depends upon the carbon source, the growth conditions, and the organism chosen for producing the PHAs (1,2,10). Based upon the size of the repeating unit, PHAs are generally referred to as either SCL or MCL when the repeat unit contains either three to five carbon atoms or six to fourteen carbon atoms, respectively. The physical properties of PHA polymers comprised of various assortments of these repeating units can continuously span the range from those for SCL to MCL PHAs depending upon the mole ratio composition (2,40). Since the repeating unit composition of PHAs greatly influences the overall material properties of these polymers, one of the critical challenges facing the use of PHAs in applications is establishment of the ability to consistently and reproducibly produce PHA polymers or copolymers with prescribed repeating unit compositions.

There have been multiple reports to the effect that PHAs can be produced with varying compositions and that suggest ways to control for these differing repeating unit combinations and content (40-43). For example, in contrast to the common in vivo bacterial system described here, in vitro polymerization using differing amounts of lactones has been utilized to control repeating unit composition in PHA copolymers (40). These chemical syntheses products, however, have lower molecular weights and were not enantiometrically pure, which limits the biodegradability of the polymers and complicates characterization (40). Incorporation of both (R)-3-hydroxyhexanoate (3HHX) and lactic acid (LA) has been achieved at different levels by mutating specific amino acids in PHA synthases and represents important work for furthering the understanding of how PHA synthases incorporate different repeating units in PHAs (41,42).

Recently, a recombinant E. coli system was developed that produced poly(3-hydroxypropionate-co-4-hydroxybutyrate) from 1,3-propanediol and 1,4-butanediol (43). The repeating unit compositions were controlled via substrate ratio variation, but the study was limited to two repeating unit types. Additionally, there are reports showing bacterial systems that produce PHA polymers with defined compositions of PHAs with only one repeating unit (4-8). These have potential use in generating copolymers with controlled repeating unit compositions, but these systems would provide control that extends only to narrow ranges of repeating units and would thus have limited potential for controlled copolymer biosynthesis. In this report, we describe a system that can incorporate the broadest array of repeating units to date (spanning SCL and MCL PHAs) and produce PHA copolymers with precisely defined mol % compositions of specific repeating units.

Example 1 describes the development of *Escherichia coli* LSBJ to control the repeating unit composition of PHAs over a broad range of repeating unit sizes (44). *E. coli* LSBJ was derived from *E. coli* LS5218, whose mutations in the regulation of fatty acid uptake and degradation genes allow constitutive expression of genes responsible for fatty acid utilization in *E. coli* (12,18,20). It was shown that the repeating unit size could be selected between four to twelve carbons by simply using a fatty acid substrate with an equal number of carbons (FIG. 1). This was accomplished in part by way of removal of the gene for the (S)-specific enoyl-CoA hydratase (fadB) and its homologue (fadJ), thereby eliminating the ability of the bacteria to oxidize fatty acids beyond enoyl-CoA (11,15). PHAs were then synthesized from the enoyl-CoA intermediate of β-oxidation by the transgenically expressed (R)-specific enoyl-CoA hydratase (PhaJ4) and PHA synthase (PhaC1(STQK)), each of which contain broad substrate specificities (21,22,26).

With the demonstration that this system can dictate the synthesis of a large range of PHA repeating units individually, the next step in the present example was to characterize *E. coli* LSBJ as a vehicle for the production of PHA copolymers with controlled repeating unit compositions. The present example demonstrates the ability of *E. coli* LSBJ to produce PHA copolymers with specific, prescribed, repeating unit compositions. Two or more (i.e., a plurality) of fatty acid substrates can be co-fed to the bacteria at varying ratios for incorporation into a PHA copolymer with a desired or controlled repeating unit composition. In this example, two different types of fatty acid substrate were co-fed to the bacteria at varying ratios for incorporation into the PHA copolymer. The PHA polymers produced in this study allowed not only for the calibration of the repeating unit compositions in PHAs but also for the selection of specific sets of physical properties within the range of the copolymers that were produced.

Materials and Methods
Media and Cultivation

A list of strains and plasmids used in this study is shown in Table 1. All *E. coli* strains were grown on Lennox Broth purchased from Difco (LB; composition per liter: 10 g tryptone, 5 g yeast extract, and 5 g sodium chloride) at 30° C. and 250 rpm on a rotary shaker. The following antibiotics were added as appropriate to growth media: kanamycin at 50 µg ml$^{-1}$, ampicillin at 100 µg ml$^{-1}$, and chloramphenicol at 30 µg ml$^{-1}$. The fatty acids dodecanoic acid (Acros Organics), decanoic acid (Alfa Aesar), sodium octanoate (Sigma-Aldrich), and sodium butyrate (Alfa Aesar) were used as substrates for PHA biosynthesis. Monobasic and dibasic potassium phosphates (BDH) were added to flasks containing sodium butyrate at a concentration of 6.0 g L$^{-1}$ and 13.24 g L$^{-1}$, respectively as a buffer. To aid dissolution of fatty acids, the surfactant Brij-35 (Fisher Scientific) was added to flasks that contained only MCL-sized fatty acid substrates (that is, dodecanoic acid, decanoic acid, and sodium octanoate) at 4.0 g L$^{-1}$. ACS reagent/HPLC-grade methanol, acetone, and chloroform were used in sample pretreatment and extraction of polymers from bacterial cells. Any further additions to the media or culture conditions were as described below.

Gene Knockouts in *E. coli* LS5218

The method for chromosomal gene inactivation in *E. coli* developed by Datsenko and Wanner (45) was used to inactivate the fadB and fadJ genes in *E. coli* LS5218. Primers for the antibiotic genes within plasmids pKD13 and pKD3 contained ends homologous to fadJ and fadB, respectively Table 2. Knockout cassettes were amplified from appropriate plasmid templates using PrimeSTAR HS DNA polymerase (Takara) and an iCycler thermal cycler (Bio-Rad) following manufacturers' recommendations. *E. coli* LS5218 carrying the pKD46 plasmid was grown in LB with 0.3% (w/v) L-arabinose to induce expression of the λ Red system. Cells that had expressed the λ Red system from the pKD46 plasmid and grown to an OD$_{600}$ of ~0.6 were made electrocompetent and transformed with PCR knockout cassettes via an ECM 399 electroporator (BTX) at 1500 volts following the manufacturer's protocols for *E. coli*. Transformants were selected on LB-agar plates with the appropriate antibiotic. Elimination of the genes from the chromosome was confirmed by PCR. The temperature-sensitive plasmid pKD46 was expelled from the cells by growth at 37° C.

The gene encoding fadJ was eliminated from *E. coli* LS5218 first by insertion of the gene expressing kanamycin resistance into the fadJ gene on the chromosome. This insert was removed by expression of FLP recombinase from the pCP20 plasmid. Successful removal was confirmed by PCR and loss of kanamycin resistance. The temperature-sensitive plasmid pCP20 was expelled from the cells by growth at 37° C. After fadJ was eliminated, fadB was eliminated by insertion of the chloramphenicol acetyltransferase cassette from pKD3. All deletions were confirmed by PCR.

Construction of pBBR-C1J4SII Vector for PHA Production

The phaJ4 gene from *Pseudomonas putida* KT2440 (22, 46) was PCR amplified using the phaJ4 primers "phaJ4 F EcoRV" and "phaJ4 R KpnI" (Table 2), PrimeSTAR HS DNA polymerase (Takara), and an iCycler thermal cycler (Bio-Rad). The PCR product was gel-purified and cloned into the pCR-Blunt (Invitrogen) vector with T4 DNA ligase (New England Biolabs). Successful ligations were confirmed via sequencing from Geneeiz. The resulting Blunt-phaJ4 vector was digested with KpnI and the excised piece phaJ4 DNA was ligated into the KpnI site of the plasmid pBBRSTQKAB (28), creating pBBRSTQKABJ4. Correct orientation of the phaJ4 gene on the pBBRSTQKABJ4 plasmid was confirmed by restriction enzyme digest with BamHI. pBBRSTQKABJ4 was then digested with SacII to excise the unnecessary genes phaA and phaB. The linearized DNA fragment was gel-purified and ligated together at the SacII site with T4 DNA ligase, generating pBBR-C1J4SII. All restriction enzymes were purchased from New England Biolabs. All cloning transformations and plasmid preparations were performed in *E. coli* JM109.

PHA Production in *E. coli* LSBJ

*E. coli* LSBJ was made chemically competent, transformed with the pBBR-C1J4SII plasmid following standard procedures (47), and grown on LB kanamycin plates at 37° C. Single colonies were used to inoculate 50 mL of LB with kanamycin, and these cultures were grown at 30° C. in an incubating orbital shaker at 250 rpm for 12-16 hours. Aliquots (1 mL) of these 50 mL LSBJ-C1J4SII cultures were used to inoculate 100 mL of growth media in 500 mL baffled shake flasks. The PHA-production media contained LB, kanamycin, fatty acid substrates (to 2 g L$^{-1}$ for total fatty acids), and either Brij-35 or potassium phosphates as outlined above. The PHA-production media was incubated at 30° C. in an orbital shaker at 250 rpm for 48 hours. After incubation was complete, cells were harvested by centrifugation at 3,716×g for 15 min Pelleted cells were resuspended in 70% (v/v) ethanol to remove residual fatty acids, and the cells were collected again by centrifugation. Finally, the cells were washed with Nanopure filtered water (Barnstead) to remove residual ethanol, and frozen at −80° C., and dried via lyophilization.

PHA Extraction

Extraction of polymer from dried cells was based on previously published work (48). After removing appropriate dried cell fractions for gas chromatography analysis, remaining cells were treated with methanol prior to extraction. Approximately 22 mL of methanol were added to dried biomass per gram of dried biomass, and the mixture was incubated at room temperature with stirring for 5 min. The biomass was collected by centrifugation, resuspended in Nanopure filtered water, and dried via lyophilization. Polymer was then removed from the cells via soxhlet extraction with 120 mL of either acetone (for samples generated from single MCL substrates only) or chloroform. The chloroform was refluxed for approximately 5 hours after the first siphoning event. The extract was concentrated in a rotary evaporator and placed in a glass Petri dish, allowing the solvent to evaporate overnight. PHA films were then kept at room temperature pending further analysis.

Gas Chromatography (GC) and Gas Chromatography-Mass Spectroscopy (GC-MS) Analysis of PHAs Produced Repeating unit compositions of PHAs were determined by GC and GC-MS. For GC analysis, either dried cells (15-20 mg) or purified polymers (5-10 mg) were dissolved in 2 ml chloroform and 2 ml sulfuric acid:methanol (15:85) and heated at 100° C. for 140 minutes. After cooling the samples to room temperature, 1 ml of water was added to each sample. Samples were mixed by vortexing, and the aqueous and organic layers were separated by centrifugation at 485×g for 3 min. The chloroform layer containing the 3-hydroxymethyl esters was passed through a 0.45 μm polytetrafluoroethylene (PTFE) syringe filter (Restek). A total of 500 μl of the filtered sample was mixed with 500 μl of caprylic acid (1 g $L^{-1}$) in chloroform in a GC vial. Samples were then loaded by 1 μl split injection at 280° C. into a GC 2010 Gas Chromatograph with a flame ionization detector at 310° C. (Shimadzu). Samples were separated in a 30 m Rtx®-5 column (Restek, 0.25 mm id and 0.25 μmd$_f$). The heating profile for the column oven was as follows: 100° C. initial temperature, ramp to 280° C. at 8° C. $min^{-1}$, hold for 2 min, ramp to 310° C. at 20° C. $min^{-1}$, and hold for 2 min. Isolated polymers and fatty acid feedstocks were also analyzed by GC-MS, which was performed as previously described (49). Methyl/ethyl esters corresponding to PHA repeating units were determined based on retention times of known standards and resulting mass spectra when available.

Nuclear Magnetic Resonance of PHAs Produced

For further structural analysis, 10-20 mg of purified PHAs from *E. coli* LSBJ were dissolved in 1 ml of deuterated chloroform, passed through a small plug of glass wool into sample tubes, and analyzed by $^1H$ and/or gradient-enhanced-HSQC-DEPT NMR spectroscopy. $^1H$ spectra were acquired at 30° C. with a Bruker DPX 300 (300 MHz $^1H$ frequency) equipped with a 5 mm BBFO z-gradient probe. The recycle delay was 5.0 sec, the acquisition time was 3.4 sec with a 45° pulse width, and the experiment had spectral widths of 4800 Hz. The ge-enhanced-HSQC-DEPT spectra were acquired with a Bruker AVANCE 600 spectrometer (600 MHz $^1H$ frequency) equipped with a 5 mm triple resonance z-gradient probe. Data were acquired and processed in TOPSPIN v1.3 from Bruker BioSpin. The ge-HSQC-DEPT experiment had spectral widths of 4800 Hz and 25000 Hz with 2k×256 data points collected for $^1H$ and $^{13}C$ spectra, respectively.

Gel Permeation Chromatography (GPC) Analysis of PHAs Produced

The number-average molecular weight ($M_n$) and the weight-average molecular weight ($M_w$) were determined by GPC using a LC-20AD Liquid Chromatograph equipped with a SIL-20A auto-sampler and RID-10A refractive index detector (Shimadzu). Purified PHA samples were dissolved in chloroform at 0.7 mg/ml and passed through a 0.45 μm PTFE syringe filter. 50 μl of each sample were injected to the GPC and passed through an 8×50 mm styrenedivinylbenvene (SDV) guard column (5 μm particles; Polymer Standards Service) and an 8×300 mm SDV analytical column (5 μm particles; mixed bed porosity; max molecular weight 1E6 Da; Polymer Standards Service product sda0830051im). The column oven was maintained at 40° C. Chloroform was the mobile phase with a flow rate of 1 ml $min^{-1}$. Molecular weights were determined based on polystyrene standards as determined previously (4).

Thermal Analysis of PHAs Produced

The decomposition temperatures ($T_d$) of extracted PHA polymers were determined by thermogravimetric analysis (TGA). The melting temperatures ($T_m$), crystallization temperatures ($T_c$), and glass-transition temperatures ($T_g$) of the PHA polymers were determined by differential scanning calorimetry (DSC). TGA experiments were performed on a TGA Q5000IR (TA Instruments). Approximately 10 mg of extracted polymer sample was heated under nitrogen atmosphere at 20° C. $min^{-1}$ to 500° C. The $T_d$ was taken at the initiation of sample degradation. DSC experiments were performed on a DSC Q200 (TA Instruments). Approximately 10 mg of polymer sample were heated to 200° C. at 10° C. $min^{-1}$, cooled to either −40° C. or −60° C. at 5° C. $min^{-1}$, and then heated back to 200° C. at 10° C. $min^{-1}$. All DSC samples were analyzed under a nitrogen atmosphere. The $T_m$ and $T_c$ were taken at the bottom or top of their peaks, respectively, if present. The $T_g$ was taken in the middle of the transition. Both DSC and TGA data were analyzed using TA Instruments Universal Analysis 2000 software.

Tensile Strength Analysis of PHAs Produced

Extracted PHA samples were used in tensile strength experiments using a TST350 (Linkam Scientific Instruments) to determine Young's modulus, yield strength, ultimate tensile strength, and strain to failure (elongation to break). Polymer samples (400 to 800 mg) were dissolved in 10 mL chloroform and cast in glass Petri dishes (8.6 cm diameter). The dishes were covered with aluminum foil, which had small punctures to allow for even solvent evaporation. After the solvent had been allowed to evaporate overnight, the samples were moved to a vacuum desiccator for at least 24 hours. A hydraulic bench top press (Carver, Model C) was used to cut dogbones for tensile strength testing. The mold used to cut the dogbones was a scaled down ASTM Type IV mold for plastic analysis (ASTM designation: D638-10). The mold was scaled down by a factor of 2 compared to the standard, as done similarly in previous work with another standard (50). The dimensions of the cut dogbones were 1.5 mm (gauge width), 6.25 mm (gauge length), 28.75 mm (total length), and 4.75 mm (total width). Samples were measured at the middle and both ends of the dogbones using digital calipers to determine thickness. Thicknesses on average were between 0.05 and 0.15 mm. Samples were loaded onto the TST350, clamped, and pulled at a rate of 20.8 μm $s^{-1}$. The instrument was set with a 20 N load cell with a 0.01 N resolution, and the temperature was set to 25.0° C. The strain and corresponding stress on the samples were recorded using Linksys32 software. The Young's modulus, yield strength, ultimate tensile strength, and strain to failure (elongation to break) were determined from the observed stress-strain curves. The Young's modulus was taken as the slope of the initial linear portion of the stress-strain curve. The yield strength was determined using a 2% x-intercept offset of the line equation determined for the Young's modulus. The offset yield strength was then identified as the point where the 2% offset line crossed the stress-strain curve.

Results

Creation of *E. coli* LSBJ and Initial PHA Biosynthesis

To develop a bacterial strain capable of producing PHA polymers with defined repeating unit composition, *E. coli* LSBJ was made from *E. coli* LS5218 by eliminating the (S)-specific enoyl-CoA hydratase fadB and its homologue fadJ on the chromosome (FIGS. 2A-B). *E. coli* LSBJ then produced PHAs with defined repeating unit composition from fatty acids by expressing PhaJ4 and PhaC1(STQK). The fatty acids used to produce the defined polymers were the SCL fatty acid sodium butyrate (C4) and the MCL fatty acids, sodium octanoate (C8), decanoic acid (C10), 10-undecenoic acid (C11:1, Δ10), and dodecanoic acid (C12). The repeating units of the PHAs produced were representative of the fatty acid substrate in number of carbons (Table 3). GC initially showed each of the PHAs to be comprised entirely of repeating units equal in number of carbons as the starting fatty acid. For example, samples grown in the presence of sodium octanoate were comprised of 3-hydroxyoctanoate repeating units and no other MCL repeating units.

The only potential contaminants seen in the initial GC experiments of samples produced from the medium chain fatty acids were seen as peaks with retention times that matched 3-hydroxybutyrate (3HB). To confirm the absence or presence of 3HB in the PHAs not produced from sodium butyrate, polymer samples were analyzed by HSQC-DEPT NMR (FIGS. 10-13).

FIG. 10 shows $^1$H-$^{13}$C HSQC-DEPT NMR spectroscopy results for poly(3-hydroxyoctanoate) synthesized in *E. coli* LSBJ expressing the pBBR-C1J4SII plasmid. Purified polymer was dissolved in deuterated chloroform and checked for contaminating repeating units, specifically poly(3-hydroxybutyrate) (PHB). CH and CH$_3$ carbons are shown in black, and CH2 signals are shown in gray. In addition to comparison of the spectra with previous works of NMR on PHAs, the HSQC-DEPT NMR experiments were performed to confirm the absence of 3-hydroxybutyrate (3HB) repeating units in the various MCL-PHAs. 3HB within the polymer would be differentiated from the desired MCL repeating units by looking for the chiral carbon (the third carbon) and the methyl carbon's (the fourth carbon) signals. The chiral carbon of 3HB would be slightly shielded compared to that of the MCL-PHAs (67-68 ppm vs. 70-71 ppm) in the $^{13}$C portion of the spectra. The methyl carbon would give a black signal in the area of 1.30 ppm for $^1$H and 19-20 ppm for $^{13}$C. The signals in the poly(3-hydroxyoctanoate) sample that do not correspond to signals found in other MCL-PHA samples with fully saturated side chains are believed to be residual fatty acid substrate (octanoate) that was not fully removed from extracted polymer. This sample does not show detectable PHB.

FIG. 11 shows $^1$H-$^{13}$C HSQC-DEPT NMR spectroscopy results for poly(3-hydroxydecanoate) synthesized in *E. coli* LSBJ expressing the pBBR-C1J4SII plasmid. Purified polymer was dissolved in deuterated chloroform and checked for contaminating repeating units, specifically poly(3-hydroxybutyrate). CH and CH$_3$ carbons are shown in black, and CH2 signals are shown in gray. In addition to comparison of the spectra with previous works of NMR on PHAs, the HSQC-DEPT NMR experiments were performed to confirm the absence of 3-hydroxybutyrate (3HB) repeating units in the various MCL-PHAs. 3HB within the polymer would be differentiated from the desired MCL repeating units by looking for the chiral carbon (the third carbon) and the methyl carbon's (the fourth carbon) signals. The chiral carbon of 3HB would be slightly shielded compared to that of the MCL-PHAs (67-68 ppm vs. 70-71 ppm) in the $^{13}$C portion of the spectra. The methyl carbon would give a black signal in the area of 1.30 ppm for $^1$H and 19-20 ppm for $^{13}$C. This sample does not show detectable PHB.

FIG. 12 shows $^1$H-$^{13}$C HSQC-DEPT NMR spectroscopy results for poly(3-hydroxy-10-undecenoate) synthesized in *E. coli* LSBJ expressing the pBBR-C1J4SII plasmid. Purified polymer was dissolved in deuterated chloroform and checked for contaminating repeating units, specifically poly(3-hydroxybutyrate). CH and CH$_3$ carbons are shown in black, and CH$_2$ signals are shown in gray. In addition to comparison of the spectra with previous works of NMR on PHAs, the HSQC-DEPT NMR experiments were performed to confirm the absence of 3-hydroxybutyrate (3HB) repeating units in the various MCL-PHAs. 3HB within the polymer would be differentiated from the desired MCL repeating units by looking for the chiral carbon (the third carbon) and the methyl carbon's (the fourth carbon) signals. The chiral carbon of 3HB would be slightly shielded compared to that of the MCL-PHAs (67-68 ppm vs. 70-71 ppm) in the $^{13}$C portion of the spectra. The methyl carbon would give a black signal in the area of 1.30 ppm for $^1$H and 19-20 ppm for $^{13}$C. The fatty acid substrates were found to have detectable amounts of different fatty acids in GC-MS experiments. This may have been the cause for detectable amounts of repeating units (GC-MS) in PHAs not equal in size to the starting substrate. The fatty acid substrate for production of poly(3-hyroxy-10-undecenoate) (PHUn), 10-undecenoic acid, was listed as 95% pure by the manufacturer (SAFC). The contaminating materials likely contain fully saturated fatty acids. These fully saturated fatty acids would also be incorporated into PHAs synthesized by this system. These potential contaminants can be seen in the $^1$H spectrum of the PHUn sample at ~0.8 ppm. This is the same chemical shift seen for the terminal methyl groups of the polymers containing fully saturated side chains in the repeating units (FIGS. 10, 11 and 13). This sample does not show detectable PHB.

FIG. 13 shows $^1$H-$^{13}$C HSQC-DEPT NMR spectroscopy results for poly(3-hydroxydodecanoate) synthesized in *E. coli* LSBJ expressing the pBBR-C1J4SII plasmid. Purified polymer was dissolved in deuterated chloroform and checked for contaminating repeating units, specifically poly(3-hydroxybutyrate). CH and CH$_3$ carbons are shown in black, and CH$_2$ signals are shown in gray. In addition to comparison of the spectra with previous works of NMR on PHAs, the HSQC-DEPT NMR experiments were performed to confirm the absence of 3-hydroxybutyrate (3HB) repeating units in the various MCL-PHAs. 3HB within the polymer would be differentiated from the desired MCL repeating units by looking for the chiral carbon (the third carbon) and the methyl carbon's (the fourth carbon) signals. The chiral carbon of 3HB would be slightly shielded compared to that of the MCL-PHAs (67-68 ppm vs. 70-71 ppm) in the $^{13}$C portion of the spectra. The methyl carbon would give a black signal in the area of 1.30 ppm for $^1$H and 19-20 ppm for $^{13}$C. This sample does not show detectable PHB.

Chemical shifts were compared to previous works utilizing NMR to analyze PHAs (28,51,52). Chemical shifts corresponding to the 3HB repeating unit were not observed in the NMR experiments (FIGS. 10-13).

Extracted PHAs were also analyzed by gas GC-MS, and MCL repeating units not equal in carbon length to the starting fatty acid were found. However, these minor fractions were in amounts lower than the GC detection limit and only qualitatively detected with GC-MS (Table 3). The carbon sources for the PHAs (i.e. fatty acids) were also analyzed by GC-MS, and the substrates were also found to have detectable amounts of contaminating fatty acids. Fully saturated fatty acids were present in large enough quantities in the 10-undecenoic acid substrate that the subsequent incorporation of the contaminants in the PHAs could be detected in HSQC-DEPT NMR of the poly(3-hydroxy-10-undecenoate) (PHUn) sample (see FIG. 12 and discussion of FIG. 12 above).

PHB was also synthesized using this system. Sodium butyrate was added to the cell media to generate the SCL PHA. Table 3 shows that PHB was accumulated at 7.81% of the cell dry weight in *E. coli* LSBJ. The PHB synthesized was not in large enough quantities for further purification and testing. After successful synthesis of PHB in this system, it is inferred that all repeating units can be synthesized and controlled from four and up to twelve carbons in length.

Physical and Thermal Properties of PHAs Synthesized from one Fatty Acid Substrate in *E. coli* LSBJ To examine the physical properties of the PHA polymers produced, the weight average molecular weights ($M_w$), number average molecular weights ($M_n$), and polydispersities ($M_w/M_n$) were determined by GPC (Table 4). The decomposition temperatures ($T_d$) for each of the MCL PHAs produced were determined by TGA; and the glass-transition temperatures ($T_g$), melting temperatures ($T_m$), and crystallization temperatures ($T_c$) were determined by DSC. These results are shown in Table 4. The DSC and TGA scans for these samples are shown in FIGS. 14A-B.

FIGS. 14A-B show thermal analysis of purified medium-chain-length poly(3-hydroxyalkanoates). Differential scanning calorimetry scans are shown in (A), and thermogravimetric analysis results are shown in (B) for purified poly(3-hydroxyoctanoate) (PHO), poly(3-hydroxydecanoate) (PHD), poly(3-hydroxy-10-undecenoate) (PHun), and poly (3-hydroxydodecanoate) (PHDD).

PHA Copolymer Production in *E. coli* LSBJ

Four different groups of copolymers were synthesized in *E. coli* LSBJ carrying the pBBR-C1J4SII plasmid: poly[(R)-3-hydroxydodecanoate-co-(R)-3-hydroxydecanoate] (PHDDHD), poly[(R)-3-hydroxydodecanoate-co-(R)-3-hydroxyoctanoate] (PHDDHO), poly[(R)-3-hydroxydecanoate-co-(R)-3-hydroxyoctanoate] (PHDHO), and poly[(R)-3-hydroxyoctanoate-co-(R)-3-hydroxybutyrate] (PHOHB). Synthesis of the desired sizes for the repeating units were achieved by incorporating fatty acid substrates that were equal in carbon atom length (for example, sodium octanoate was incorporated into PHAs as (R)-3-hydroxyoctanoate). The total mass of fatty acids fed during PHA copolymer production was 2 g L$^{-1}$. The mole ratios of the fatty acid substrates were altered in each experiment in an effort to ascertain correlations between specific substrate mole ratios and the corresponding mole ratios in the repeating units of the polymers. After incubation of the cells was complete, the mole ratios of the polymer produced were determined either by GC or NMR. Samples that were grown in the presence of only MCL substrates (sodium octanoate, decanoate, and dodecanoate) were analyzed by GC. The results for using dodecanoate and decanoate as PHA substrates at varying mole ratios are shown in Table 5. Results for the two other MCL copolymer systems (PHDDHO and PHDHO) are provided in Tables 6 and 7.

TABLE 5

Poly[(R)-3-hydroxydodecanoate-co-(R)-3-hydroxydecanoate] synthesis in *E. coli* LSBJ with varying mole ratios of fatty acid substrates

| Substrate ratio | CDW[a, b] | PHA[b] | Composition (mol %)[b, c] | | | | |
|---|---|---|---|---|---|---|---|
| (C10:C12) | (g L$^{-1}$) | (mass %) | 3HB | 3HHx | 3HO | 3HD | 3HDD |
| 70:30 | 1.02 ± 0.06 | 26.3 ± 0.8 | 0 | 0 | 0 | 45.5 ± 0.6 | 54.5 ± 0.6 |
| 60:40 | 1.21 ± 0.03 | 22.4 ± 1.1 | 0 | 0 | 0 | 39.2 ± 0.6 | 60.8 ± 0.6 |
| 50:50 | 0.99 ± 0.08 | 29.5 ± 1.1 | 0 | 0 | 0 | 28.0 ± 0.8 | 72.0 ± 0.8 |
| 40:60 | 1.22 ± 0.05 | 21.1 ± 0.7 | 0 | 0 | 0 | 23.2 ± 1.0 | 76.8 ± 1.0 |
| 30:70 | 0.89 ± 0.04 | 26.1 ± 1.4 | 0 | 0 | 0 | 14.8 ± 0.1 | 85.2 ± 0.1 |

[a]Cell dry weight.
[b]Values determined by GC. All values are averages of triplicate experiments plus or minus the standard deviations about those averages.
[c]3HB, 3-hydroxybutyrate; 3HHx, 3-hydroxyhexanoate; 3HO, 3-hydroxyoctanoate; 3HD, 3-hydroxydecanoate; 3HDD, 3-hydroxydodecanoate.

TABLE 6

Poly[(R)-3-hydroxydodecanoate-co-(R)-3-hydroxyoctanoate] synthesis in *E. coli* LSBJ with varying mol ratios of fatty acid substrates

| Substrate Ratio | CDW[a, b] | PHA[b] | Composition[b, c] (mol %) | | | | |
|---|---|---|---|---|---|---|---|
| (C12:C8) | (g L$^{-1}$) | (mass %) | 3HB | 3HHx | 3HO | 3HD | 3HDD |
| 30:70 | 1.21 ± 0.08 | 24.9 ± 3.4 | 0 | 0 | 27.6 ± 3.4 | 0 | 72.4 ± 3.4 |
| 40:60 | 1.21 ± 0.08 | 33.4 ± 3.5 | 0 | 0 | 16.2 ± 0.8 | 0.2 ± 0.0 | 83.5 ± 0.8 |
| 50:50 | 1.34 ± 0.13 | 25.2 ± 5.2 | 0 | 0 | 9.3 ± 0.6 | 0.2 ± 0.2 | 90.6 ± 0.7 |
| 60:40 | 1.36 ± 0.02 | 33.5 ± 1.3 | 0 | 0 | 7.4 ± 0.3 | 0.4 ± 0.1 | 92.2 ± 0.3 |
| 70:30 | 1.30 ± 0.09 | 21.4 ± 7.3 | 0 | 0 | 4.0 ± 0.2 | 0.2 ± 0.2 | 95.8 ± 0.3 |

[a]Cell dry weight.
[b]Values determined by GC. All values are averages of triplicate experiments plus or minus the standard deviations about those average.
[c]3HB, 3-hydroxybutyrate; 3HHx, 3-hydroxyhexanoate; 3HO, 3-hydroxyoctanoate; 3HD, 3 hydroxydecanoate; 3HDD, 3-hydroxydodecanoate.

TABLE 7

Poly[(R)-3-hydroxydecanoate-co-(R)-3-hydroxyoctanoate] synthesis in
E. coli LSBJ with varying mol ratios of fatty acid substrates

| Substrate Ratio (C10:C8) | CDW[a, b] (g L$^{-1}$) | PHA[b] (mass %) | Composition[b, c] (mol %) | | | | |
|---|---|---|---|---|---|---|---|
| | | | 3HB | 3HHx | 3HO | 3HD | 3HDD |
| 30:70 | 1.03 ± 1.10 | 32.6 ± 2.5 | 0 | 0 | 55.0 ± 1.0 | 45.0 ± 1.0 | 0 |
| 40:60 | 1.25 ± 0.00 | 36.3 ± 1.7 | 0 | 0 | 42.6 ± 0.7 | 57.3 ± 0.8 | 0.1 ± 0.1 |
| 50:50 | 1.17 ± 0.08 | 25.3 ± 5.1 | 0 | 0 | 32.0 ± 0.8 | 68.0 ± 0.8 | 0 |
| 60:40 | 1.32 ± 0.20 | 34.5 ± 0.4 | 0 | 0 | 22.6 ± 1.1 | 77.3 ± 1.1 | 0.2 ± 0.0 |
| 70:30 | 1.22 ± 0.19 | 24.6 ± 1.7 | 0 | 0 | 15.2 ± 0.5 | 84.8 ± 0.5 | 0 |

[a]Cell dry weight.
[b]Values determined by GC. All values are averages of triplicate experiments plus or minus the standard deviations about those average
[c]3HB, 3-hydroxybutyrate; 3HHx, 3-hydroxyhexanoate; 3HO, 3-hydroxyoctanoate; 3HD, 3-hydroxydecanoate; 3HDD, 3-hydroxydodecanoate.

Given the mole ratios of the repeating units in the polymer determined by GC in Tables 5-7, the data were plotted to establish trend lines based on the initial fatty acid substrate ratios (FIGS. 15-17).

FIG. 15 shows the mol ratio of repeating units in poly[(R)-3-hydroxydodecanoate-co-(R)-3-hydroxydecanoate] polymer samples in relation to the starting fatty acid substrate ratio. The fatty acid substrates were used by E. coli LSBJ containing the pBBR-C1J4SII plasmid to synthesize PHAs as described in herein. All values were determined by GC and represent averages of three identical experiments. Error bars represent standard deviations about those averages.

FIG. 16 shows the mol ratio of repeating units in poly[(R)-3-hydroxydodecanoate-co-(R)-3-hydroxyoctanoate] polymer samples in relation to the starting fatty acid substrate ratio. The fatty acid substrates were used by E. coli LSBJ containing the pBBR-C1J4SII plasmid to synthesize PHAs as described herein. All values were determined by GC and represent averages of three identical experiments. Error bars represent standard deviations about those averages.

FIG. 17 shows the mol ratio of repeating units in poly[(R)-3-hydroxydecanoate-co-(R)-3-hydroxyoctanoate] polymer samples in relation to the starting fatty acid substrate ratio. The fatty acid substrates were used by E. coli LSBJ containing the pBBR-C1J4SII plasmid to synthesize PHAs as described herein. All values were determined by GC and represent averages of three identical experiments. Error bars represent standard deviations about those averages.

Each of the regressions was analyzed, and for each regression analysis, the slopes of the lines were found to be statistically different than zero (p-value≤0). These trend lines allow for the prediction and production of MCL PHA copolymers with desired and specific final mole ratios of repeating units. As an example, we attempted to synthesize a PHDDHD copolymer with a repeating unit mole ratio of 65:35 C12:C10. Based on the trend for PHDDHD copolymers (FIG. 15), it was predicted that a C12:C10 substrate ratio of 43.1:56.9 could be used to produce a PHDDHD copolymer with a mole ratio of 65:35 C12:C10 for the repeating units. Cells were grown with this ratio of C12:C10 substrate fatty acid substrates, and after incubation of the cells with the substrates and analysis by GC, the polymers produced were found to have 64.0±1.4 mol % (R)-3-hydroxydodecanoate and 36.0±1.4 mol % (R)-3-hydroxydecanoate repeating units by GC. This result clearly demonstrates our ability to produce MCL PHA copolymers with defined ratios of repeating units.

Due to the structural differences between the (R)-3-hydroxyoctanoate and (R)-3-hydroxybutyrate, the mole ratios for the SCL-co-MCL copolymer PHOHB were determined by $^1$H NMR as opposed to GC. MCL PHA repeating units cannot be differentiated from one another via $^1$H NMR, and therefore GC was used for quantification of the PHDDHD, PHDDHO, and PHDHO samples. GC was used to confirm that only (R)-3-hydroxyoctanoate and (R)-3-hydroxybutyrate were present in the PHOHB polymer. After initial GC experiments, PHAs were extracted from the cells and analyzed by $^1$H NMR. A sample spectrum is shown in FIG. 8. All peak integrals were standardized against the signal at 0.90 ppm, representing the terminal methyl protons of the (R)-3-hydroxyoctanoate repeating unit. Setting this peak integral value to 3.0 allowed for determination of repeating unit mole ratios by subtracting the expected integral values for (R)-3-hydroxyoctanoate from the remaining peaks. This process was carried out for PHOHB copolymers produced from C8:C4 substrate ratios of 2:98, 5:95, 10:90, 15:85, and 20:80, and the repeating unit mole ratios in the polymers are provided in Table 8.

As was done for the PHDDHD system, the correlation between feedstock ratio and resulting repeating unit ratio in PHOHB was quantified based on the compositional data collected for the PHOHB copolymers (FIG. 18).

FIG. 18 shows the mol ratio of repeating units in poly[(R)-3-hydroxyoctanoate-co-(R)-3-hydroxybutyrate] polymer samples in relation to the starting fatty acid substrate ratio. The fatty acid substrates were used by E. coli LSBJ containing the pBBR-C1J4SII plasmid to synthesize PHAs as described herein. All values were determined by NMR and represent averages of integrations at peak shifts at 1.3, 2.6, and 5.2 ppm in $^1$H NMR spectra. These integrations were compared to the integration at 0.9 ppm, which was set to 3.0 (see FIG. 2 for details). Error bars represent standard deviations about those averages.

The $^1$H NMR experiments showed a linear trend of repeating unit mole ratios compared to starting substrate mole ratios. Analysis of the regression again showed that the slope was statistically different from zero (p-value≤0).

Based on this correlation, it was predicted that a PHOHB copolymer containing a ratio of 10:90 C8:C4 could be synthesized in E. coli LSBJ if the strain was grown with a fatty acid substrate mole ratio of 3.3:96.7 C8:C4. Carrying out an experiment with this substrate ratio lead to the production of a polymer with a C8:C4 ratio of 9.8:90.2 (Table 8). These results show unprecedented precision in the control over repeating unit ratios for both SCL-co-MCL PHAs and MCL PHA copolymers.

GPC of select PHA Copolymers Produced in E. coli LSBJ

The molecular weights of each of the PHOHB copolymers were estimated by GPC. As shown in Table 8, both the weight average ($M_w$) and number average ($M_n$) molecular weights of the polymers decreased with an increasing concentration of 3HO repeating units. The polydispersities (defined as the ratio of $M_w$ to $M_n$) for the PHOHB samples were typically between 2.44 and 2.80. The yield of PHA produced as a percent of the dry cell mass tended to be greater when the 3HO concentration exceeded 10%.

TABLE 9

Poly[(R)-3-hydroxyoctanoate-co-(R)-3-hydroxybutyrate] repeating unit mole ratios and thermal properties

| Substrate ratio (C8:C4) | Polymer ratio (C8:C4) | $T_d$ (° C.) | $T_g$ (° C.) | $T_c$ (° C.) | $T_m$ (° C.) |
|---|---|---|---|---|---|
| 2:98 | 6.4:93.6 | 230 | −1.42 | 65.1 | 158 |
| 3.3:96.7 | 9.8:90.2 | 214 | −2.34 | 67.0 | 158 |
| 5:95 | 14.7:85.3 | 217 | −2.23 | 77.6 | 156 |
| 10:90 | 21.8:78.2 | 234 | −20.8/−4.89 | 77.3 | 157 |
| 15:85 | 31.3:68.7 | 229 | −26.0/−6.24 | n.d. | n.d. |
| 20:80 | 38.0:62.0 | 220 | −29.0/−5.32 | n.d. | n.d. |

$T_d$, degradation temperature;
$T_g$, glass-transition temperature;
$T_c$, crystallization temperature;
$T_m$, melting temperature;
n.d., not detected.

Melting and crystallization events were observed in PHOHB samples that contained between 6 and 22% 3HO,

TABLE 8

Polymer yield and molecular weight estimates for various poly[(R)-3-hydroxyoctanoate-co-(R)-3-hydroxybutyrate] samples

| Substrate ratio (C8:C4) | Polymer ratio (C8:C4) | CDW (g L$^{-1}$) | PHA (mass %) | $M_w$ (kDa) | $M_n$ (kDa) | $M_w/M_n$ |
|---|---|---|---|---|---|---|
| 2:98 | 6.4:93.6 | 1.49 ± 0.03 | 36.4 ± 2.6 | 417 ± 4 | 171 ± 5 | 2.44 ± 0.05 |
| 3.3:96.7 | 9.8:90.2 | 1.70 ± 0.07 | 38.8 ± 3.1 | 390 ± 8 | 139 ± 5 | 2.80 ± 0.10 |
| 5:95 | 14.7:85.3 | 1.63 ± 0.05 | 47.0 ± 2.7 | 379 ± 9 | 154 ± 6 | 2.46 ± 0.03 |
| 10:90 | 21.8:78.2 | 1.52 ± 0.03 | 51.5 ± 5.5 | 333 ± 4 | 127 ± 5 | 2.62 ± 0.09 |
| 15:85 | 31.3:68.7 | 1.35 ± 0.38 | 48.9 ± 0.2 | 323 ± 4 | 121 ± 3 | 2.68 ± 0.03 |
| 20:80 | 38.0:62.0 | 1.61 ± 0.04 | 51.8 ± 4.6 | 301 ± 2 | 114 ± 1 | 2.65 ± 0.01 |

CDW, cell dry weight;
$M_w$, weight average molecular weight;
$M_n$, number average molecular weight;
$M_w/M_n$, polydispersity.
Polymer C8:C4 ratios were determined by $^1$H NMR.
CDW and PHA yield determined by gas chromatography.
Molecular weights determined by gel permeation chromatography.
Values represent averages of triplicate experiments plus or minus standard deviations about those averages.

Thermal Properties of select PHA Copolymers Produced in E. coli LSBJ

DSC and TGA experiments were carried out to determine the degradation, glass-transition, crystallization, and melting temperatures (Table 9 and FIGS. 19 and 20).

Figure 20:
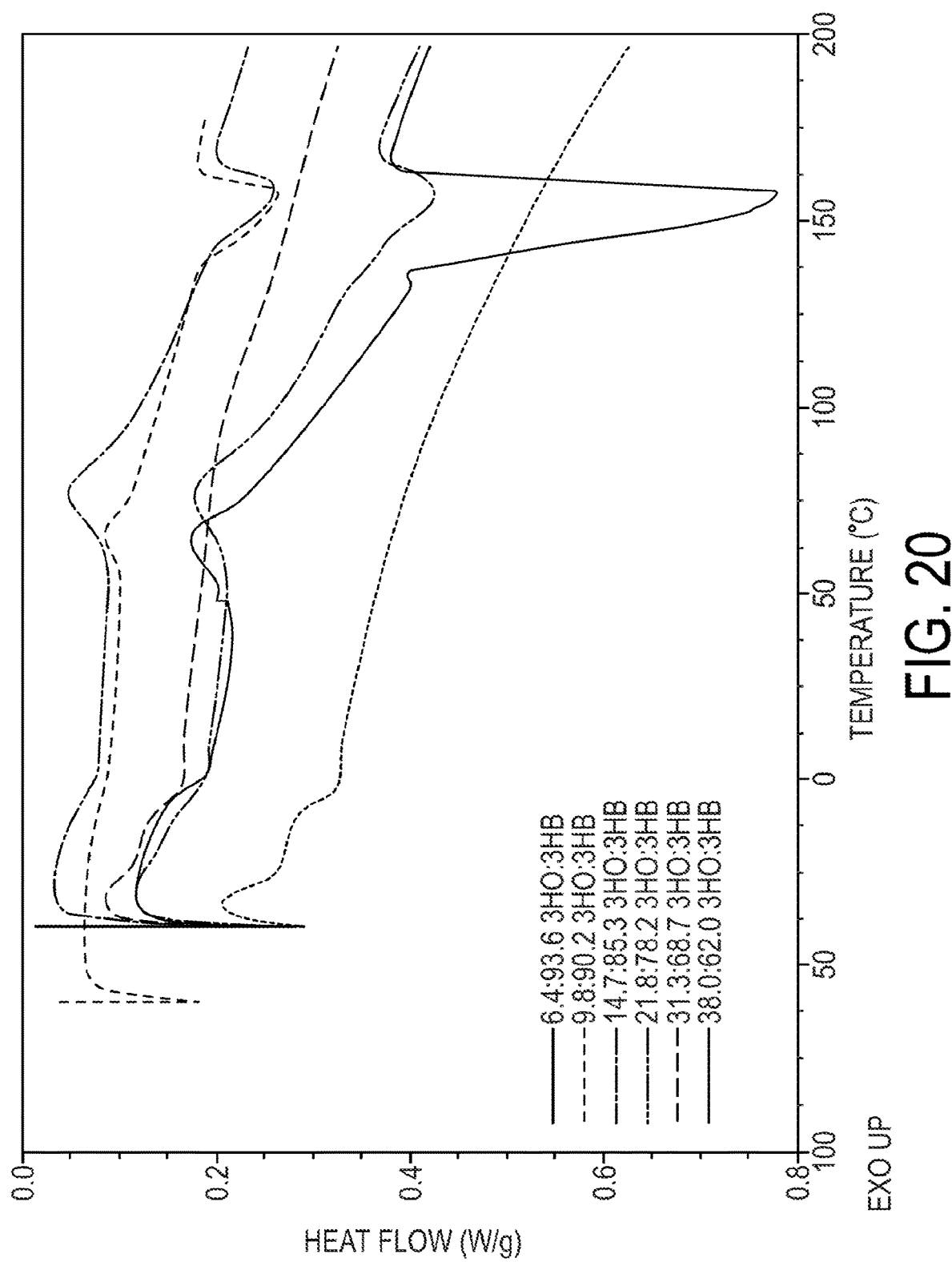
FIG. 20 shows DSC scans of various poly[(R)-3-hydroxyoctanoate-co-(R)-3-hydroxybutyrate] samples synthesized in E. coli LSBJ containing the pBBR-C1J4SII plasmid.

The degradation temperatures for all PHOHB samples were between 214° C. and 235° C. Analysis of the DSC scans for the PHOHB samples with between 6 and 15% (R)-3-hydroxyoctanoate (3HO) repeating units showed a single glass-transition temperature, which was always above the reported glass-transition temperatures for poly[(R)-3-hydroxyoctanoate] (PHO) (44,53) and below the more commonly reported value of 4° C. for poly[(R)-3-hydroxybutyrate] (PHB) (29). As the concentration of the 3HO repeating units was increased above 15% in the PHOHB copolymers, two distinct glass-transitions were observed. The glass-transition peak at the lower temperature decreased with increasing amounts of 3HO present in the polymer (Table 9), approaching but not reaching previously reported values for PHO (44,53). The second glass-transition temperature was between −4.5° C. and −6.3° C.

but not in those for which the 3HO content was greater than or equal to 31.3% (Table 9) and FIG. 20). The observed melting temperatures that were observed were between 157° C. and 160° C. The crystallization temperatures increased with increasing amounts of 3HO in the copolymer. The lowest crystallization temperature was 65.1° C., corresponding to the lowest amount of 3HO (6.4%), and the values increased to approximately 77° C. before the exothermic events were no longer observed.

Tensile Strength Analyses of select PHA Copolymers Produced in E. coli LSBJ

Tensile strength tests were performed on the PHOHB samples to investigate the correlation between physical properties and compositional changes in the repeating units. Initially, the samples that were generated with substrate C8:C4 ratios of 2:98, 5:95, 10:90, and 15:85 were analyzed as described above in Materials and Methods. The polymer generated from a C8:C4 20:80 substrate ratio was too tacky and amorphous to punch consistent dogbone samples without stretching the polymer significantly prior to analysis. However, for other C8:C4 ratios, Young's modulus, yield strength, ultimate tensile strength, and strain to failure (elongation to break) were determined from the stress-strain curves (FIGS. 9 and 21).

Figure 21:
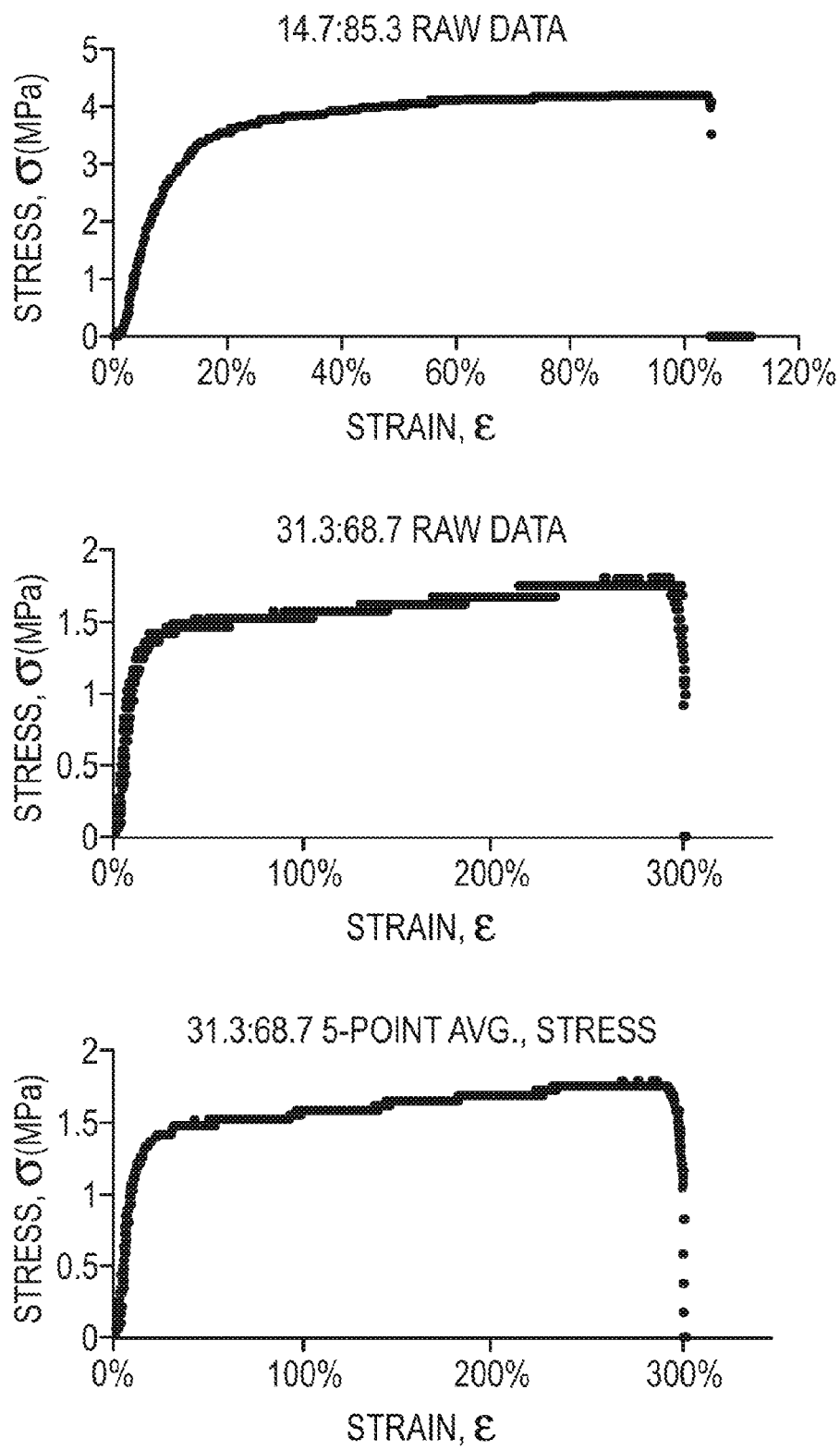

FIG. 21 shows examples of data generated in tensile strength analysis experiments with poly[(R)-3-hydroxyoctanoate-co-(R)-3-hydroxybutyrate] samples. Most samples resembled the top chart, which is one example of data from the samples with a mol ratio of 14.7:85.3, (R)-3-hydroxyoctanoate to (R)-3-hydroxybutyrate. The samples that contained a mol ratio of 31.3:68.7 (R)-3-hydroxyoctanoate to (R)-3-hydroxybutyrate were smoothed with a 5-point rolling average (bottom chart) of the raw Stress values (middle chart).

The ability to accurately resolve data points in these experiments was compromised once the C8:C4 ratio reached 31.3:68.7 (the sample created with the 15:85 C8:C4 substrate ratio). Data collected from these polymer samples were smoothed with a five-point rolling average to estimate the parameters shown in FIGS. 9A-D (see also FIG. 21 and discussion of FIG. 21 above).

After these initial tensile strength analyses were completed, the PHOHB polymer containing a C8:C4 repeating unit ratio of 9.8:90.2 was also tested. The Young's modulus and strain to failure were in between those of the PHOHB polymers with C8:C4 repeating unit ratios of 6.4:93.6 and 14.7:85.3. The values for the yield strength and the ultimate tensile strength closely resembled those for the PHOHB polymer with a repeating unit ratio of 6.4:93.6. There was a notable drop off in the yield strength and ultimate tensile strength once the 3HO concentration moved to ≥14.7 mol % of the copolymer (or above 9.8 mol %).

The physical properties were further analyzed for statistical relevance using analysis of variance (ANOVA) tests with the software program MINITAB. There were strong correlations among the four physical properties that were measured, and ANOVA tests showed that the means were statistically different (p-value of <0.001). To gain a better understanding of the relationship between the variables as a function of the C8:C4 ratios, linear regression followed by further analysis of variance was used. The plots generated showed that the trends seen in FIGS. 9A-D are statistically significant. This confirms that the different C8:C4 ratios conferred statistically different strength and modulus values (Table 10 and FIGS. 22 and 23).

TABLE 10

Correlations of poly[(R)-3-hydroxyoctanoate-co-(R)-3-hydroxybutyrate] physical property values.

| | Young's modulus | Yield strength | Elongation to break |
|---|---|---|---|
| Yield strength | 0.923 | | |
| Ultimate tensile strength | 0.937 | 0.993 | |
| Elongation to break | −0.795 | −0.783 | −0.779 |

Figure 17:
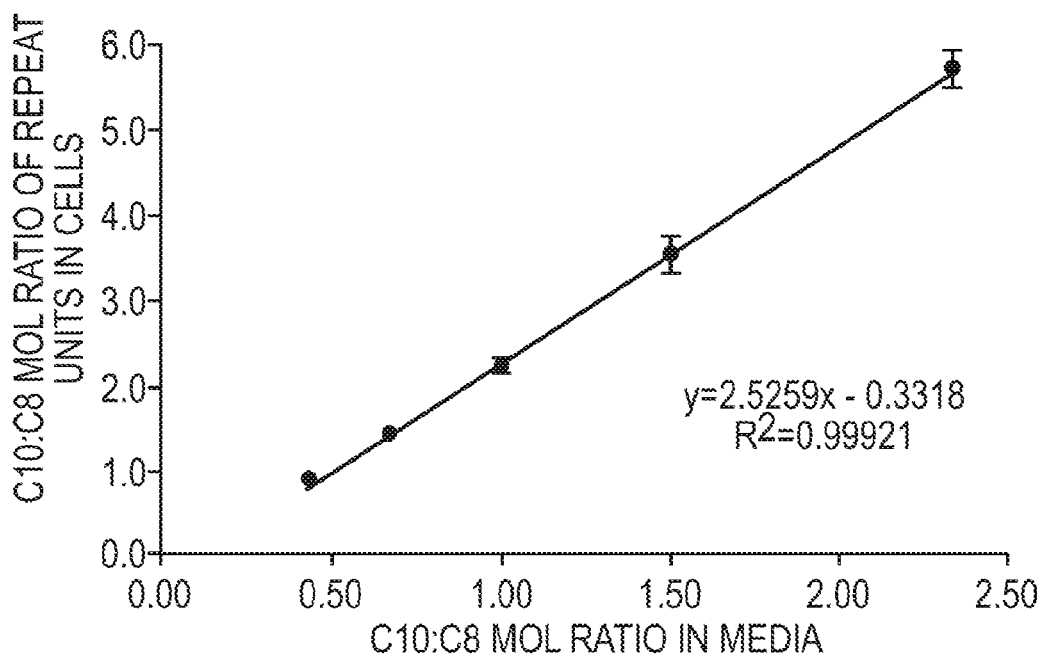
Figure 18:
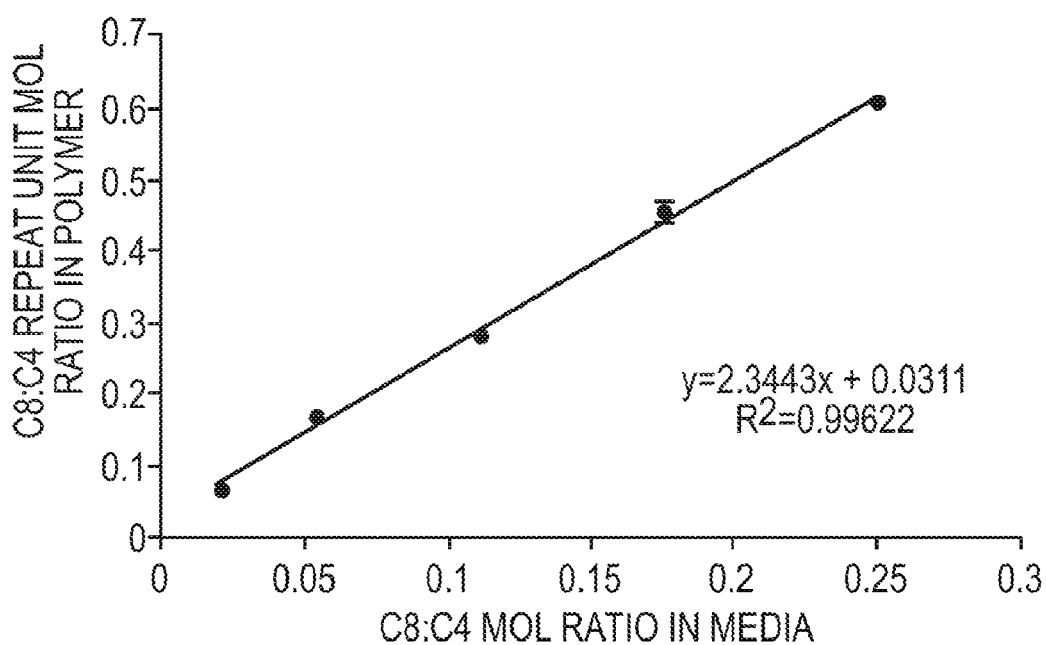

To gain a better understanding of the relationship between the variables as the C8:C4 ratios changed, linear regression followed by further analysis of variance was used. Using the Young's modulus data as an example, the percent 3HO (C8) in the polymer was used as the "x" variable, and the natural logarithm of the physical property values were used as the "y" variable. Using the software program MINITAB, a plot for the linear regression described was generated for the Young's modulus experiments (FIG. 17). Analysis of variance was used again to test if the regression relationship is statistically significant. The p-value for this analysis was <0.001, indicating the relationship is statistically significant and the Young's modulus did decrease with increasing amounts of 3HO in the PHOHB polymers. This same process was repeated for ultimate tensile strength data as well (FIG. 18), and again the p-value for this analysis was <0.001, indicating the relationship is statistically significant.

Figure 22:
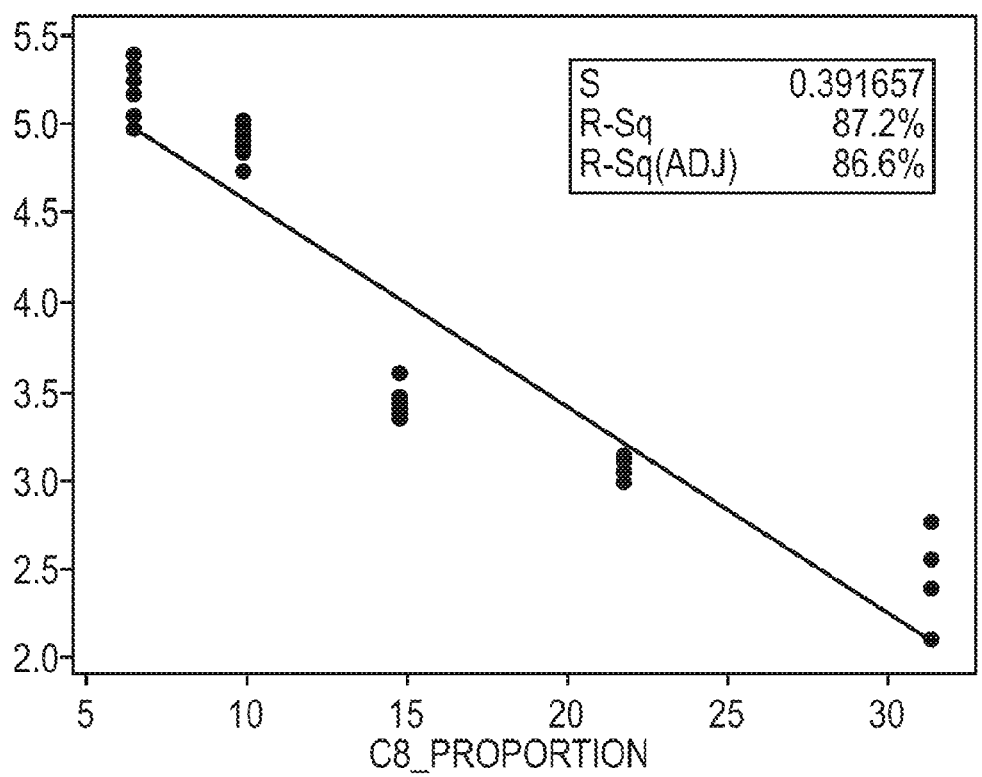

FIG. 22 shows a plot of the natural logarithm of Young's modulus values (LN_Yng) against the percent of 3HO (C8_Proportion) in of poly[(R)-3-hydroxyoctanoate-co-(R)-3-hydroxybutyrate] samples. Plot was made in the MINITAB software program.

Figure 23:
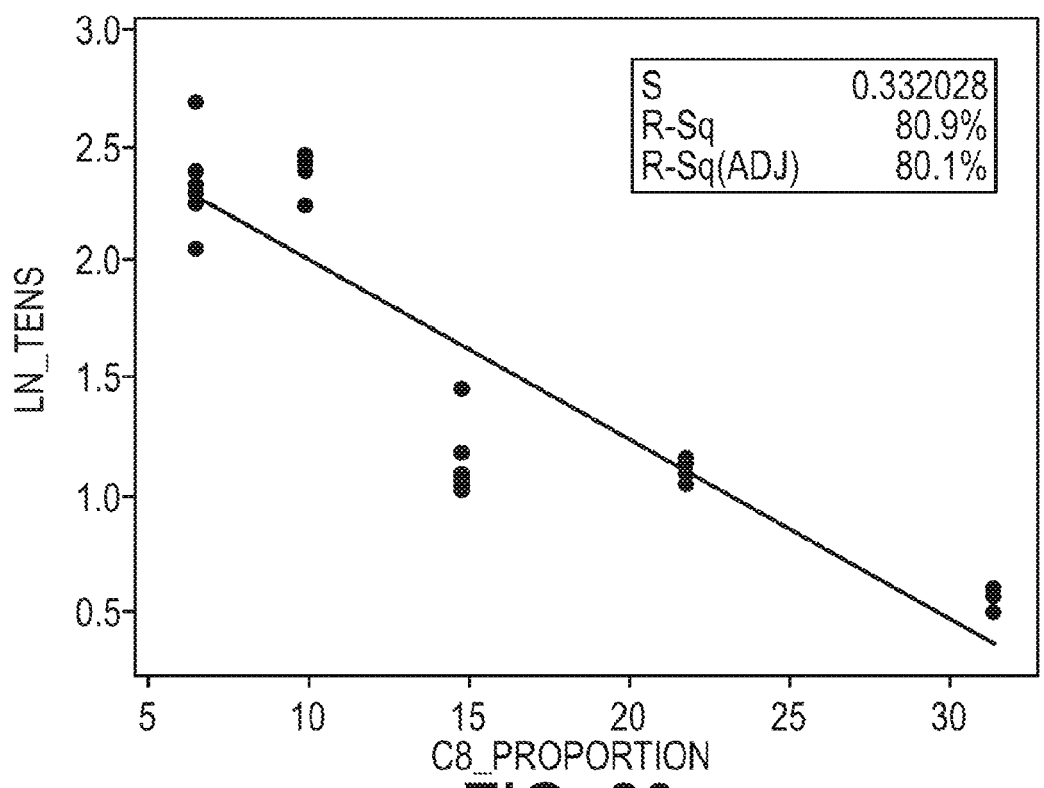

FIG. 23 shows a plot of the natural logarithm of ultimate tensile strength values (LN_Tens) against the percent of 3HO (C8_Proportion) in of poly[(R)-3-hydroxyoctanoate-co-(R)-3-hydroxybutyrate] samples. Plot was made in the MINITAB software program.

Figure 24A:
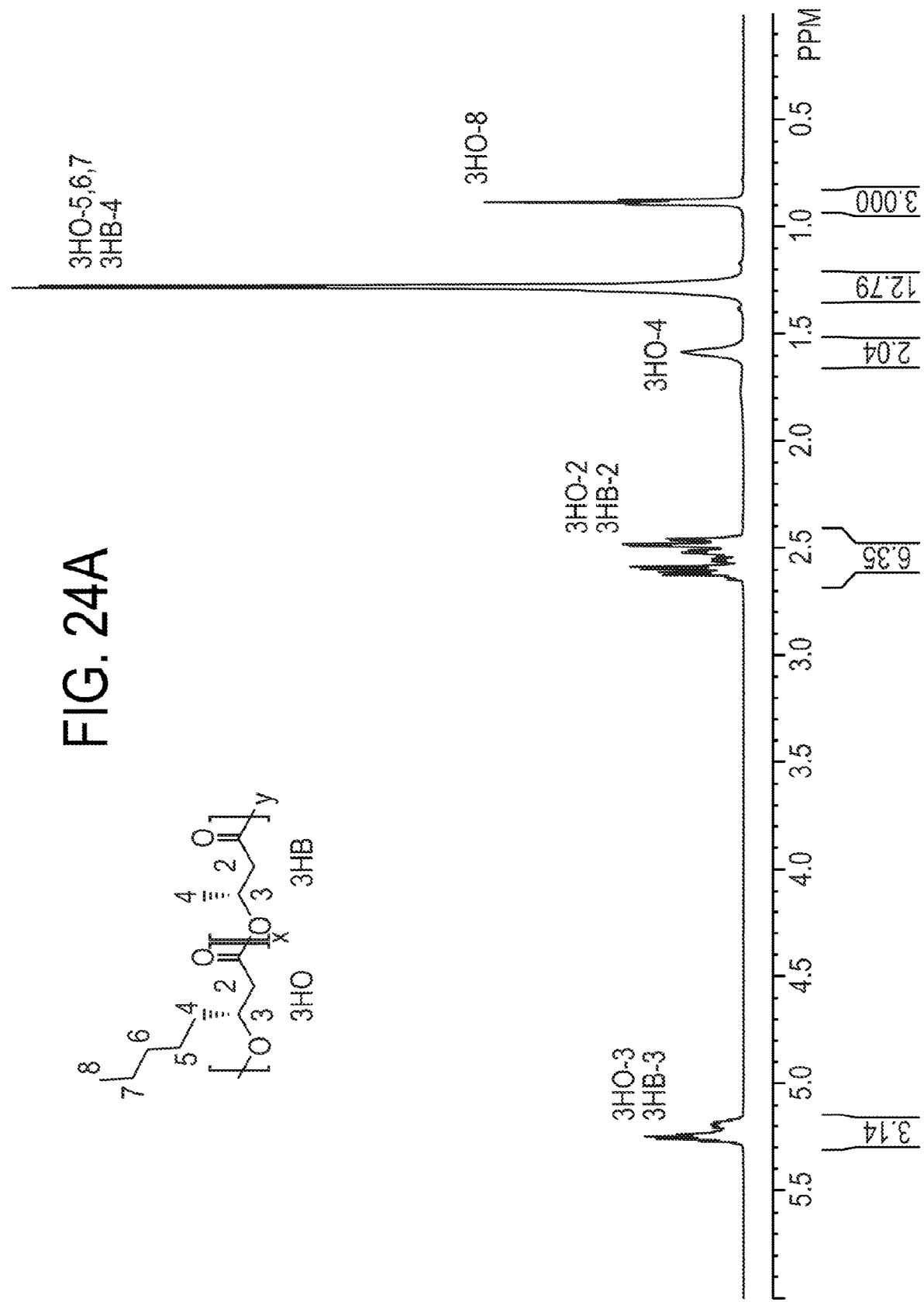
Figure 24B:
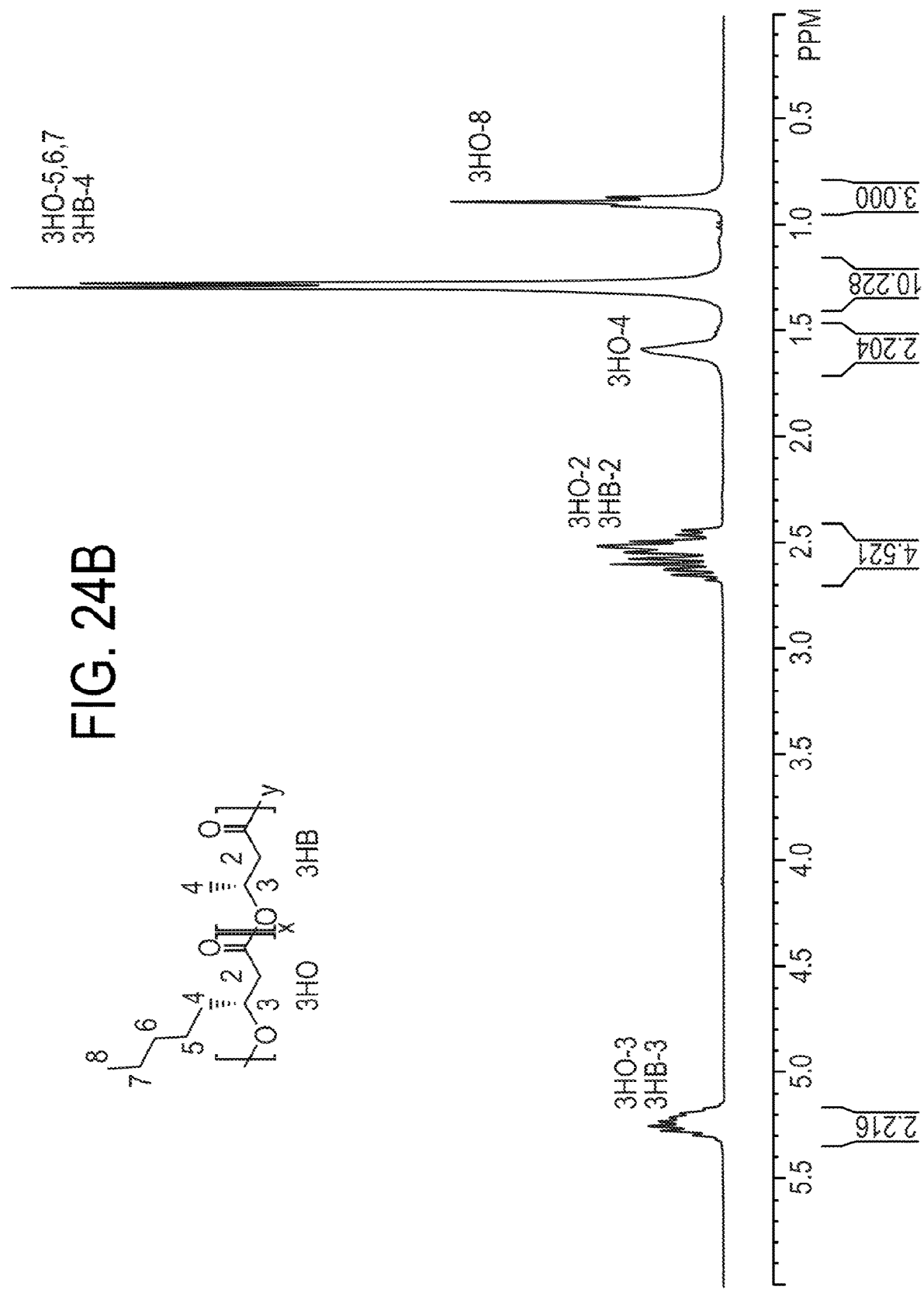
Figure 24C:
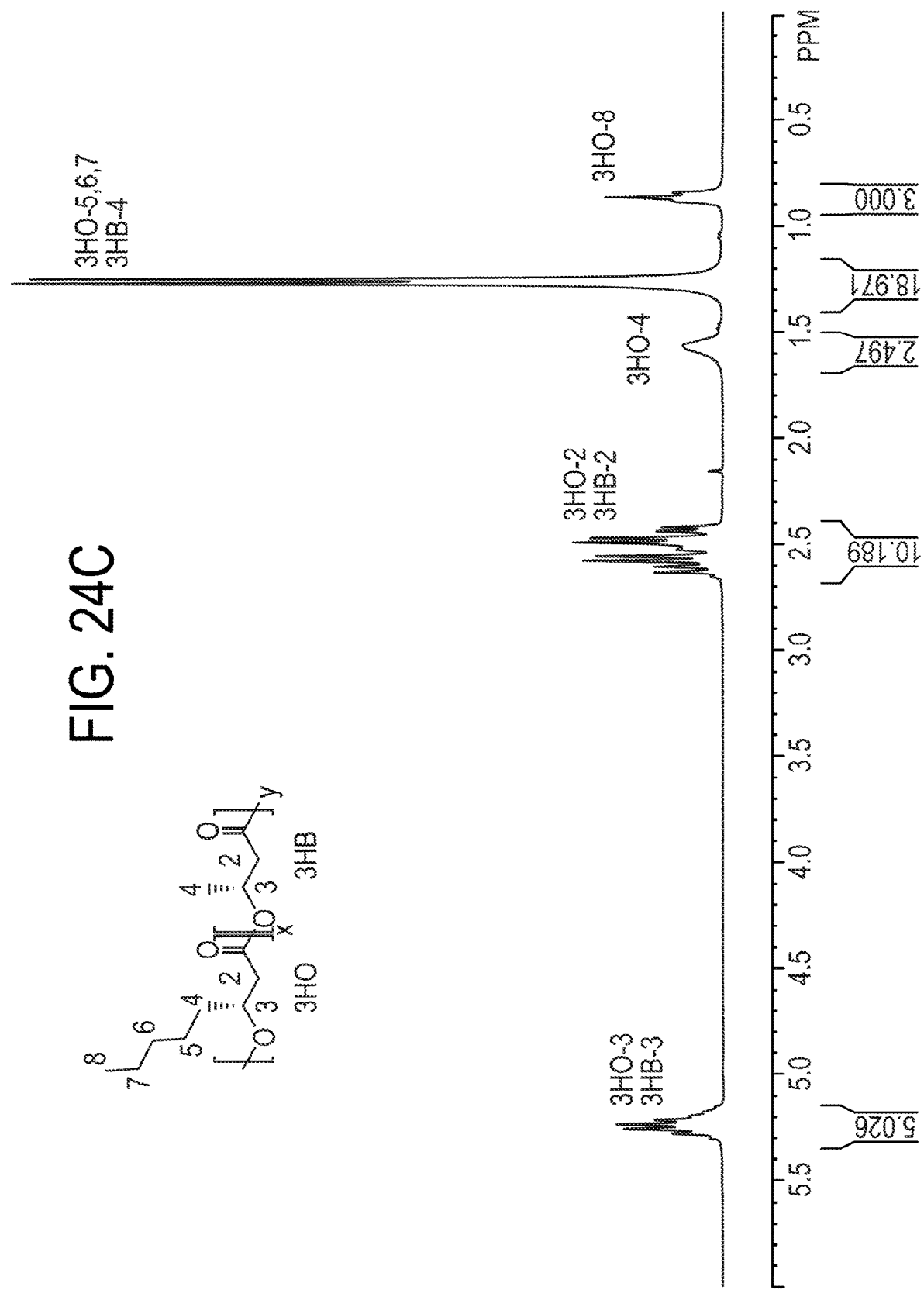

FIGS. 24A-C show $^1$H NMR spectra of poly[(R)-3-hydroxyoctanoate-co-(R)-3-hydroxybutyrate] containing 68.7% PHB prior to and after acetone fractionation. A, sample spectra prior to acetone fractionation. B, acetone soluble fraction. C, acetone insoluble fraction.

Figure 25:
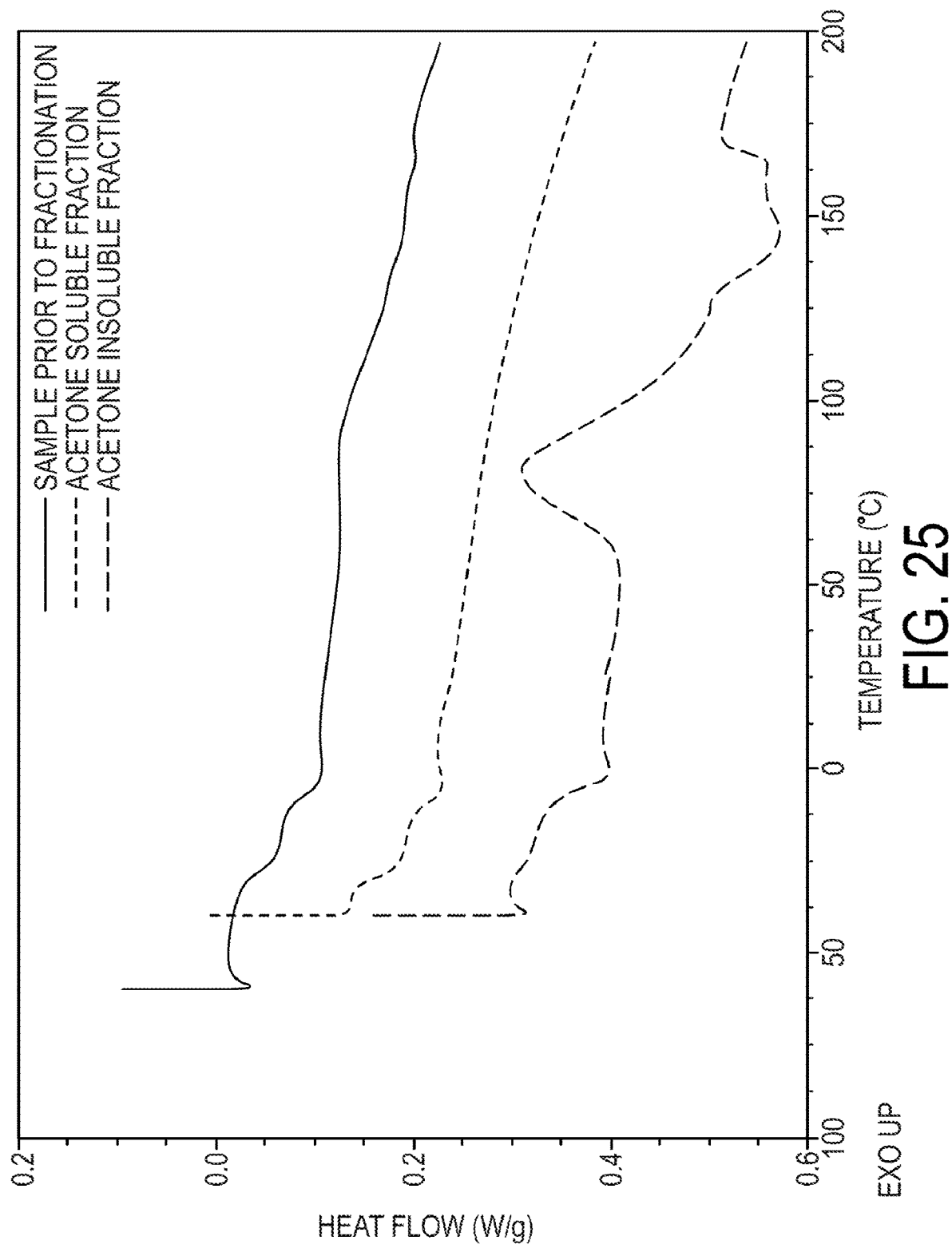

FIG. 24A shows a PHOHB sample made from a 15:85 C8:C4 substrate ratio and containing 68.7% PHB. FIGS. 24B and 24C shows the spectra of the sample after acetone fractionation. FIG. 24B is the acetone soluble fraction and was found to have 54.9% PHB, and FIG. 24C is the acetone insoluble fraction and was found to have 80.1% PHB. PHB homopolymer is insoluble in acetone, and finding it in such a high concentration (54.9%) in the acetone soluble fraction indicates that the PHOHB produced here is not a blend of PHO and PHB homopolymers but an actual copolymer. DSC was also used to check for any changes in thermal properties after acetone fractionation. The same samples used to generate FIGS. 24A-C were analyzed as described herein, and the results are shown in FIG. 25. The glass-transition temperatures, crystallization temperatures, and melting temperatures for these scans are summarized in Table 11.

TABLE 11

Thermal properties of poly[(R)-3-hydroxyoctanoate-co-(R)-3-hydroxybutyrate] containing 68.7% PHB before and after acetone fractionation

| Sample | $T_g$ (° C.) | $T_c$ (° C.) | $T_m$ (° C.) |
|---|---|---|---|
| unfractionated | −26.0/−6/24 | n.d. | n.d. |
| acetone soluble | | | |
| acetone insoluble | −27.1/−4.61 | 82.1 | 144 |

$T_g$, glass-transition temperature;
$T_c$, crystallization temperature;
$T_m$, melting temperature;
n.d., not detected.

FIG. 25 shows DSC results of poly[(R)-3-hydroxyoctanoate-co-(R)-3-hydroxybutyrate] containing 68.7% PHB before and after acetone fractionation. Scans were offset for clarity. The top scan is of the sample prior to acetone fractionation. The middle scan is the acetone soluble fraction. The bottom scan is the acetone insoluble fraction.

Statistical Analysis of Physical Properties Data

The correlations among the four physical property values generated for the PHOHB (Young's modulus, strain to failure, yield strength, and ultimate tensile strength) were very high (Table 10). Based on these correlations, it was assumed that further analysis of one of these sets of values would be nearly identical to analysis of the others. Analyses of variance tests were used to determine if the mean values for the physical properties of the polymers with different C8:C4 values were the same. Using both parametric analysis of variance after taking the natural logarithm of the data and a Kruskal-Wallace test, the values were found not to be identical (i.e., p-values for all variables for both analyses were <0.001).

To gain a better understanding of the relationship between the variables as the C8:C4 ratios changed, linear regression followed by further analysis of variance was used. Using the Young's modulus data as an example, the percent 3HO (C8) in the polymer was used as the "x" variable, and the natural logarithm of the physical property values were used as the "y" variable. Using the software program MINITAB, a plot for the linear regression described was generated for the Young's modulus experiments (FIG. 17). Analysis of variance was used again to test if the regression relationship is statistically significant. The p-value for this analysis was <0.001, indicating the relationship is statistically significant and the Young's modulus did decrease with increasing amounts of 3HO in the PHOHB polymers. This same process was repeated for ultimate tensile strength data as well (FIG. 18), and again the p-value for this analysis was <0.001, indicating the relationship is statistically significant.

Acetone Fractionation

Figure 19:
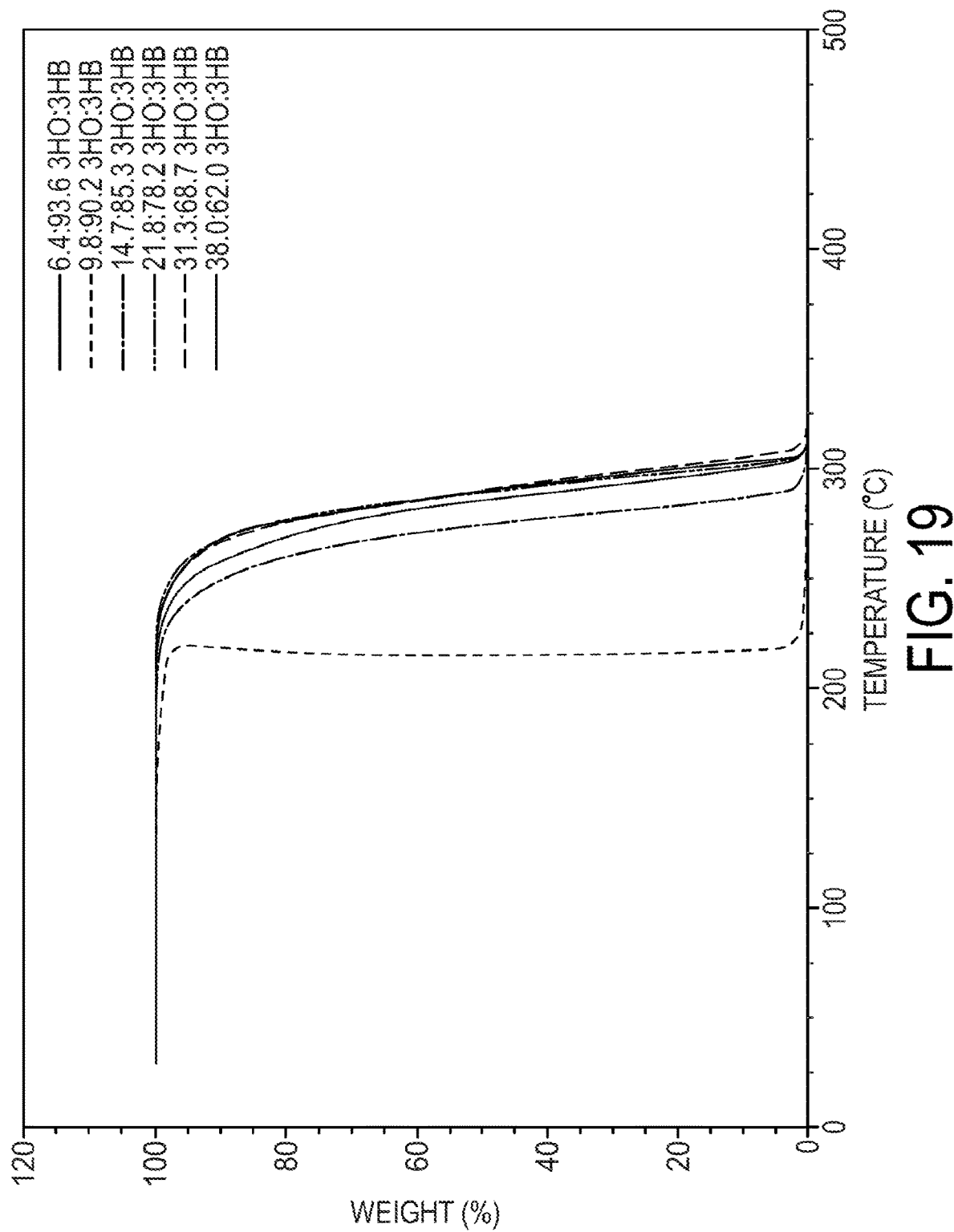
FIG. 19 shows TGA scans of various poly[(R)-3-hydroxyoctanoate-co-(R)-3-hydroxybutyrate] samples synthesized in E. coli LSBJ containing the pBBR-C1J4SII plasmid.

To determine if the PHA copolymers PHOHB synthesized in this study were copolymers and not blends of PHO and PHB, the samples were subjected to acetone fractionation. Films of PHOHB were placed in a 50 ml centrifuge tube with 20 ml of acetone and incubated at 50° C. with gentle rocking. Samples were allowed to cool to room temperature, and the liquid portion of the mixture was filtered with a 0.45 μm PTFE filter under vacuum. The remaining solid polymer was rinsed twice with a small volume (2-5 ml) of acetone both the filtrate (acetone soluble) and acetone insoluble fractions were allowed to dry. Samples were then subjected to $^1$H NMR analysis as described herein. An example of the spectra seen is displayed in FIG. 19.

Additional Examples of PHA Copolymer Production

Figure 32:
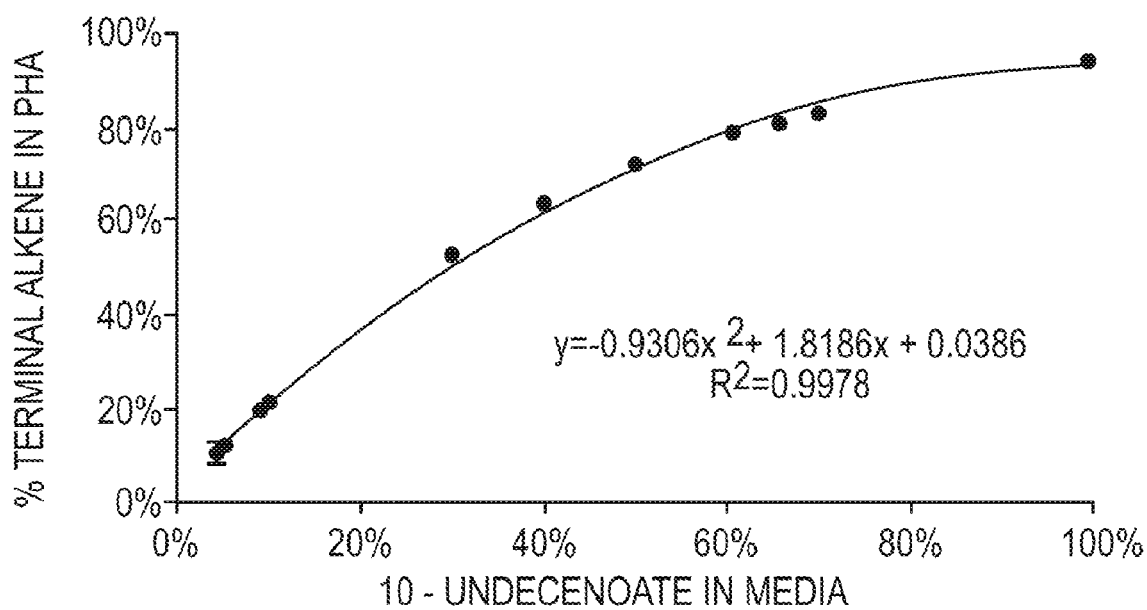

FIG. 32 shows the results of poly[(R)-3-hydroxy-10-undecenoate-co-(R)-3-hydroxyoctanoate] production in *E. coli* LSBJ harboring the pBBR-C1J4SII plasmid. The (R)-3-hydroxy-10-undecenoate repeating units were provided by 10-undecenoate, and the (R)-3-hydroxyoctanoate repeating units were provided by sodium octanoate. The relative concentration of fatty acid substrates was varied to demonstrate the corresponding change in terminal alkenes present in the polymer product (determined by NMR). This plot portrays the change in concentration of terminal alkenes in repeating units of PHAs as a function of starting concentration of 10-undecenoate relative to total fatty acid content.

Figure 33:
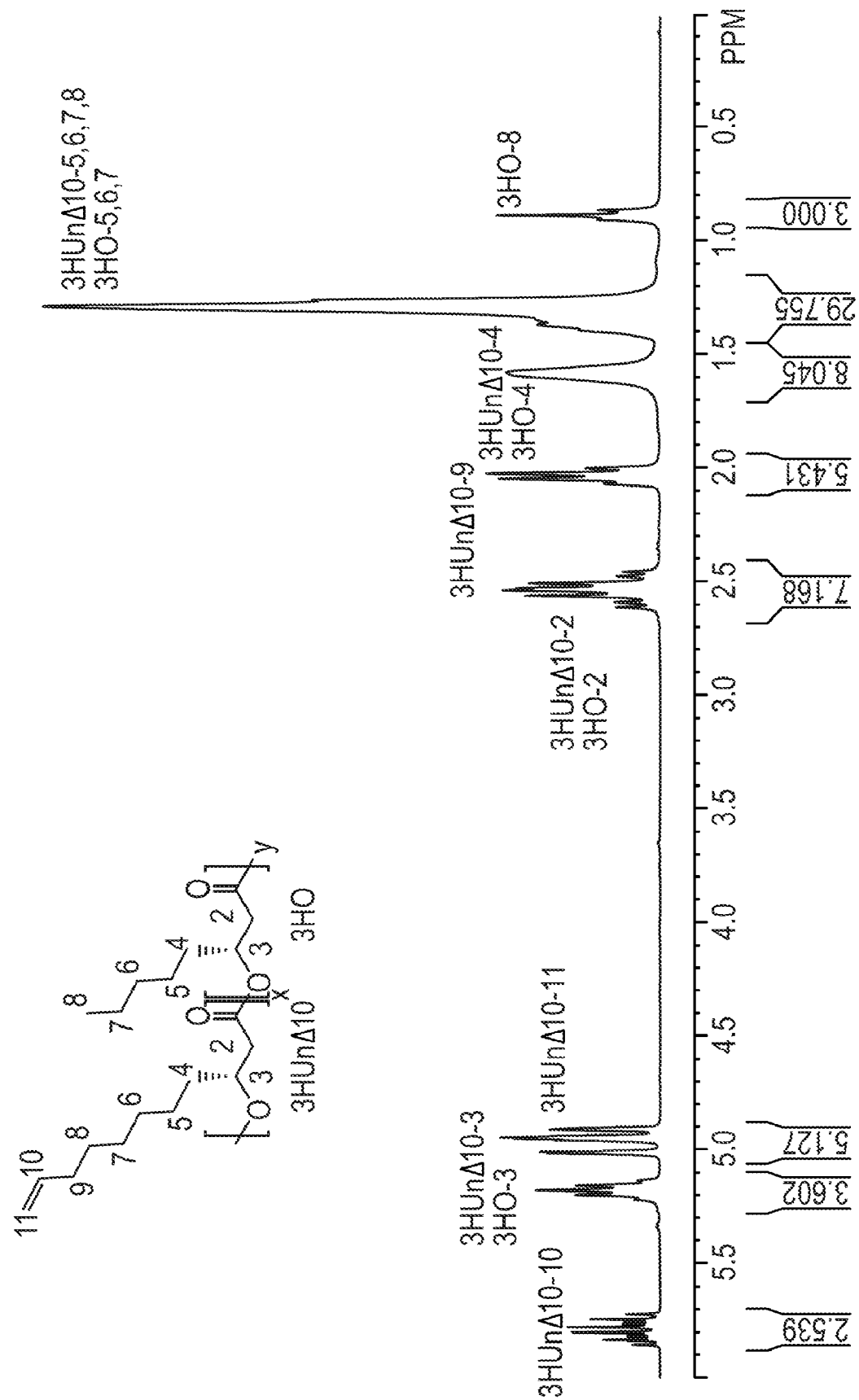

FIG. 33 shows a 300 MHz $^1$H NMR spectrum of a poly[(R)-3-hydroxy-10-undecenoate-co-(R)-3-hydroxyoctanoate] sample synthesized by *E. coli* LSBJ carrying the pBBR-C1J4SII plasmid. Cells were grown with 10-undecenoate and sodium octanoate at a mole ratio of 50:50 to generate this sample. 3HUnΔ10, (R)-3-hydroxy-10-undecenoate; 3HO, (R)-3-hydroxyoctanoate. Based on the peak integrations, it was determined that this polymer had a 3HUnΔ10:C8 mole ratio of 72.3:27.7.

The ratio of PHA to PLA in the copolymers produced is controlled in a manner similar to what has been established for PHA copolymers (see Example 2). Thus PHA-co-PLA copolymers are produced by the methods disclosed herein above with defined compositions, allowing for control over the material properties of next generation of biobased, biodegradable plastic materials.

Discussion

The *E. coli* LSBJ strain developed here in combination with the PHA production plasmid pBBR-C1J4SII allows strict control of repeating unit composition of PHAs for both MCL and SCL PHAs. The desired PHAs can be synthesized based simply on selecting a fatty acid substrate of equal carbon length. As shown in Table 3, PHAs were synthesized in sizes ranging from four to twelve carbons. Because of the native enoyl-CoA hydratase knockouts, the resulting PHAs were near homopolymers based on GC, GC-MS, and NMR analysis. GC-MS analysis found detectable amounts of repeating units different in carbon lengths than the starting fatty acid substrate, but this is likely due to impurities of the substrates and media (Table 3).

*E. coli* LSBJ is particularly useful for MCL PHA production from fatty acids. The parent strain, *E. coli* LS5218, is known to have increased uptake and metabolism for a broad range of fatty acids without the need for transcriptional induction of the appropriate fad genes by FadR (17,18). The PhaJ4 and PhaC1(STQK) introduced to synthesize the PHAs have high activity towards MCL substrates. This allowed for the strain to generate MCL PHAs at 25% cell dry weight or greater (Table 3).

Although the system created here was designed with MCL PHA repeating unit control in mind, control can also be extended to SCL PHAs. The advantages of *E. coli* LSBJ extend to SCL sized fatty acids, and thus PHB was synthesized from sodium butyrate. This was expected as the uptake for shorter fatty acids does not need to be induced in this strain (18), and the PhaJ4 and PhaC1(STQK) enzymes selected for PHA synthesis have reported or inferred activity for four carbon substrates (21,22,26). The PHB yield was much lower than the MCL PHAs. This could be because of enzyme substrate specificity favoring MCL substrates.

This system offers the broadest range of repeating unit control of PHAs in a single organism. Other work has been reported to control repeating unit composition in *Pseudomonas putida* KT2442 (8). The polymer yields here were lower compared to the *Pseudomonas* system developed by Wang et al., but the *Pseudomonas* system was unable to synthesize homopolymers with repeating units greater than seven carbons. The *E. coli* LSBJ system developed in this study was shown to maintain repeating unit control up to and including repeating units of twelve carbons. The size limits for repeating unit control of this system have not been determined as of this writing.

Figure 14A:
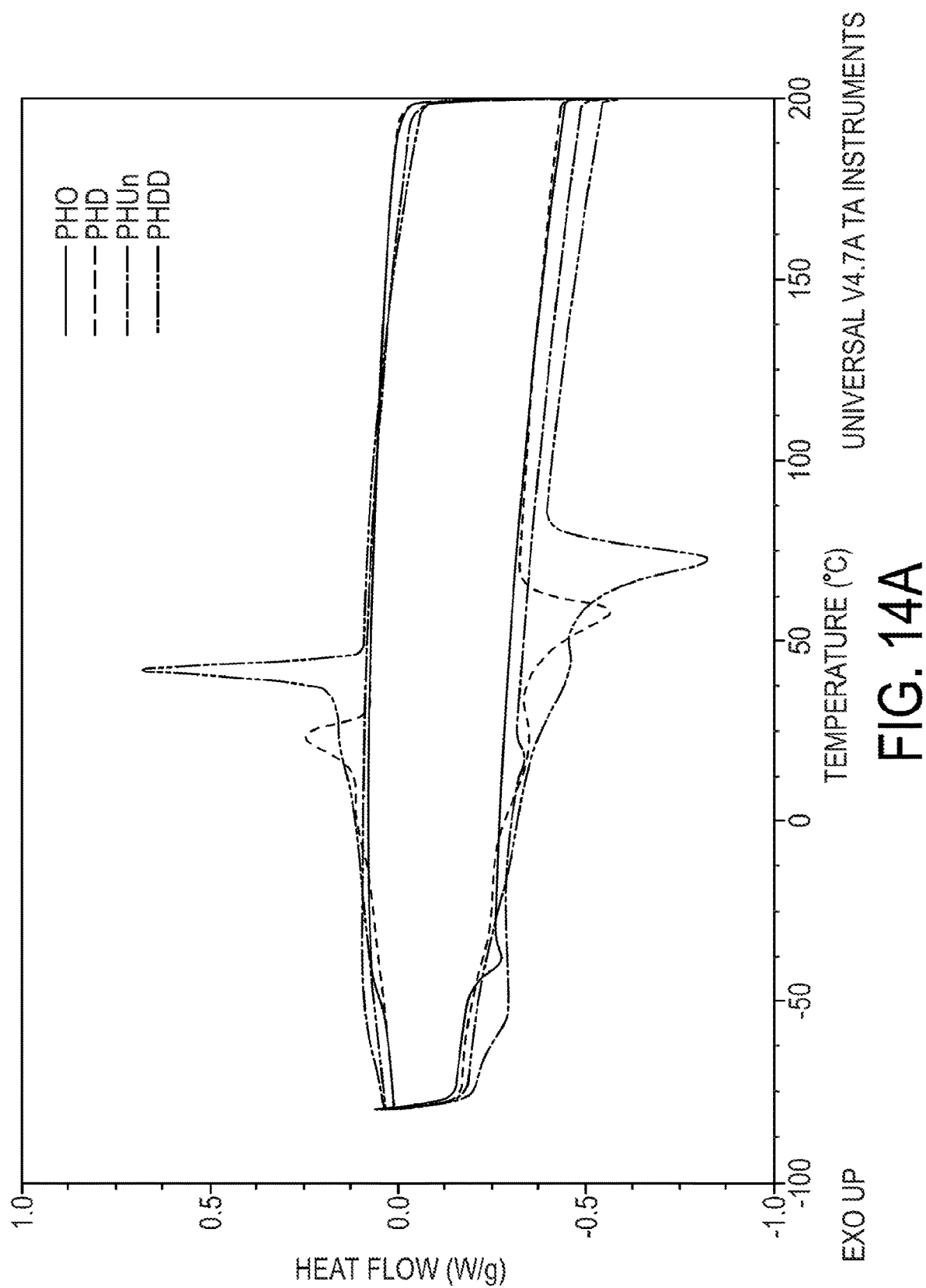
Figure 14B:
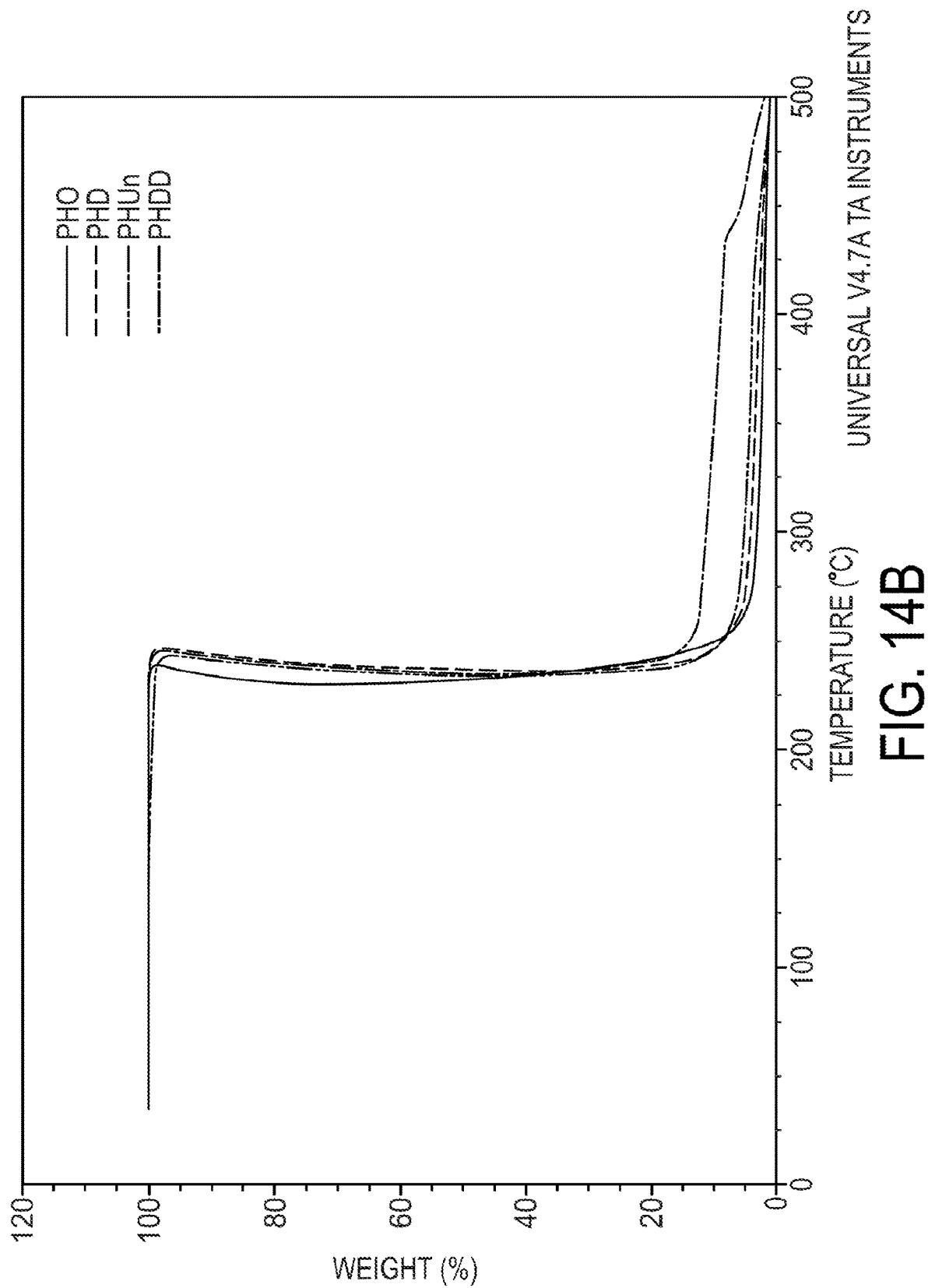
Figure 15:
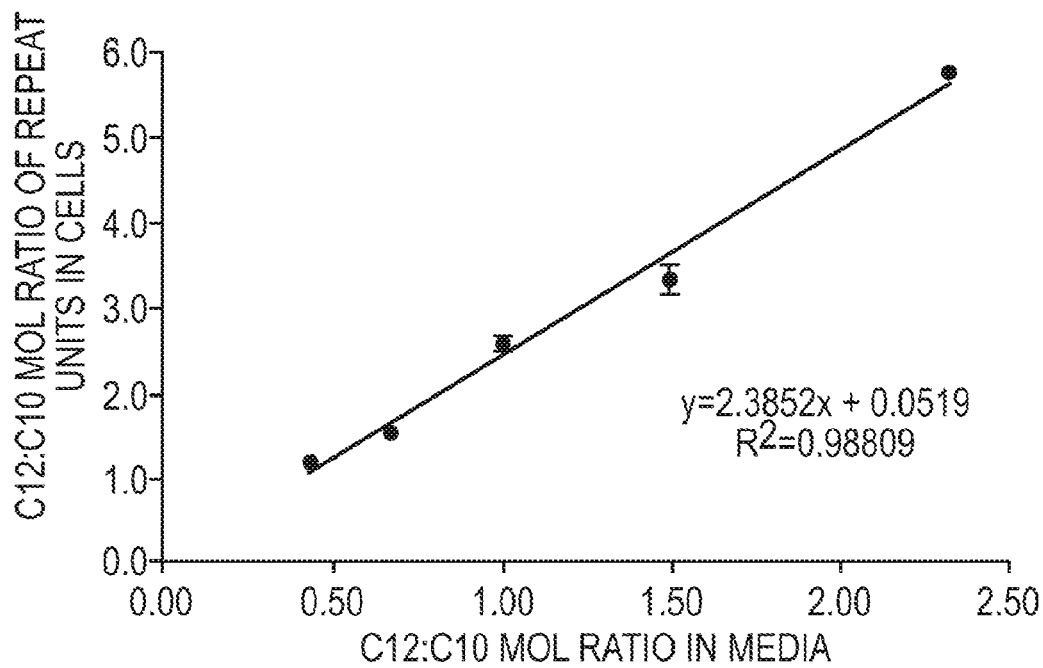
Figure 16:
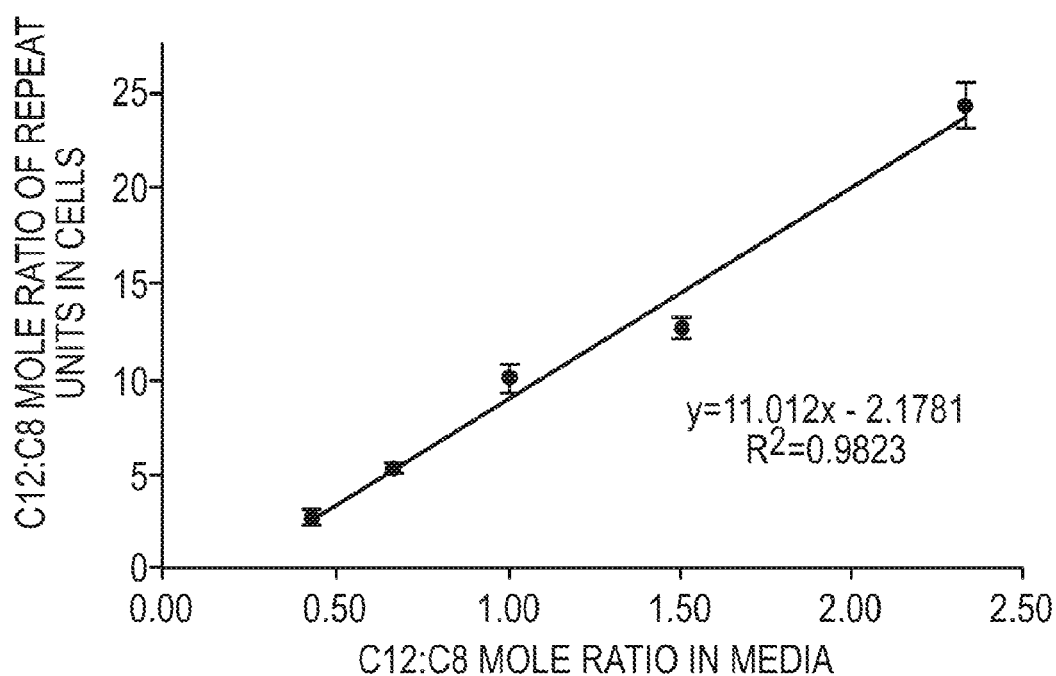

The thermal properties of the MCL PHAs produced here have similarities and differences when compared to other works that have produced MCL PHA homopolymers (8,9). Poly(3-hydroxyoctanoate) (PHO), for example, showed a $T_g$ of −42.1° C., which is lower than other works producing polymers of ≥98 mol % PHO (8,9). No melting temperature was seen here for PHO, which is not the case for reports of the other studies with ≥98 mol % PHO polymers (8,9). However, the other studies report very different melting temperatures. The study by Wang et al. reports a melting temperature of 66.06° C., but a melting endothermic peak cannot be seen on the DSC curve (8). The study by Rai et al. reported a range of melting temperatures between 39° C. and 50° C., but DSC curves are not presented (9). DSC curves for this work are shown in FIGS. 14A-B. There are many differences in these works for producing, purifying, and characterizing the polymers, which may account for the lack of consistency in reported thermal properties of PHO homopolymers.

Another MCL PHA homopolymer that has been synthesized before this work and was produced here was poly(3-hydroxydecanoate) (PHD) (7). Both the work presented here and the work by Liu et al. report glass transitions between −37° C. and −40° C. The previously produced PHD homopolymer had a reported melting temperature of 72.2° C. compared to the melting temperature of 57.7° C. for the PHD produced in this work. Once again, differences in synthesis, purification, and characterization methods could play a role in the differences in reported thermal properties.

More MCL PHA homopolymers need to be synthesized and characterized to determine if melting, crystallization, and glass transition temperatures can be predicted based on repeating unit size in PHAs. The $T_g$ for these polymers may decrease with increasing side chain length as has been suggested by another work developing MCL PHA homopolymers (8). If this is true, the glass-transition temperature for poly(3-hydroxydodecanoate) (PHDD) may be near or below the −80° C. minimum of the DSC scans performed. There was no definitive trend in the degradation temperatures of all the polymers tested (Table 4 and FIGS. 14A-B). The thermal properties and trends of polymers here did not coincide with the properties of the polymers reported by Wang et al (8). However, this could be the result of differing polymer purification, polymer storage conditions, molecular weights, and/or experimental conditions for DSC and TGA.

The molecular weights varied for the MCL PHAs, and the polydispersities determined by GPC ranged from 1.6 to 3.1 (Table 4). The molecular weights ($M_n$) were varied with PHD and PHO having noticeably larger molecular weights than PHUn and PHDD. The PHO molecular weight ($M_n$) and polydispersity are comparable to previous work with this polymer (9). The PHD molecular weight ($M_n$) is more than twice as small as a previous work producing PHD homopolymer, and the polydispersity is greater in this example (7). The PHUn and PHDD homopolymers have not been synthesized bacterially prior to this work.

Comparison of polymer molecular weights and polydispersities from this work to other works is difficult due to the differences in bacterial production. Other works have relied on native *Pseudomonas* PHA synthesis enzymes. The polymers here were made in *E. coli* expressing an enzyme with naturally broad substrate specificity (PhaJ4) and an enzyme with engineered broad substrate specificity [PhaC1(STQK)]. The substrate specificities of the PHA synthesis enzymes, particularly the PHA synthase, could have a significant effect on the molecular weights of the polymers. Some in vitro characterization of the substrate specificity of the PhaC1 (STQK) synthase used in this example is available but limited to substrates with four to ten carbons (54). Because the relationship of substrate specificity to molecular weight of the polymer produced by PHA synthase enzymes is not completely defined, there is not sufficient material to draw conclusions as to why there are differences in the molecular weights of the PHA polymers produced in this example. However, the differences in the substrate specificity of engineered and native PHA synthases may be responsible for the differences in the molecular weights of polymers.

Figure 1:
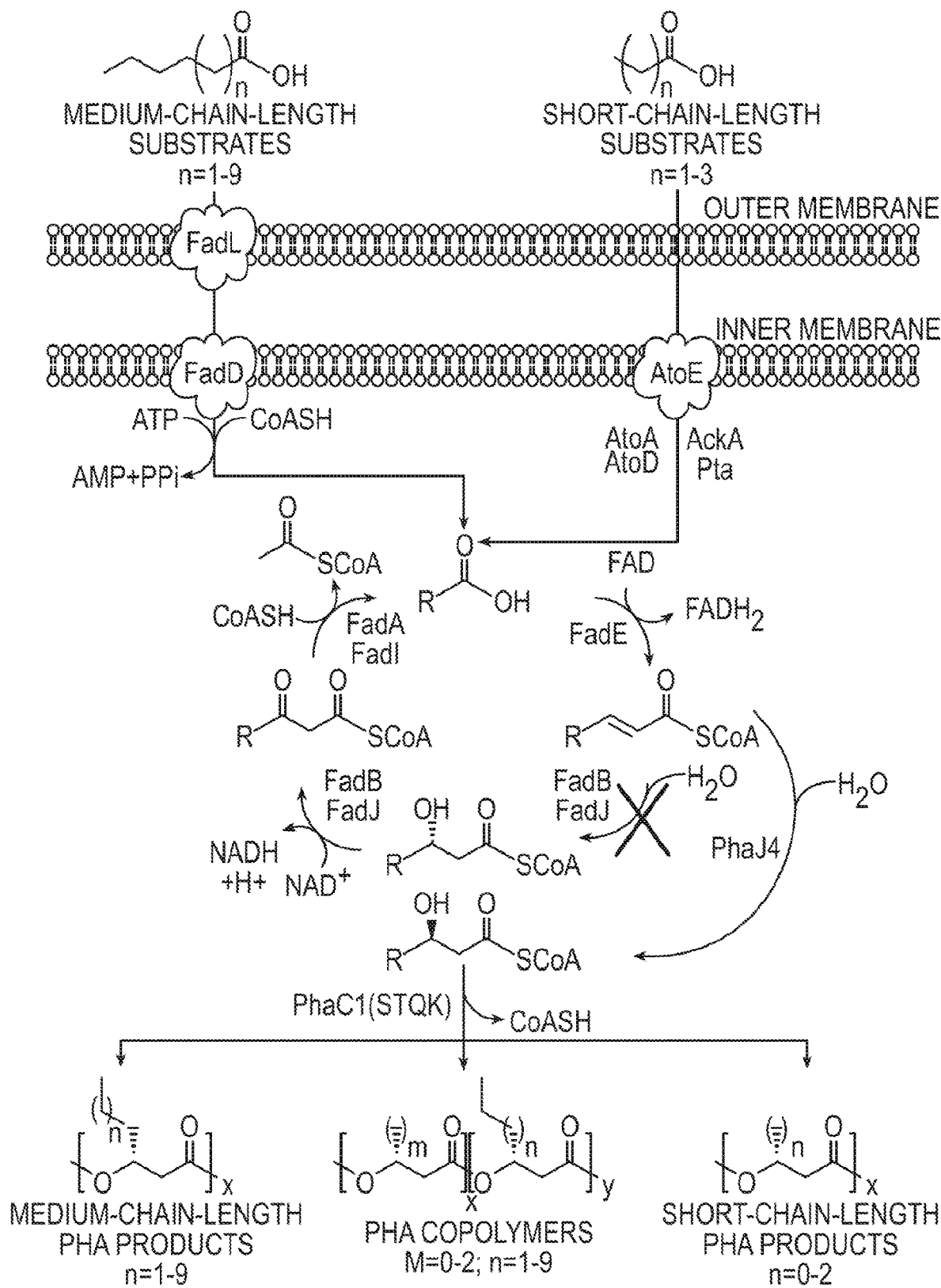
Figure 2A:
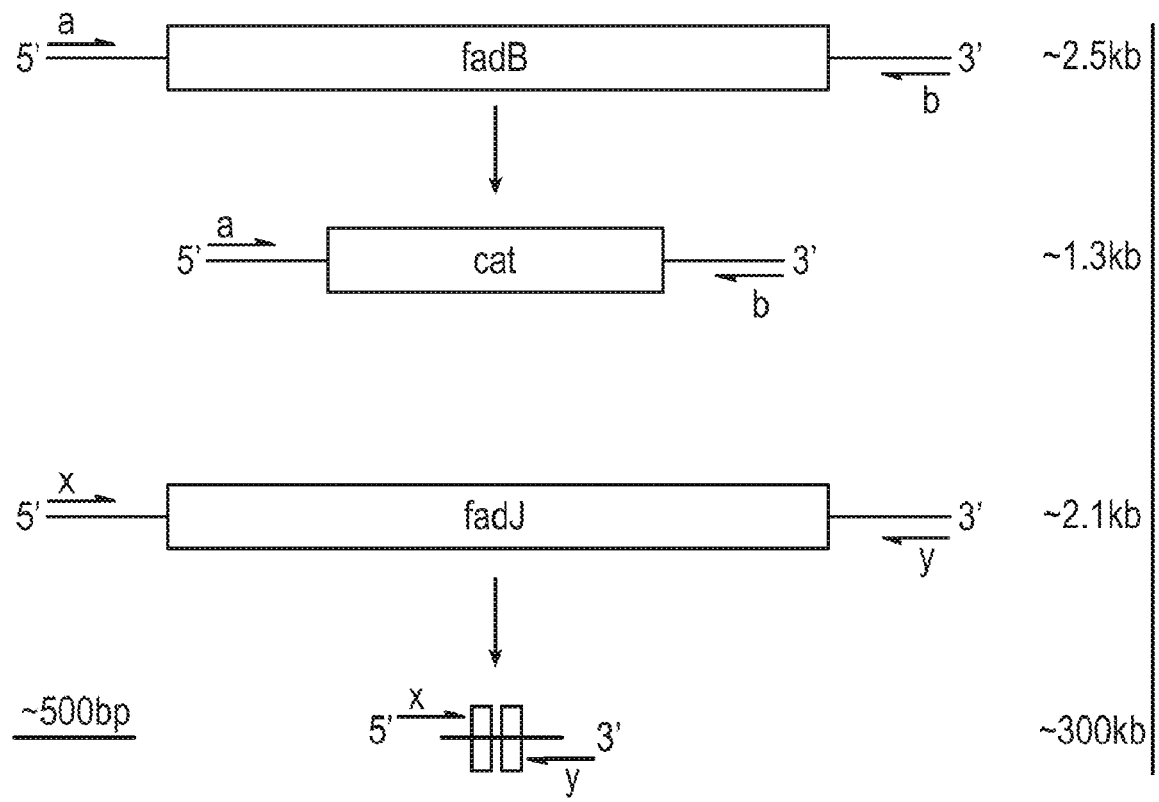
Figure 2B:
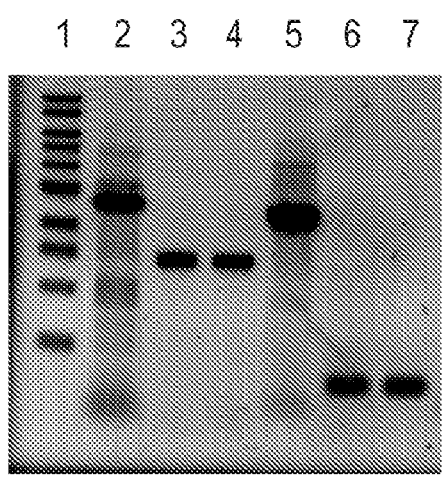
Figure 3:
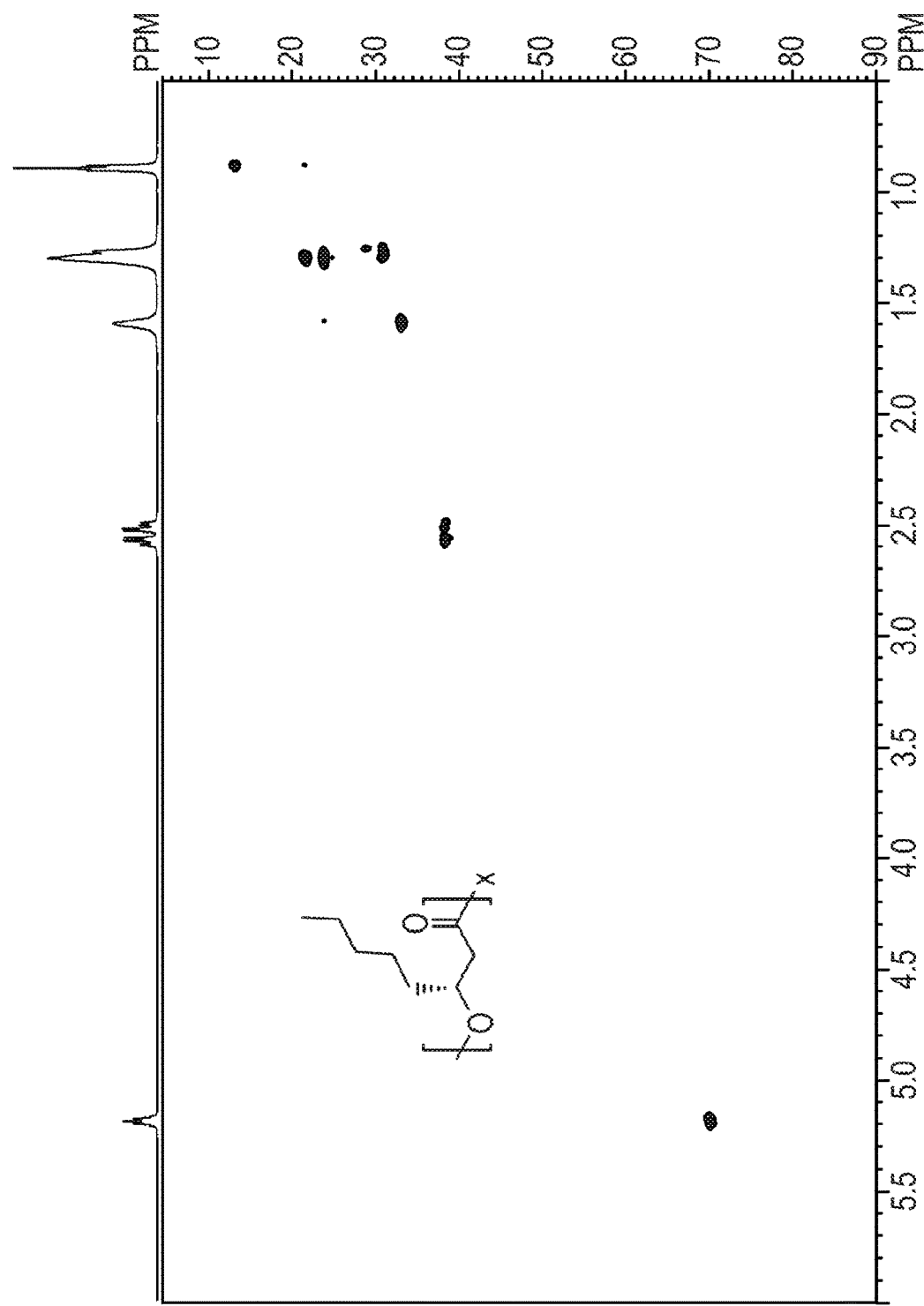
Figure 4:
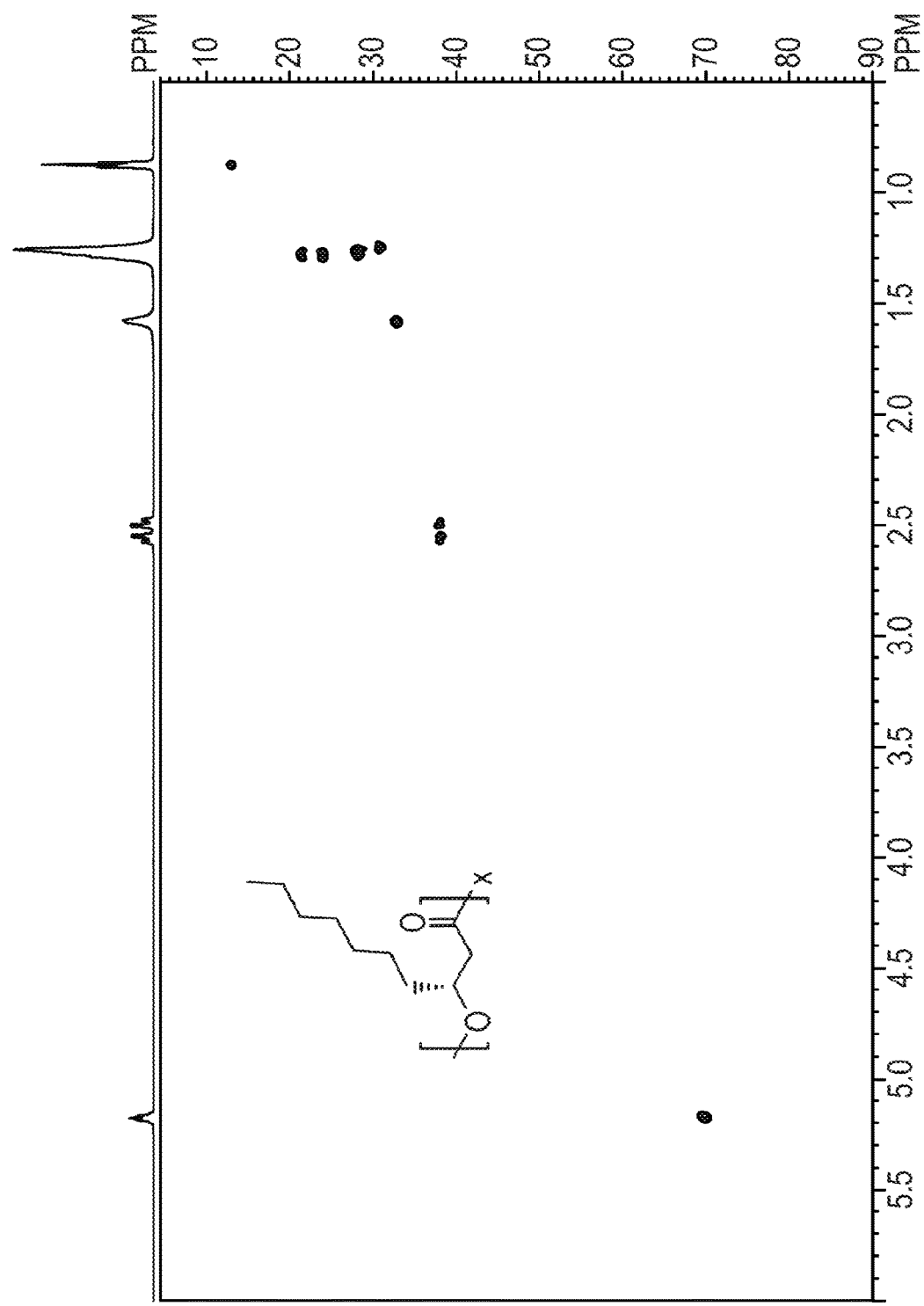
Figure 5:
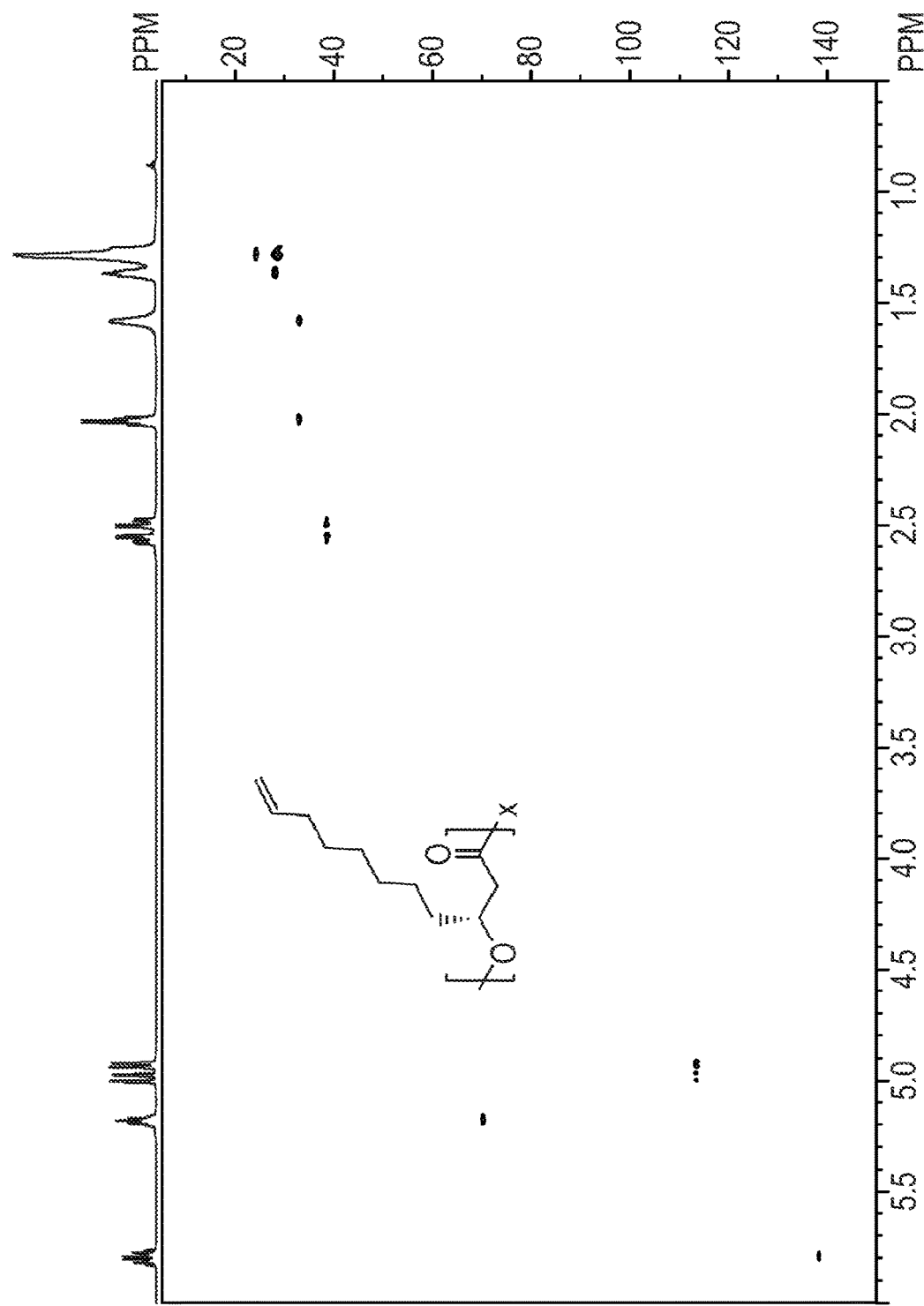
Figure 6:
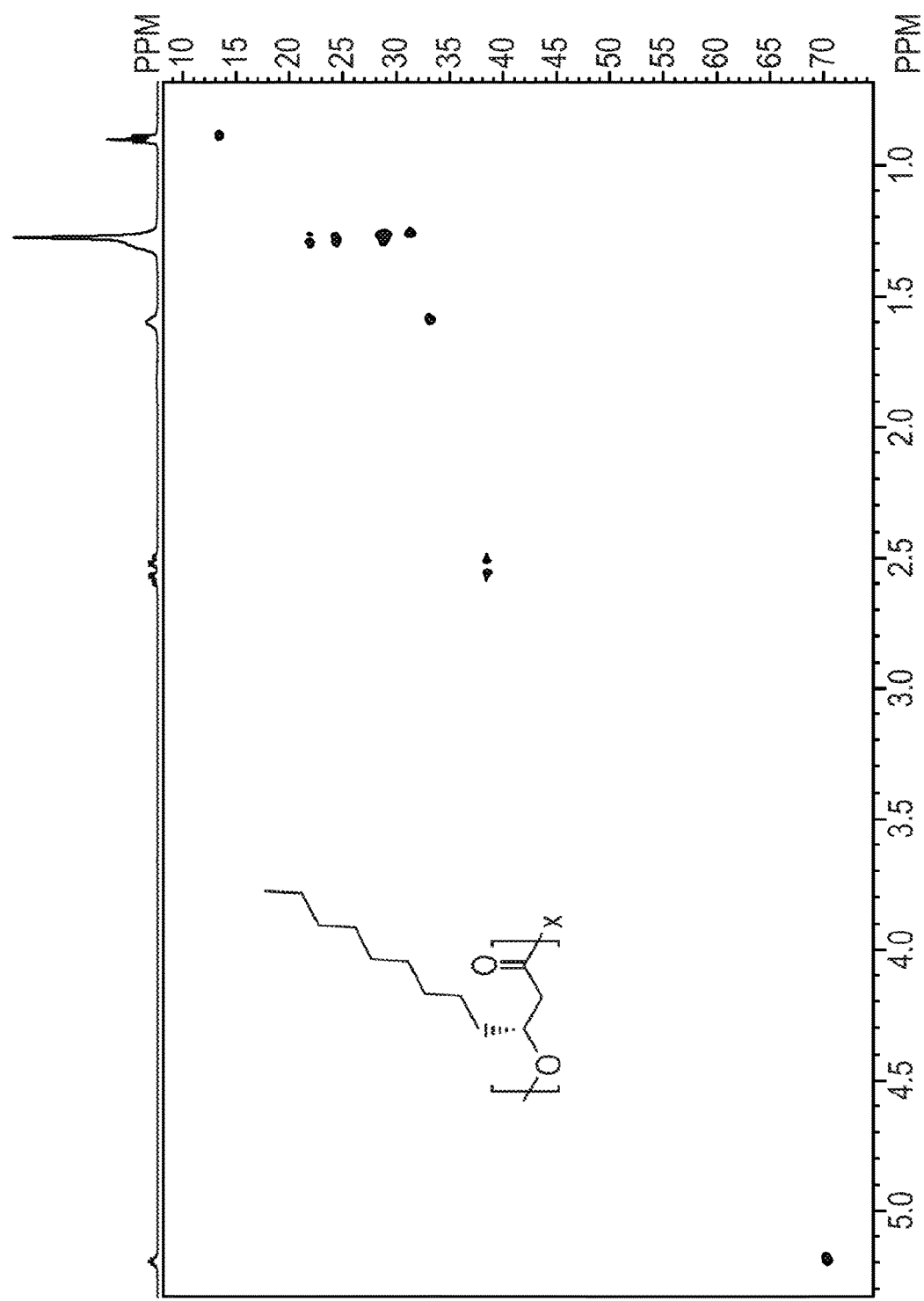
Figure 7A:
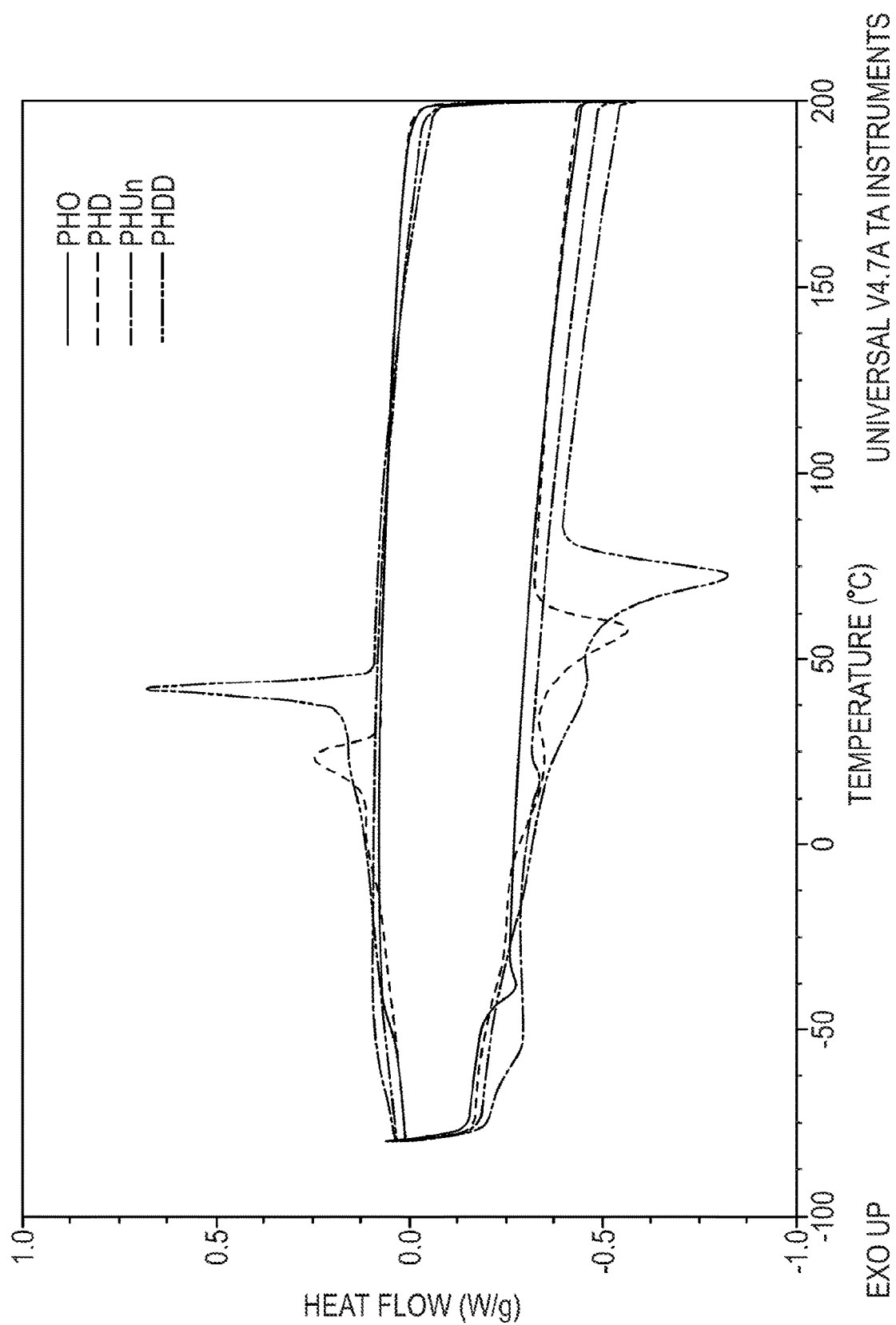
Figure 7B:
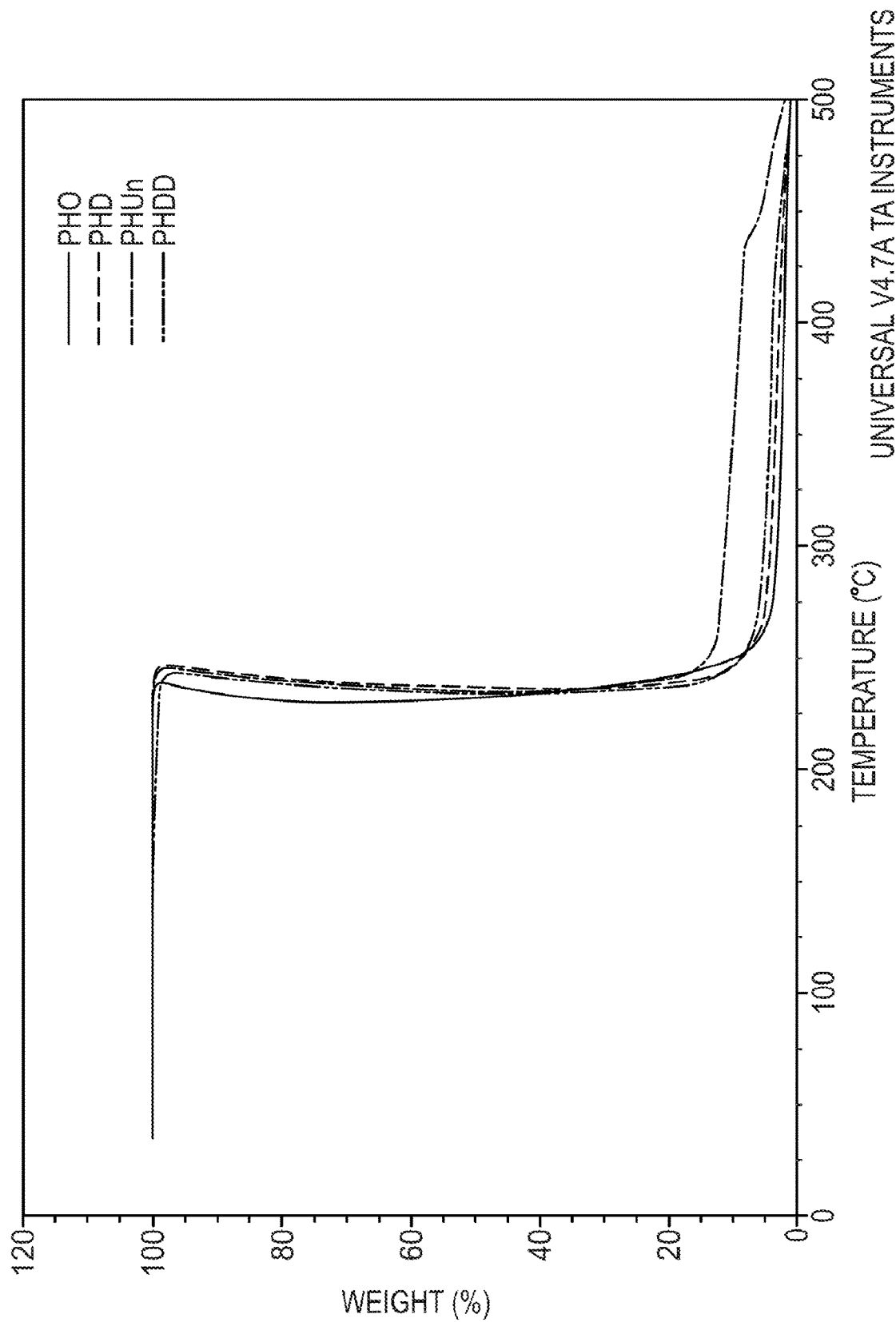
Figure 8:
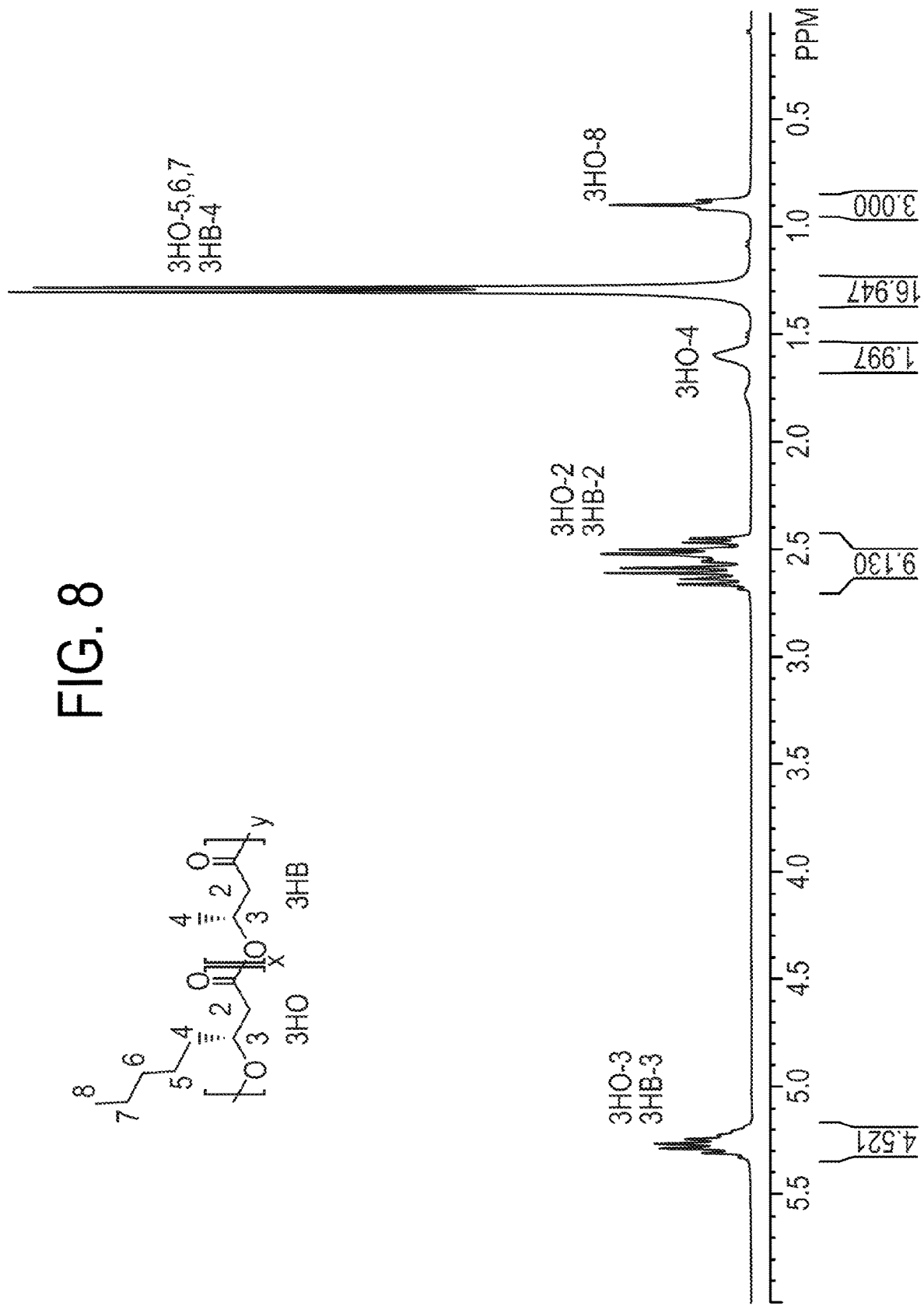
Figure 9A:
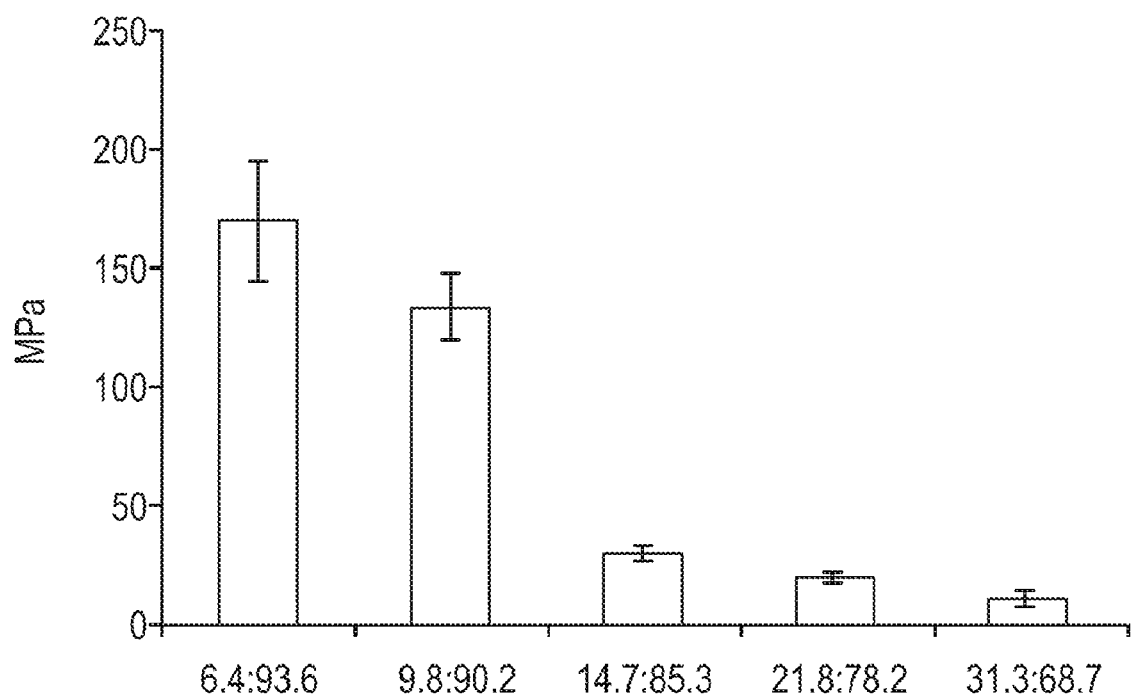
Figure 9B:
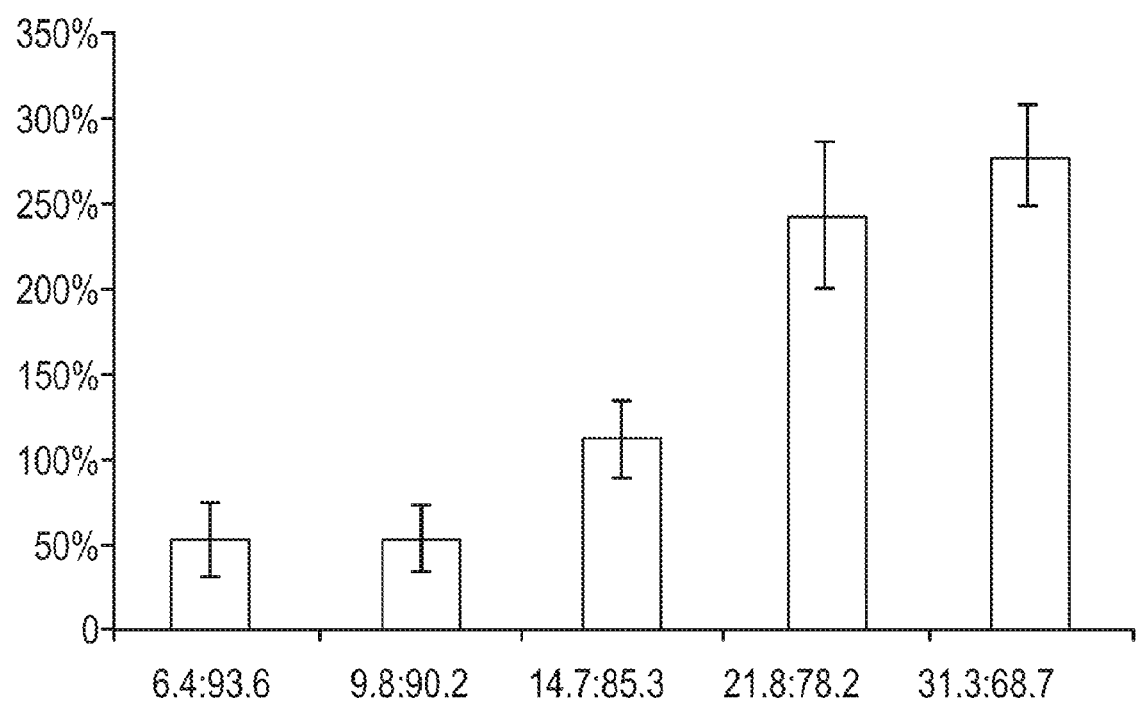
Figure 9C:
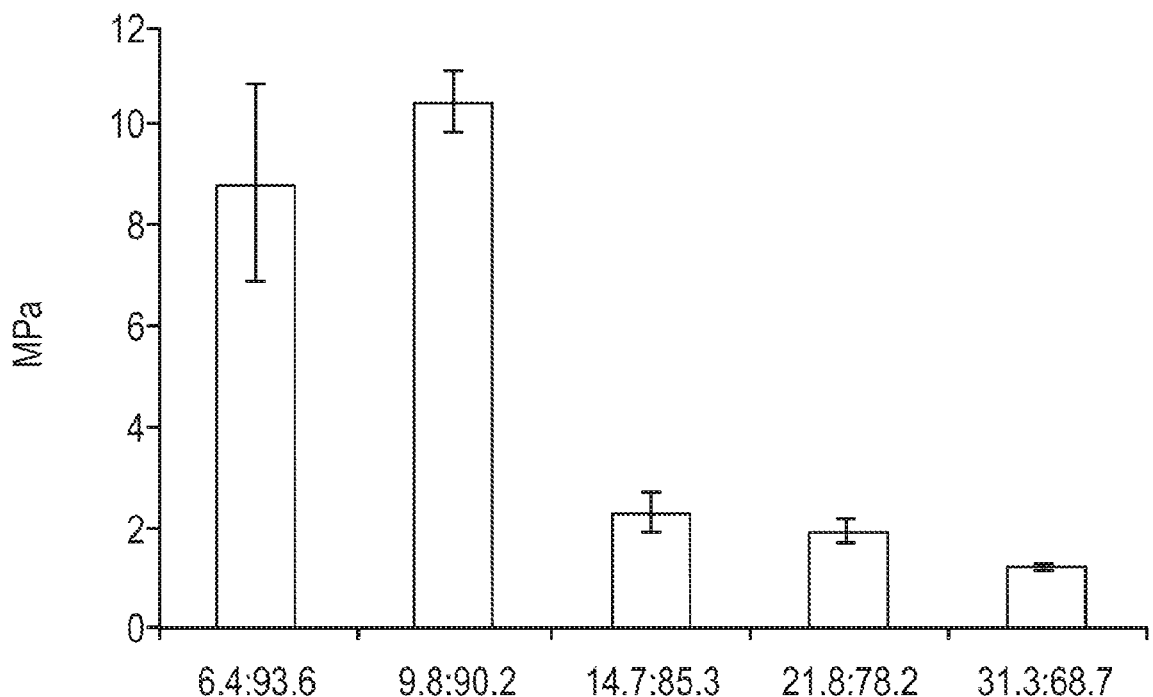
Figure 9D:
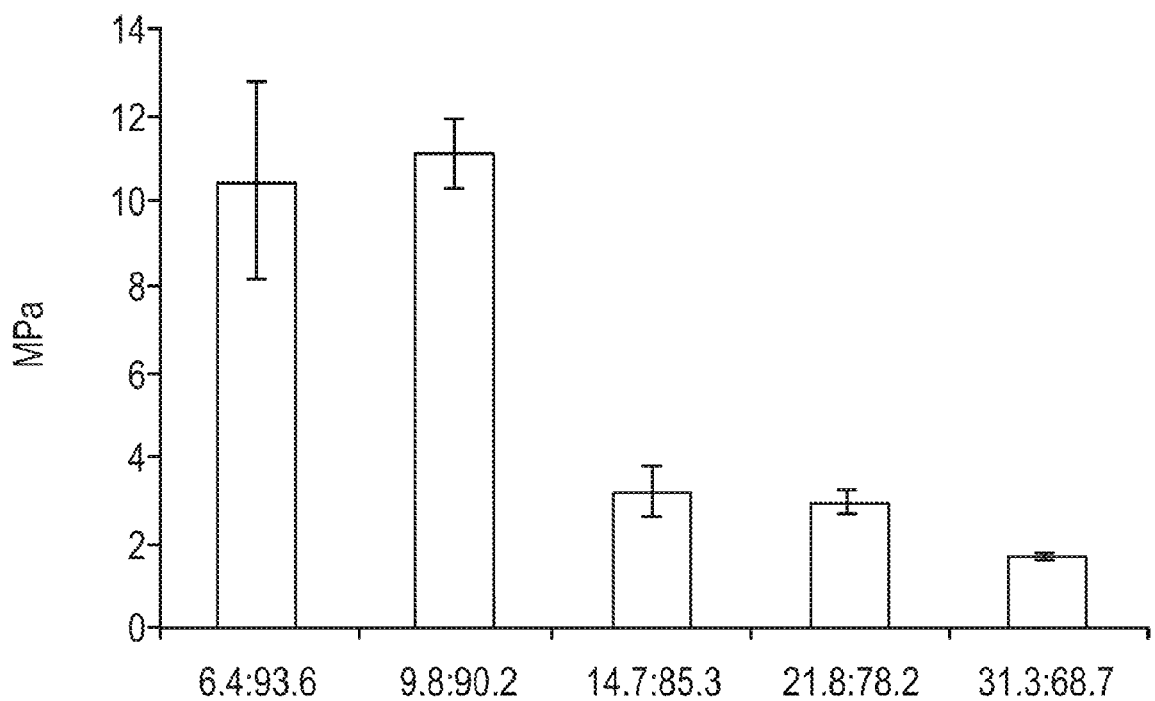
Figure 10:
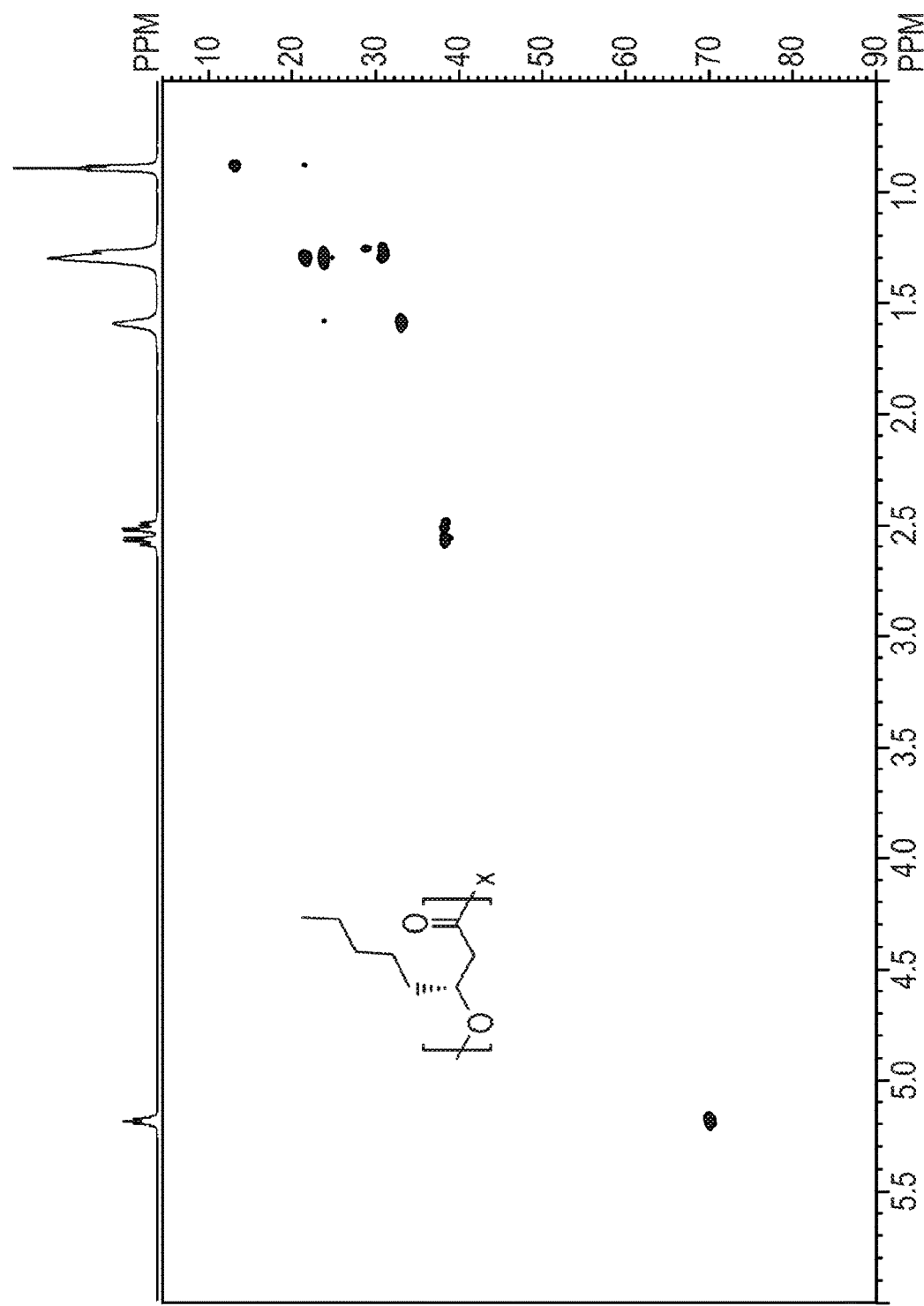
Figure 11:
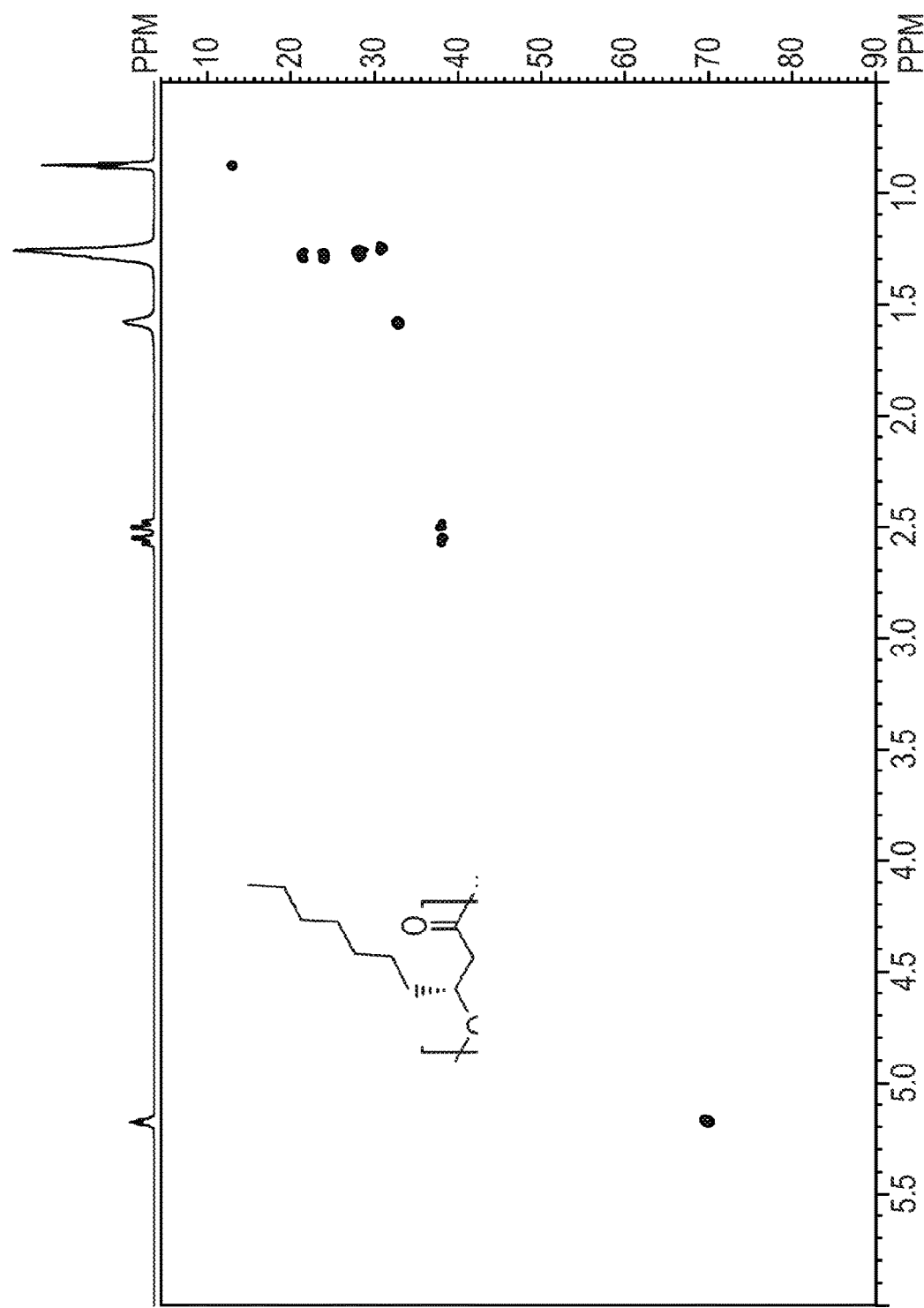
Figure 12:
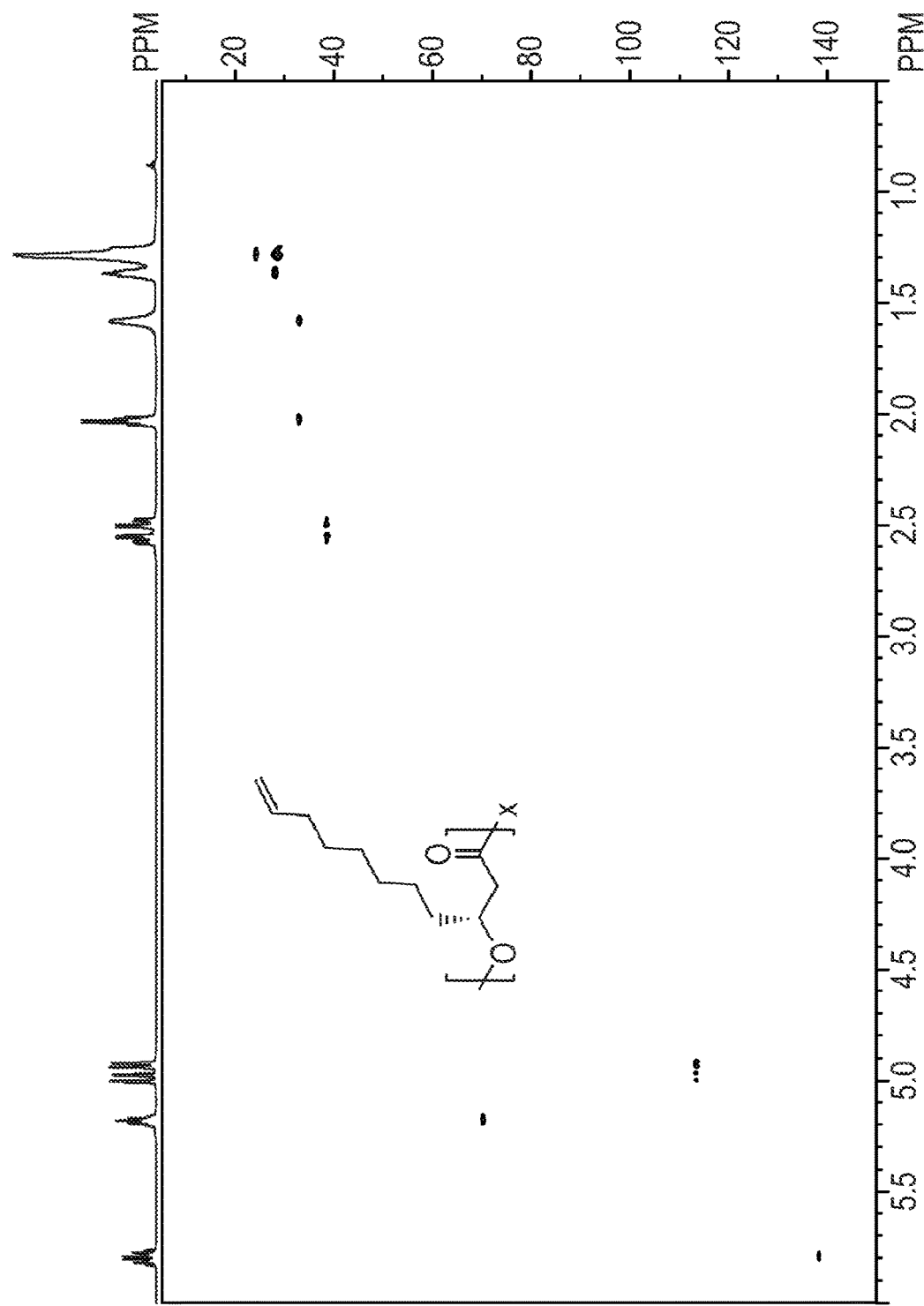
Figure 13:
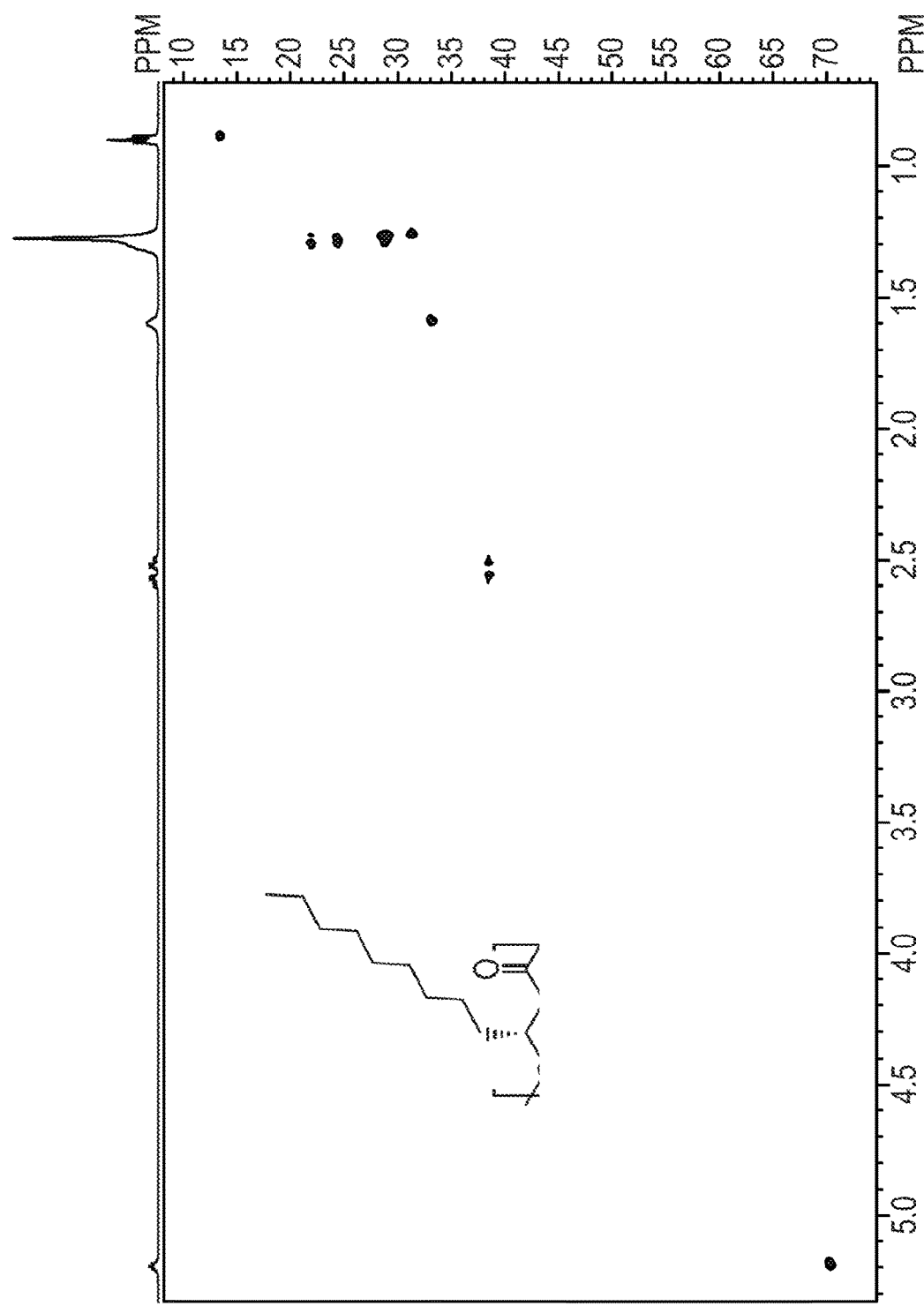

The strain *E. coli* LSBJ was developed to allow for repeating unit control in PHA biosynthesis. Knockouts of the genes fadB and fadJ created a dam in the β-oxidation pathway (FIG. 1). Instead of being degraded, fatty acid substrates were converted to PHAs by PhaJ4 and PhaC1 (STQK). This allowed for control of repeating unit composition simply by selecting the fatty acid that matches the desired repeating unit in carbon length. This strain successfully demonstrated repeating unit control in PHAs with repeating units of four, eight, ten, eleven, and twelve carbons. This represents the first bacterial strain to achieve such diversity in repeating unit control of PHAs.

After characterization of polymers synthesized from a single fatty acid substrate was complete, *E. coli* LSBJ was used to synthesize PHA copolymers from two fatty acid substrates. Shown here is a demonstration of the first bacterial system to produce PHA copolymers with specifically defined and tunable repeating unit ratios. Precise control was shown for both MCL and SCL-co-MCL PHA copolymers by calibrating various feedstock ratios against specific copolymer repeating unit ratios as described herein, and by successfully and accurately producing copolymers with preselected repeating unit ratios within the calibrated range. This was completed with both the MCL PHDDHD copolymer by synthesizing a 65:35 C12:C10 copolymer and the SCL-co-MCL PHOHB copolymer by synthesizing a 10:90 C8:C4 copolymer.

It has been reported that SCL-co-MCL PHAs have physical properties that are similar to petroleum-based polymers such as polypropylene and polyethylene (see Table 12) (1,10,55). The thermal and physical properties of the series of PHOHB copolymers synthesized in this study were examined to compare our SCL-co-MCL PHA with common petroleum-based plastics. The degradation temperatures determined by TGA experiments did not reveal a notable trend (Table 9 and FIG. 19). During DSC experiments, however, two glass-transitions became apparent as the concentration of the 3HO repeating units increased in the PHOHB copolymers. The glass-transition peak at the lower temperature decreased with increasing amounts of 3HO present in the polymer (Table 9), approaching but not reaching previously reported values of PHO (44,53). It may be that as the 3HO content continues to increase, the polymer comes to progressively resemble the PHO homopolymer more and more closely. The second glass-transition temperature was between −4.5° C. and −6.3° C. Although the trend is not definitive, this transition may be moving farther away from the glass-transition of the PHB homopolymer as the amount of 3HO in the PHOHB copolymer increases.

TABLE 12

Comparison of thermal and physical properties of PHA samples produced in this study to common polymers

| Polymer | Melting temperature (° C.) | Glass-transition temperature (° C.) | Young's modulus (MPa) | Tensile strength (MPa) | Strain to failure (%) | Reference |
|---|---|---|---|---|---|---|
| PHB | 171 | 4.50 | 185 | 5.3 | 6.0 | This study* |
| PHOHB (6.4% 3HO) | 158 | −1.42 | 170 | 10.5 | 53 | This study |
| PHOHB (14.7% 3HO) | 159 | −2.23 | 31.5 | 3.2 | 110 | This study |
| PHOHB (31.3% 3HO) | n.d. | −26.0/−6.24 | 12.0 | 1.7 | 230 | This study |

TABLE 12-continued

Comparison of thermal and physical properties of PHA samples produced in this study to common polymers

| Polymer | Melting temperature (° C.) | Glass-transition temperature (° C.) | Young's modulus (MPa) | Tensile strength (MPa) | Strain to failure (%) | Reference |
|---|---|---|---|---|---|---|
| Polypropylene | 176 | −10 | 1700 | 38 | 400 | (2) |
| Low-density polyethylene | 130 | −30 | 200 | 10 | 620 | (2) |

PHB, poly[(R)-3-hydroxybutyrate];
PHOHB, poly [(R)-3-hydroxyoctanoate-co-(R)-3-hydroxybutyrate];
n.d., not detected.
*PHB was synthesized from sodium butyrate as described herein.

The two glass-transition temperatures may also be indicative of block-like sequences of PHB and PHO within the polymer or mixtures of homopolymer PHO and PHB. To investigate this, various PHOHB samples were subjected to acetone fractionation given that PHB is insoluble in acetone, and PHO is soluble. A portion of each sample dissolved in the acetone, and the soluble and insoluble fractions were analyzed by $^1$H NMR spectroscopy. We found evidence of both PHO and PHB in each fraction for each PHOHB sample tested. Therefore, for there to be PHB in the acetone soluble fraction, we believe it must be covalently bound to PHO. Also, the PHO that did not dissolve in acetone must likewise be attached to a large fraction of PHB. The different fractions had very different repeating unit compositions (55% PHB to 45% PHO for acetone soluble copolymer, 80% PHB to 20% PHO for acetone insoluble copolymer) than prior to the fractionation, meaning there is a mixture of different copolymers that comprise the entire polymer population.

The melting and crystallization characteristics of the PHOHB copolymers were also sensitive to changes in the repeating unit ratios. The crystallization temperatures increased with increasing amounts of 3HO and moved away from reported values of approximately 51° C. for PHB (2,29).

When the amount of 3HO in the copolymer reached 31.3 mol %, a crystallization event was no longer observed in DSC experiments. The same absence was observed for samples with 3HO concentrations above 31.3 mol %. Below this mole percentage of 3HO, the melting temperatures of the copolymers were consistently slightly below 160° C. Although there was no obvious trend for the differences in melting temperatures, for those polymers where melting events were observed, all melting temperatures fell below what has been observed by us and others for PHB (see references and Table 5) (2,4,29,40) and were at least 50° C. below the degradation temperatures. The differences observed for melting temperatures and crystallization temperatures have important ramifications for polymer processing. It is highly desirable to have polymers with melting temperatures far below the degradation temperature and crystallization temperatures closer to melting temperatures to improve the residence time during polymer processing. Overall, the results summarized in Table 9 establish an ability to calibrate and select for specific thermal properties that may be desired in the context of a given application.

In addition to demonstrating control over thermal properties, this system allows for specific physical properties to be selected when synthesizing these biodegradable copolymers. The tensile strength analyses showed that statistically relevant trends existed for the Young's modulus, ultimate tensile strength, yield strength, and elongation to break as functions of the ratio of 3HO to 3HB in the PHOHB copolymers (FIGS. 9A-D). The PHOHB sample that was produced after the initial copolymers, which was designed to have a 10:90 C8:C4 ratio, had physical properties that followed the developed trends. Therefore, we conclude that PHA copolymers can be synthesized with desired repeating unit ratios and sets of physical properties by simply selecting the appropriate starting substrate ratio. These physical properties are compared to those of common, petroleum-based polymers in Table 5.

An unexpected trend was observed in the results of GPC experiments for determining the average molecular weights of the PHOHB copolymers (Table 8). Both the weight average ($M_w$) and number average ($M_n$) decreased with increasing percentages of 3HO repeating units. The enzymes expressed in E. coli LSBJ to synthesize PHAs, PhaJ4 and PhaC1(STQK) (FIG. 1), have broad substrate specificities but prefer MCL sized substrates (21,22,26). The PhaC1(STQK) enzyme has been reported to produce lower molecular weight PHA products than its parent enzyme from P. sp. 61-3 (56), and other mutations have been shown to increase molecular weights produced by this enzyme (57-59). However, based on the preferred substrate size of the enzyme, it was expected that increasing the percentage of 3HO in the copolymers would lead to an increase in the average molecular weight. What was observed instead was a decrease in molecular weights as the 3HO repeating unit fraction of the copolymer increased. Previous work has shown that PHB produced with the PhaC1(STQK) enzyme in E. coli was around 490 kDa ($M_n$) (54). The average molecular weights appear to be moving toward what has been reported for homopolymer PHB from this enzyme as the amount of 3HB in the copolymer increases (Table 8). Similarly, the molecular weights move toward molecular weights observed when a near homopolymer of PHO was produced in E. coli LSBJ (44). Molecular weight of polymers is another determining factor in the physical properties of PHAs, and there are recent and current efforts to consistently increase these values (60). These results indicate that molecular weights of PHA copolymers can also be controlled by the mole ratio of SCL to MCL repeating units incorporated into the polymer.

REFERENCES (1) Lu, J.; Tappel, R. C.; Nomura, C. T. Mini-Review: Biosynthesis of Poly(hydroxyalkanoates). Polym. Rev. 2009, 49, 226-248.
(2) Sudesh, K.; Abe, H.; Doi, Y. Synthesis, structure and properties of polyhydroxyalkanoates: biological polyesters. Prog. Polym. Sci. 2000, 25, 1503-1555.

(3) Abe, H.; Doi, Y. Side-Chain Effect of Second Monomer Units on Crystalline Morphology, Thermal Properties, and Enzymatic Degradability for Random Copolyesters of (R)-3-Hydroxybutyric Acid with (R)-3-Hydroxyalkanoic Acids. Biomacromolecules 2002, 3, 133-138.

(4) Zhu, C.; Nomura, C. T.; Perrotta, J. A.; Stipanovic, A. J.; Nakas, J. P. Production and Characterization of Poly-3-hydroxybutyrate from Biodiesel-Glycerol by *Burkholderia cepacia* ATCC 17759. Biotechnol. Prog. 2010, 26, 424-430.

(5) Steinbüchel, A.; Valentin, H. E.; Schönebaum, A. Application of recombinant gene technology for production of polyhydroxyalkanoic acids: biosynthesis of poly (4-hydroxybutyric acid) homopolyester. J. Polym. Environ. 1994, 2, 67-74.

(6) Wang, H.-H.; Li, X.-T.; Chen, G.-Q. Production and characterization of homopolymer polyhydroxyheptanoate (P3HHp) by a fadBA knockout mutant *Pseudomonas putida* KTOY06 derived from *P. putida* KT2442. Process Biochem. 2009, 44, 106-111.

(7) Liu, Q.; Luo, G.; Zhou, X. R.; Chen, G.-Q. Biosynthesis of poly(3-hydroxydecanoate) and 3-hydroxydodecanoate dominating polyhydroxyalkanoates by β-oxidation pathway inhibited *Pseudomonas putida*. Met. Eng. 2011, 13, 11-17.

(8) Wang, H.-H.; Zhou, X. R.; Liu, Q.; Chen, G.-Q. Biosynthesis of polyhydroxyalkanoate homopolymers by *Pseudomonas putida*. Appl. Microbiol. Biotechnol. 2011, 89, 1497-1507.

(9) Rai, R.; Yunos, D. M.; Boccaccini, A. R.; Knowles, J. C.; Barker, I. A.; Howdle, S. M.; Tredwell, G. D.; Keshavarz, T.; Roy, I. Poly-3-hydroxyoctanoate P(3HO), a medium chain length polyhydroxyalkanoate homopolymer from *Pseudomonas mendocina*. Biomacromolecules 2011, 12, 2126-2136.

(10) Rai, R.; Keshavarz, T.; Roether, J. A.; Boccaccini, A. R.; Roy, I. Medium chain length polyhydroxyalkanoates, promising new biomedical materials for the future. Mater. Sci. Eng., R 2011, 72, 29-47.

(11) Campbell, J. W.; Morgan-Kiss, R. M.; Cronan, J. E., Jr A new *Escherichia coli* metabolic competency: growth on fatty acids by a novel anaerobic β-oxidation pathway. Mol. Microbiol. 2003, 47, 793-805.

(12) Rhie, H. G.; Dennis, D. Role of fadR and atoC (Con) Mutations in poly (3-Hydroxybutyrate-Co-3-Hydroxyvalerate) Synthesis in Recombinant pha+ *Escherichia coli*. Appl. Environ. Microbiol. 1995, 61, 2487-2492.

(13) Ren, Q.; Sierro, N.; Kellerhals, M.; Kessler, B.; Witholt, B. Properties of Engineered Poly-3-Hydroxyalkanoates Produced in Recombinant *Escherichia coli* Strains. Appl. Environ. Microbiol. 2000, 66, 1311-1320.

(14) Fiedler, S.; Steinbüchel, A.; Rehm, B. The role of the fatty acid β-oxidation multienzyme complex from *Pseudomonas oleovorans* in polyhydroxyalkanoate biosynthesis: molecular characterization of the fadBA operon from *P. oleovorans* and of the enoyl-CoA hydratase genes phaJ from *P. oleovorans* and *Pseudomonas putida*. Arch. Microbiol. 2002, 178, 149-160.

(15) Snell, K. D.; Feng, F.; Zhong, L.; Martin, D.; Madison, L. L. yfcx enables medium-chain-length poly(3-hydroxyalkanoate) formation from fatty acids in recombinant *Escherichia coli* fadB strains. J. Bacteriol. 2002, 184, 5696-5705.

(16) Park, S. J.; Park, J. P.; Lee, S. Y.; Doi, Y. Enrichment of specific monomer in medium-chain-length poly(3-hydroxyalkanoates) by amplification of fadD and fadE genes in recombinant *Escherichia coli*. Enzyme Microb. Technol. 2003, 33, 62-70.

(17) DiRusso, C. C.; Heimert, T. L.; Metzger, A. K. Characterization of FadR, a Global Transcriptional Regulator of Fatty Acid Metabolism in *Escherichia coli*. J. Biol. Chem. 1992, 267, 8685-8691.

(18) Spratt, S. K.; Ginsburgh, C. L.; Nunn, W. D. Isolation and Genetic Characterization of *Escherichia coli* Mutants Defective in Propionate Metabolism. J. Bacteriol. 1981, 146, 1166-1169.

(19) Pauli, G.; Overath, P. ato Operon: a Highly Inducible System for Acetoacetate and Butyrate Degradation in *Escherichia coli*. J. Appl. Microbiol. 1972, 29, 553-562.

(20) Jenkins, L. S.; Nunn, W. D. Genetic and Molecular Characterization of the Genes Involved in Short-Chain Fatty Acid Degradation in *Escherichia coli*: The ato System. J. Bacteriol. 1987, 169, 42-52.

(21) Tsuge, T.; Taguchi, K.; Taguchi, S.; Doi, Y. Molecular characterization and properties of (R)-specific enoyl-CoA hydratases from *Pseudomonas aeruginosa*: metabolic tools for synthesis of polyhydroxyalkanoates via fatty acid β-oxidation. Int. J. Biol. Macromol. 2003, 31, 195-205.

(22) Sato, S.; Kanazawa, H.; Tsuge, T. Expression and characterization of (R)-specific enoyl coenzyme A hydratases making a channeling route to polyhydroxyalkanoate biosynthesis in *Pseudomonas putida*. Appl. Microbiol. Biotechnol. 2011, 90, 951-959.

(23) Fukui, T.; Yokomizo, S.; Kobayashi, G.; Doi, Y. Coexpression of polyhydroxyalkanoate synthase and (R)-enoyl-CoA hydratase genes of *Aeromonas caviae* establishes copolyester biosynthesis pathway in *Escherichia coli*. FEMS Microbiol. Lett. 1999, 170, 69-75.

(24) Tsuge, T.; Fukui, T.; Matsusaki, H.; Taguchi, S.; Kobayashi, G.; Ishizaki, A.; Doi, Y. Molecular cloning of two (R)-specific enoyl-CoA hydratase genes from *Pseudomonas aeruginosa* and their use for polyhydroxyalkanoate synthesis. FEMS Microbiol. Lett. 2000, 184, 193-198.

(25) Budde, C. F.; Riedel, S. L.; Willis, L. B.; Rha, C.; Sinskey, A. J. Production of Poly(3-Hydroxybutyrate-co-3-Hydroxyhexanoate) from Plant Oil by Engineered *Ralstonia eutropha* Strains. Appl. Environ. Microbiol. 2011, 77, 2847-2854.

(26) Takase, K.; Taguchi, S.; Doi, Y. Enhanced Synthesis of Poly(3-hydroxybutyrate) in Recombinant *Escherichia coli* by Means of Error-Prone PCR Mutagenesis, Saturation Mutagenesis, and In Vitro Recombination of the Type II Polyhydroxyalkanoate Synthase Gene. J. Biochem. 2003, 133, 139-145.

(27) Matsusaki, H.; Manji, S.; Taguchi, K.; Kato, M.; Fukui, T.; Doi, Y. Cloning and Molecular Analysis of the Poly (3-hydroxybutyrate) and Poly(3-hydroxybutyrate-co-3-hydroxyalkanoate) Biosynthesis Genes in *Pseudomonas* sp. Strain 61-3. J. Bacteriol. 1998, 180, 6459-6467.

(28) Nomura, C. T.; Tanaka, T.; Gan, Z.; Kuwabara, K.; Abe, H.; Takase, K.; Taguchi, K.; Doi, Y. Effective Enhancement of Short-Chain-Length-Medium-Chain-Length Polyhydroxyalkanoate Copolymer Production by Coexpression of Genetically Engineered 3-Ketoacyl-Acyl-Carrier-Protein Synthase III (fabH) and Polyhydroxyalkanoate Synthesis Genes. Biomacromolecules 2004, 5, 1457-1464.

(29) Nomura, C. T.; Tanaka, T.; Eguen, T. E.; Appah, A. S.; Matsumoto, K.; Taguchi, S.; Ortiz, C. L.; Doi, Y. FabG Mediates Polyhydroxyalkanoate Production from Both Related and Nonrelated Carbon Sources in Recombinant *Escherichia coli* LS5218. Biotechnol. Frog. 2008, 24, 342-351.

(30) EPA, U.S.A. Municipal Solid Waste Generation, Recycling, and Disposal in the United States: Facts and Figures for 2010; 2012; pp. 1-12.

(31) Keshavarz, T.; Roy, I. Polyhydroxyalkanoates: bioplastics with a green agenda. Curr. Opin. Microbiol. 2010, 13, 321-326.

(32) Jendrossek, D.; Handrick, R. Microbial degradation of polyhydroxyalkanoates. Annu. Rev. Microbiol. 2002, 56, 403-432.

(33) Lopez-Llorca, L.; Colom Valiente, M.; Gascon, A. A Study of Biodegradation of Poly-β-hydroxyalkanoate (PHA) Films in Soil Using Scanning Electron Microscopy. Micron 1993, 24, 23-29.

(34) Kusaka, S.; Iwata, T.; Doi, Y. Properties and biodegradability of ultra-high-molecular-weight poly [(R)-3-hydroxybutyrate] produced by a recombinant *Escherichia coli*. Int. J. Biol. Macromol. 1999, 25, 87-94.

(35) Imam, S.; Gordon, S.; Shogren, R.; Tosteson, T.; Govind, N.; Greene, R. Degradation of Starch-Poly (β-Hydroxybutyrate-Co-β-Hydroxyvalerate) Bioplastic in Tropical Coastal Waters. Appl. Environ. Microbiol. 1999, 65, 431-437.

(36) Ren, Q.; Ruth, K.; Thöny-Meyer, L.; Zinn, M. Enatiomerically pure hydroxycarboxylic acids: current approaches and future perspectives. Appl. Microbiol. Biotechnol. 2010, 87, 41-52.

(37) Sparks, J.; Scholz, C. Evaluation of a Cationic Poly(β-hydroxyalkanoate) as a Plasmid DNA Delivery System. Biomacromolecules 2009, 10, 1715-1719.

(38) Misra, S. K.; Valappil, S. P.; Roy, I.; Boccaccini, A. R. Polyhydroxyalkanoate (PHA)/Inorganic Phase Composites for Tissue Engineering Applications. Biomacromolecules 2006, 7, 2249-2258.

(39) Wampfler, B.; Ramsauer, T.; Rezzonico, S.; Hischier, R.; Köhling, R.; Thöny-Meyer, L.; Zinn, M. Isolation and Purification of Medium Chain Length Poly(3-hydroxyalkanoates) (mcl-PHA) for Medical Applications Using Nonchlorinated Solvents. Biomacromolecules 2010, 11, 2716-2723.

(40) Noda, I.; Green, P. R.; Satkowski, M. M.; Schechtman, L. A. Preparation and Properties of a Novel Class of Polyhydroxyalkanoate Copolymers. Biomacromolecules 2005, 6, 580-586.

(41) Tsuge, T.; Watanabe, S.; Sato, S.; Hiraishi, T.; Abe, H.; Doi, Y.; Taguchi, S. Variation in Copolymer Composition and Molecular Weight of Polyhydroxyalkanoate Generated by Saturation Mutagenesis of *Aeromonas caviae* PHA Synthase. Macromolecules 2007, 7, 846-854.

(42) Yamada, M.; Matsumoto, K.; Shimizu, K.; Uramoto, S.; Nakai, T.; Shozui, F.; Taguchi, S. Adjustable Mutations in Lactate (LA)-Polymerizing Enzyme for the Microbial Production of LA-Based Polyesters with Tailor-Made Monomer Composition. Biomacromolecules 2010, 11, 815-819.

(43) Meng, D.-C.; Shi, Z.-Y.; Wu, L.-P.; Zhou, Q.; Wu, Q.; Chen, J.-C.; Chen, G.-Q. Production and characterization of poly(3-hydroxypropionate-co-4-hydroxybutyrate) with fully controllable structures by recombinant *Escherichia coli* containing an engineered pathway. Met. Eng. 2012, 14, 317-324.

(44) Example 1

(45) Datsenko, K. A.; Wanner, B. L. One-step inactivation of chromosomal genes in *Escherichia coli* K-12 using PCR products. Proc. Natl. Acad. Sci. U.S.A. 2000, 97, 6640-6645.

(46) Wang, Q.; Nomura, C. T. Monitoring differences in gene expression levels and polyhydroxyalkanoate (PHA) production in *Pseudomonas putida* KT2440 grown on different carbon sources. J. Biosci. Bioeng. 2010, 110, 653-659.

(47) Sambrook, J.; Russell, D. W. Molecular Cloning; 3rd ed. CSHL Press: Cold Spring Harbor, 2001.

(48) Jiang, X.; Ramsay, J. A.; Ramsay, B. A. Acetone extraction of mcl-PHA from *Pseudomonas putida* KT2440. J. Microbiol. Methods 2006, 67, 212-219.

(49) Arai, Y.; Nakashita, H.; Suzuki, Y.; Kobayashi, Y.; Shimizu, T.; Yasuda, M.; Doi, Y.; Yamaguchi, I. Synthesis of a Novel Class of Polyhydroxyalkanoates in *Arabidopsis* Peroxisomes, and Their Use in Monitoring Short-Chain-Length Intermediates of β-Oxidation. Plant Cell Physiol. 2002, 43, 555-562.

(50) Rodriguez, E. D.; Luo, X.; Mather, P. T. Linear/Network Poly(ε-caprolactone) Blends Exhibiting Shape Memory Assisted Self-Healing (SMASH). ACS Appl. Mater. Interfaces 2011, 3, 152-161.

(51) Matsusaki, H.; Abe, H.; Taguchi, K.; Fukui, T.; Doi, Y. Biosynthesis of poly(3-hydroxybutyrate-co-3-hydroxyalkanoates) by recombinant bacteria expressing the PHA synthase gene phaC1 from *Pseudomonas* sp. 61-3. Appl. Microbiol. Biotechnol. 2000, 53, 401-409.

(52) Sparks, J.; Scholz, C. Synthesis and Characterization of a Cationic Poly(β-hydroxyalkanoate). Biomacromolecules 2008, 9, 2091-2096.

(53) Rai, R.; Yunos, D. M.; Boccaccini, A. R.; Knowles, J. C.; Barker, I. A.; Howdle, S. M.; Tredwell, G. D.; Keshavarz, T.; Roy, I. Poly-3-hydroxyoctanoate P(3HO), a Medium Chain Length Polyhydroxyalkanoate Homopolymer from *Pseudomonas mendocina*. Biomacromolecules 2011, 12, 2126-2136.

(54) Matsumoto, K.; Takase, K.; Aoki, E.; Doi, Y.; Taguchi, S. Synergistic Effects of Glu130Asp Substitution in the Type II Polyhydroxyalkanoate (PHA) Synthase: Enhancement of PHA Production and Alteration of Polymer Molecular Weight. Biomacromolecules 2005, 6, 99-104.

(55) Matsusaki, H.; Abe, H.; Doi, Y. Biosynthesis and Properties of Poly(3-hydroxybutyrate-co-3-hydroxyalkanoates) by Recombinant Strains of *Pseudomonas* sp. 61-3. Biomacromolecules 2000, 1, 17-22.

(56) Takase, K.; Matsumoto, K.; Taguchi, S.; Doi, Y. Alteration of Substrate Chain-Length Specificity of Type II Synthase for Polyhydroxyalkanoate Biosynthesis by in Vitro Evolution: in Vivo and in Vitro Enzyme Assays. Biomacromolecules 2004, 5, 480-485.

(57) Tsuge, T.; Yano, K.; Imazu, S.-I.; Numata, K.; Kikkawa, Y.; Abe, H.; Taguchi, S.; Doi, Y. Biosynthesis of Polyhydroxyalkanoate (PHA) Copolymer from Fructose Using Wild-Type and Laboratory-Evolved PHA Synthases. Macromolecules 2005, 5, 112-117.

(58) Matsumoto, K.; Aoki, E.; Takase, K.; Doi, Y.; Taguchi, S. In Vivo and in Vitro Characterization of Ser477X Mutations in Polyhydroxyalkanoate (PHA) Synthase 1 from *Pseudomonas* sp. 61-3: Effects of Beneficial Mutations on Enzymatic Activity, Substrate Specificity, and Molecular Weight of PHA. Biomacromolecules 2006, 7, 2436-2442.

(59) Shozui, F.; Matsumoto, K.; Sasaki, T.; Taguchi, S. Engineering of polyhydroxyalkanoate synthase by Ser477X/Gln481X saturation mutagenesis for efficient production of 3-hydroxybutyrate-based copolyesters. Appl. Microbiol. Biotechnol. 2009, 84, 1117-1124.

(60) Hiroe, A.; Tsuge, K.; Nomura, C. T.; Itaya, M.; Tsuge, T. Rearrangement of gene order in the phaCAB operon leads to effective production of ultra-high-molecular-weight poly[(R)-3-hydroxybutyrate] in genetically engineered *Escherichia coli*. Appl. Environ. Microbiol. 2012, 78, 3177-3184.

6.3 Example 3

Engineering *E. coli* for Improved Production of polyhydroxyalkanoate (PHA)-Based Biodegradable Plastics Introduction This example sets forth systems and methods for increasing the production of SCL-MCL and other novel PHAs. This example describes the improvement of PHA biopolymer production using metabolic engineering techniques to diversify the supply of monomers for PHA production and increase overall production of the polymers.

Materials and Methods

Gene Rearrangement to Control the Molecular Weight of PHA-Based Polymers

Figure 29:
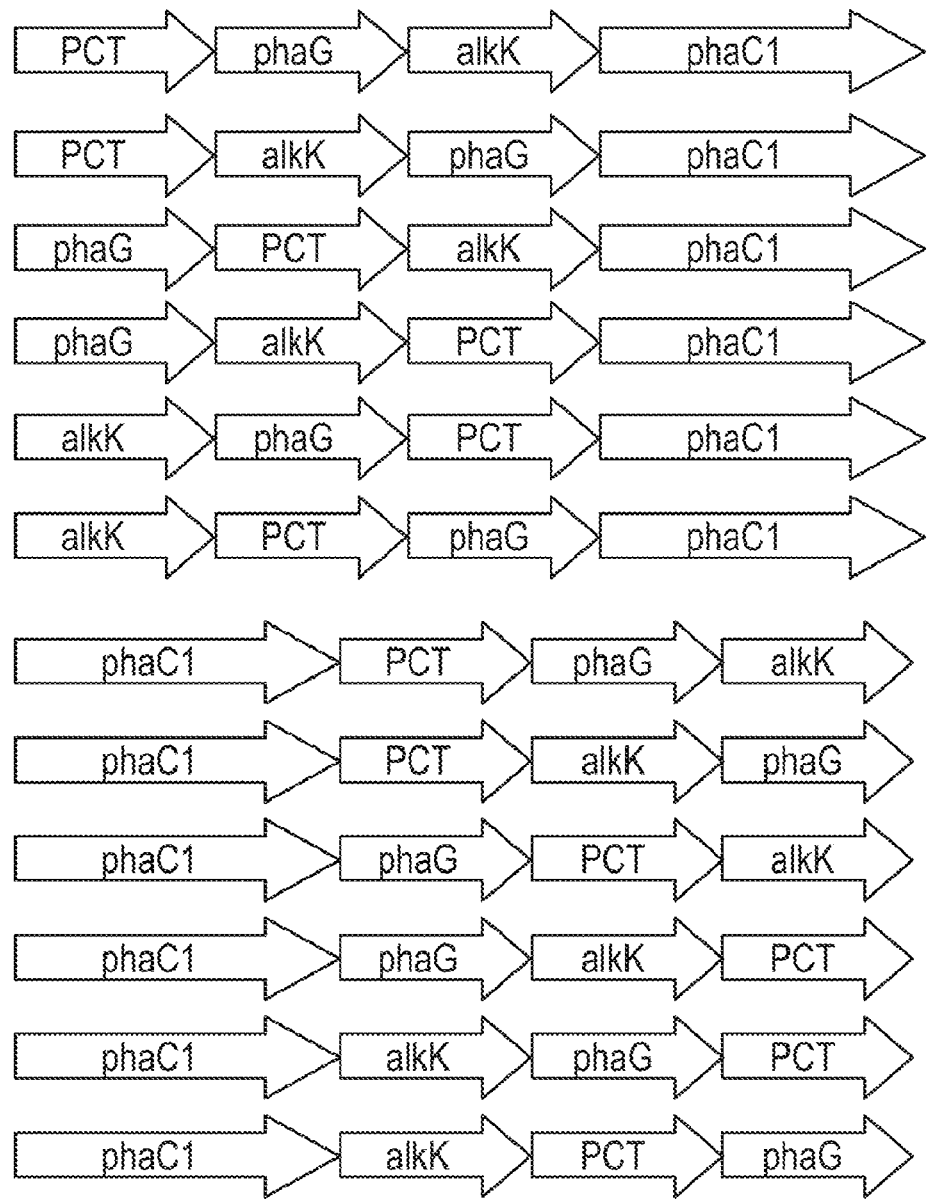

Control over the molecular weights of polymers can have dramatic effects on the physical properties of the materials. Previous studies have demonstrated that gene order and thus enzyme expression levels are partially responsible for controlling the molecular weights of PHA polymers produced in *E. coli*. PHB polymers have been produced with ultra-high-molecular-weights using gene rearrangement (38). It is also known that PHA synthase activity is a key factor for controlling the molecular weight of PHA (104). This method for controlling the molecular weights of PHA-co-polylactic acid (PLA) copolymers is shown in FIG. 29. In addition to producing polymers with higher molecular weights, it is also important to produce PHA polymers with lower molecular weights. Many of the polylactic acid (PLA) biomaterials used in tissue engineering applications are of much lower molecular weights (typically $10^3$-$10^4$ Da) (41, 101) than those the PHA polymers typically produced (typically $10^5$-$10^6$ Da). High levels of expression of the phaC gene encoding the PHA synthase relative to monomer supplying enzymes result in the production of polymers with lower molecular weights.

To establish a range of molecular weights of PHA polymers produced in the engineered *E. coli* strains, expression constructs are assembled with the PHA synthase and various monomer supplying genes relative to a series of promoters with variable strengths (lac, ara, trc, *R. eutropha* native pha promoter) in large expression constructs using Gibson assembly (30, 31), a method well known in the art. Briefly, Gibson assembly allows for the one-step isothermal in vitro assembly of multiple DNA fragments regardless of fragment length or end compatibility. Placement of the phaC gene encoding the PHA synthase at the position nearest to the promoter results in PHA polymers with lower molecular weights while PHA polymers produced in constructs where the phaC gene was furthest from the promoter had the highest molecular weight (38).

Thus initial Gibson assembled constructs are made with the phaC1(STQK) gene occupying either the first or last position of the construct with genes encoding monomer-supplying enzymes shuffled into all other positions (FIG. 29). As an alternative, these constructs can be assembled via the OGAB method employed for SCL PHA production (38). These constructs are further engineered for varying levels of protein production by altering the ribosomal binding site using the RBS calculator designed and maintained by Howard Salis (salis.psu.edu/software) (96, 97). The RBS calculator can be used to calculate the relative expression of each of the proteins based on designed RBS sites to alter translation from 0.5-fold to 100,000-fold higher than the original rate of translation within a factor of 2.3 (97).

The RBS calculator is then used to design primers with engineered RBSs for the pct, phaG, alkK, and phaC 1 (STQK) by three increments (0.5, 10, and 100-fold of the native RBS). This results in controlled expression of the genes in the pathway, which leads to differences in the molecular weights of any polymers produced based on our previous study with the SCL PHA polymer PHB (38).

Production of PHA Polymers in Large Quantities with Defined Repeating Unit Compositions from Fatty Acids in *E. coli*

Engineering *E. coli* to Produce PHA Polymers from Fatty Acids

Figure 26:
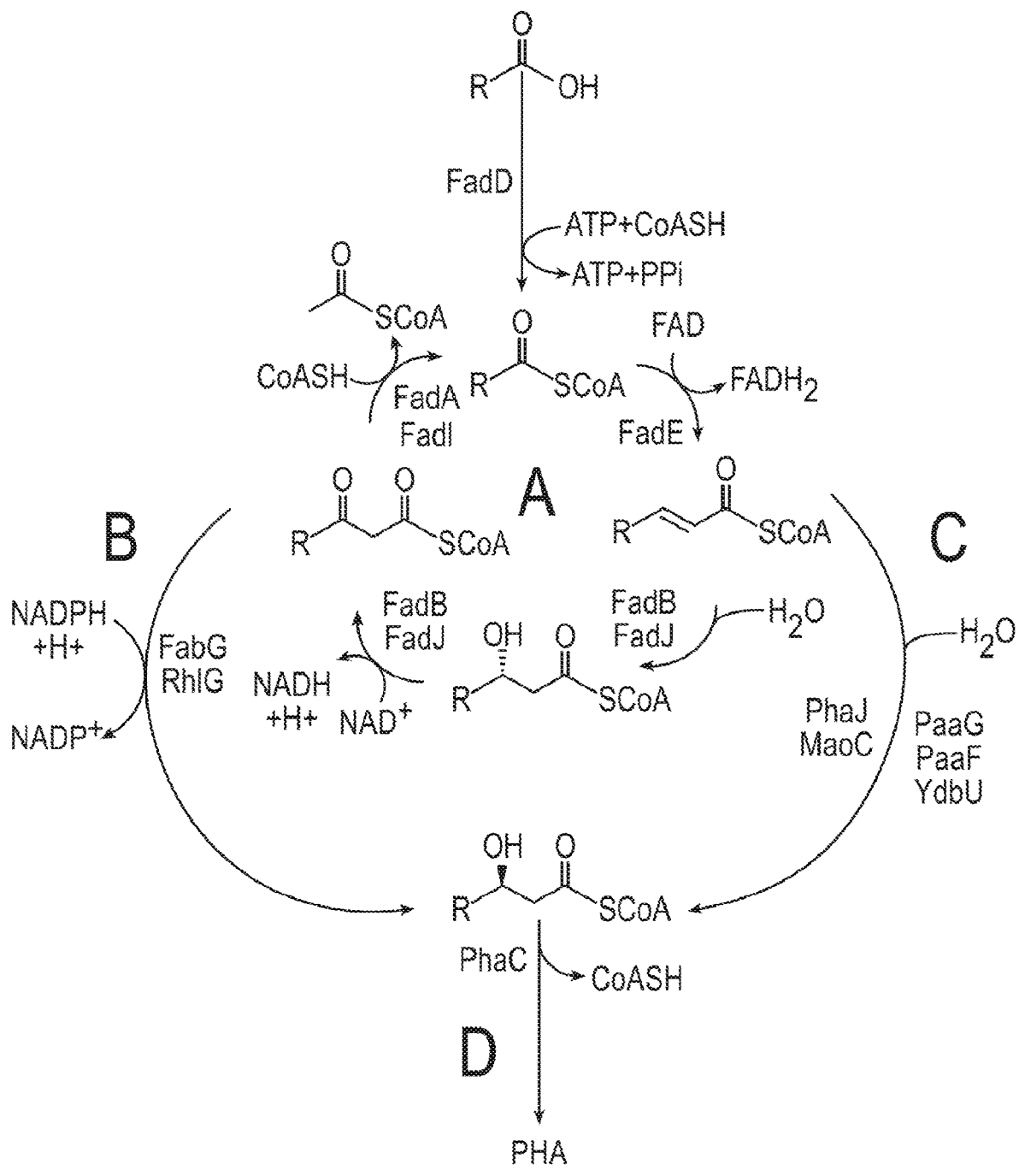

Pathways for the production of PHA polymers from fatty acids are shown in FIG. 26. It has been shown in Examples 1 and 2 that *E. coli* can be engineered to produce PHA from fatty acids. There are two main routes to convert β-oxidation intermediates to substrates for PHA production: (i) conversion of enoyl-CoA to (R)-3-hydroxyacyl-CoA substrates via (R)-specific-enoyl-CoA hydratases such as PhaJ (27, 99, 119-122), MaoC, PaaG, PaaF, and YdbU (86). The other route is via conversion of 3-ketoacyl-CoA to the (R)-3-hydroxyacyl-CoA substrates for polymerization using 3-ketoacyl reductases such as FabG (82, 94, 111) or Rh1G (13). The major shortcoming of these studies is that β-oxidation of fatty acids leads to an uncontrolled repeating unit composition within the PHA polymers produced. Thus, there is little control over the physical properties of the PHA polymers produced. Also, to date, there has been only one study looking at the production of PLA-co-MCL PHA polymers (68), but it is expected that this class of polymers will possess desirable material properties in a similar way that SCL-MCL PHA copolymers do. These shortcomings have led to the impetus for the studies described in this example to produce engineered *E. coli* strains capable of producing a series of PHA and PHA-co-PLA copolymers with specifically defined repeating unit compositions in order to produce biopolymers with relevant material properties, such as improved ductility and toughness and clarity.

PHA-co-PLA copolymers are produced with defined repeating unit compositions by co-expressing the propionyl-CoA transferase (PCT) enzyme in the engineered *E. coli* LSBJ strain (115, 117). This strain is further engineered to improve yields of PHA by deletion of genes encoding negative transcriptional regulators (arcA and ompR) of the β-oxidation pathway in *E. coli* to increase substrate availability for PHA production. This leads to higher levels of production of both PHA polymers and copolymers and the production of PHA-co-PLA copolymers with defined repeating unit compositions.

Experimental Design

Deregulating Repression of β-Oxidation in *E. coli*

Figure 27:
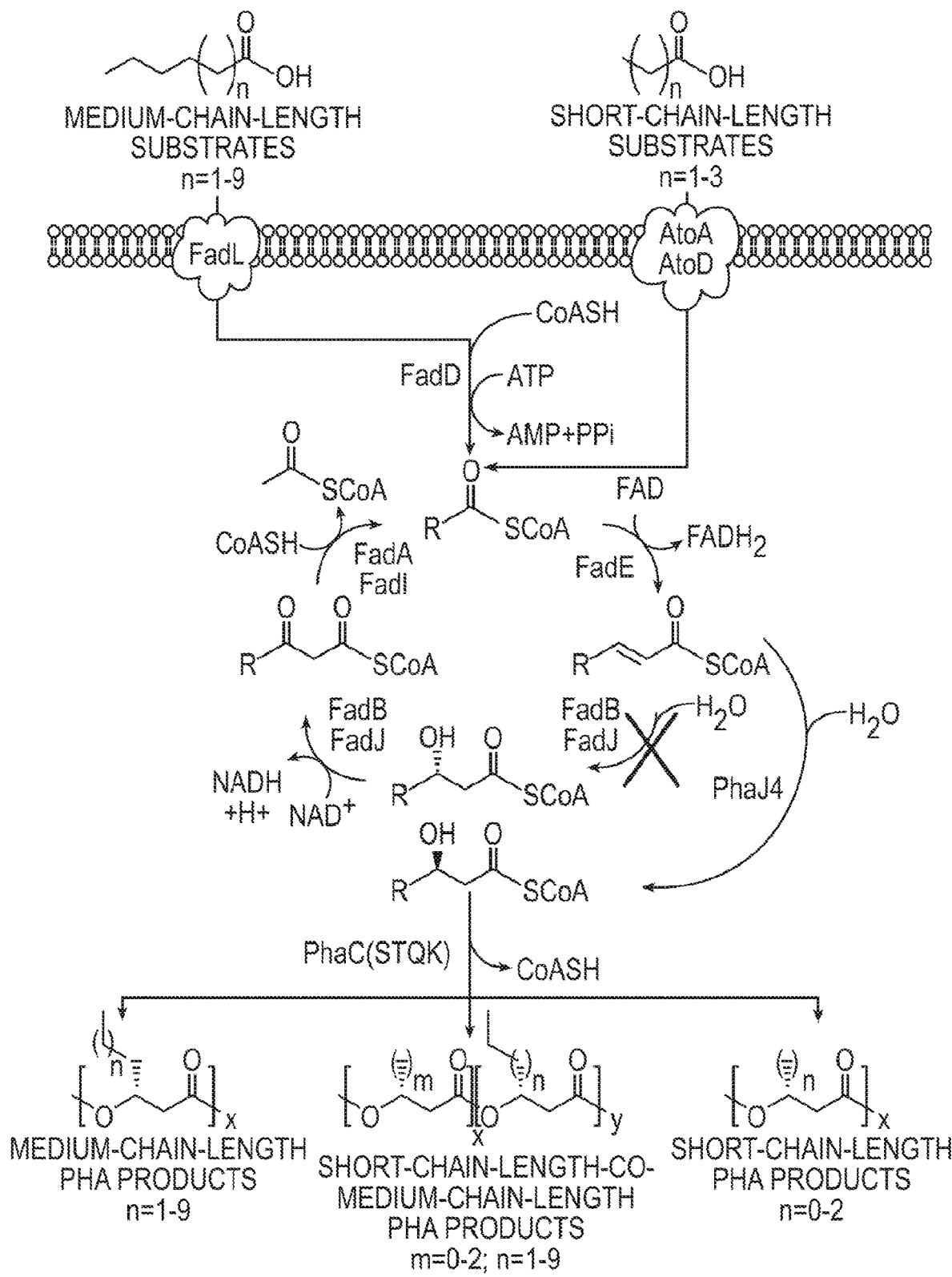
Figure 30:
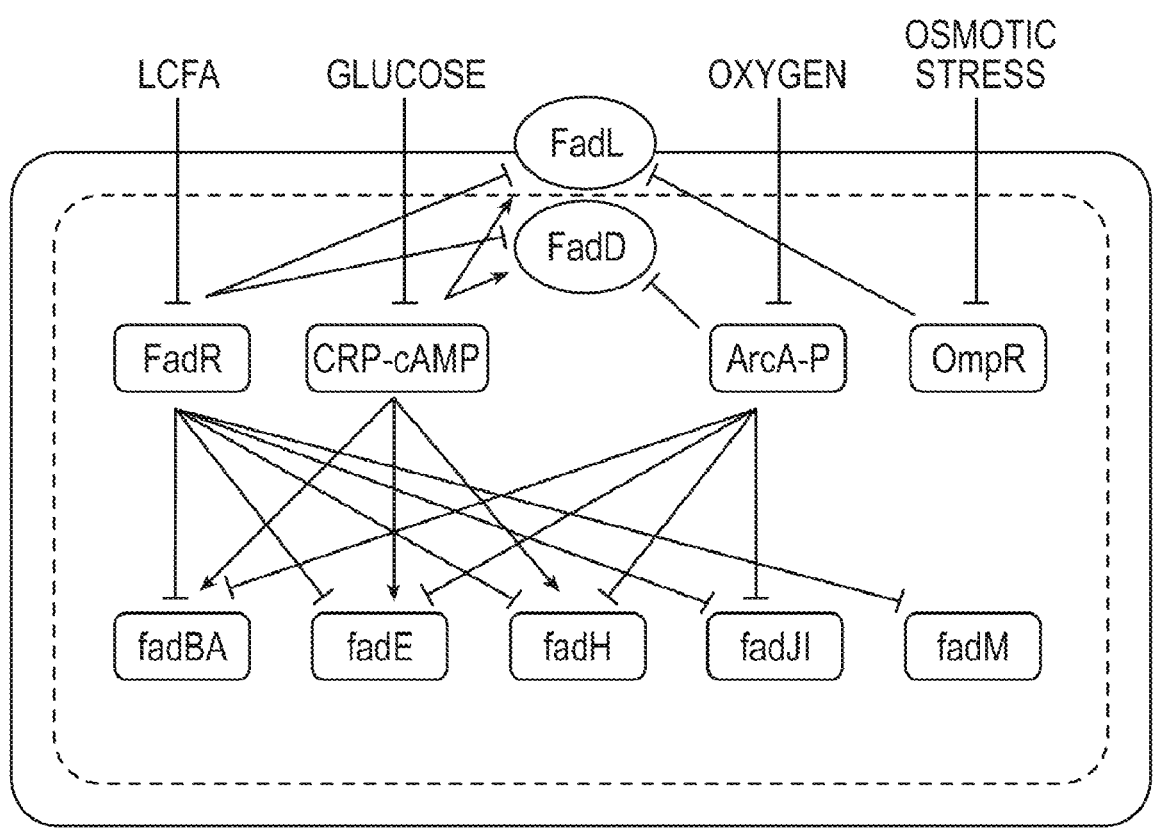

*E. coli* LSBJ is used as the parental strain for the production of PHA polymers with defined repeating unit composition from fatty acids (FIG. 27). This strain utilizes the β-oxidation pathway to generate intermediates for PHA synthesis. To increase flux through this pathway, it is necessary to engineer or delete negative transcriptional regulators of β-oxidation and fatty acid uptake in *E. coli*. These have been identified in a previous study (25), and an outline of the modifications made in this example is shown in FIG. 30. Modifications include the deletion of genes encoding transcriptional regulators (fadR, arcA, and ompR) that downregulate expression of the fad regulon. *E. coli* LSBJ strain has been previously engineered that carries an inactivated fadR gene, constitutively expressed atoC, and inactivated fadB and fadJ genes for the production of PHA polymers with defined repeating unit compositions (115, 117, Examples 1 and 2). For this example, this strain is further engineered for optimized utilization of fatty acids as feedstocks for PHA polymer production by additionally inactivating the arcA and ompR genes using the λ-red system (117).

For example, LSBJ-arcA, LSBJ-ompR, and LSBJ-arcA-ompR *E. coli* strains are developed. PHA polymers are then produced in each strain as done for *E. coli* LSBJ, and polymer and growth yields calculated as previously described (115, 117).

ArcA has a regulatory role for the fad genes of *E. coli* (15). *E. coli* arcA mutants (71, 72) can be used for MCL PHA production.

OmpR has been shown previously to repress expression of fadL, which encodes the protein responsible for uptake of long-chain fatty acids in *E. coli* (37). To remove this repression, ompR is inactivated both independently and successively with arcA in *E. coli* LSBJ via λ-red recombination (18). Inactivation of these repressors leads to higher levels of both fatty acid substrate uptake and PHA production via the engineered β-oxidation pathway in *E. coli* LSBJ. Greater flux and uptake of the feedstocks of this pathway increase overall yields and decrease incubation times to produce PHA polymers from fatty acids.

Production of MCL PHA-co-PLA Polymers with Defined Repeating Unit Compositions

Figure 28:
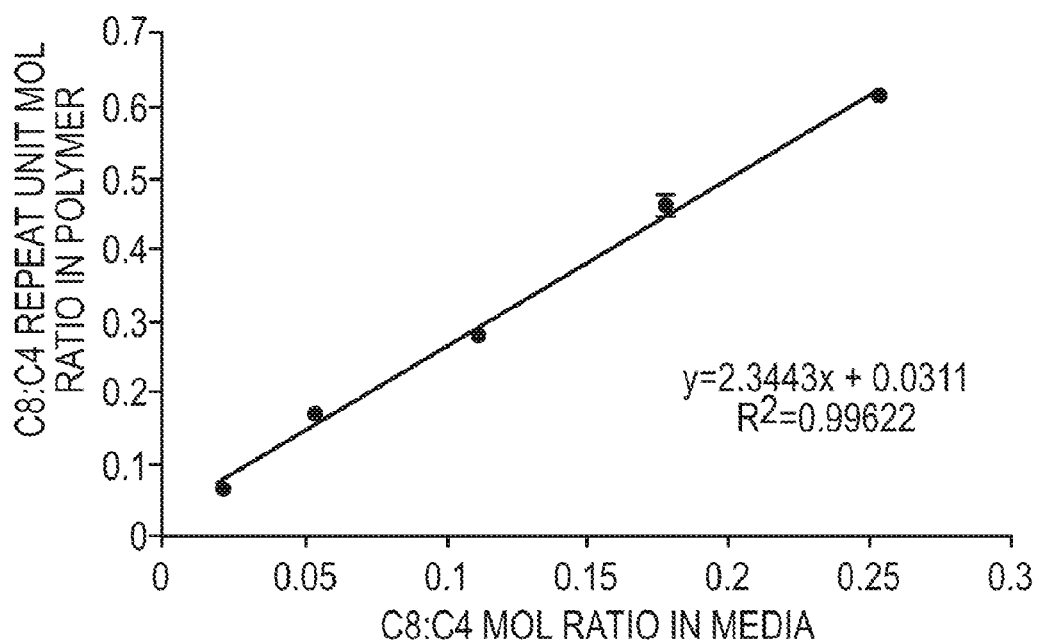
Figure 31:
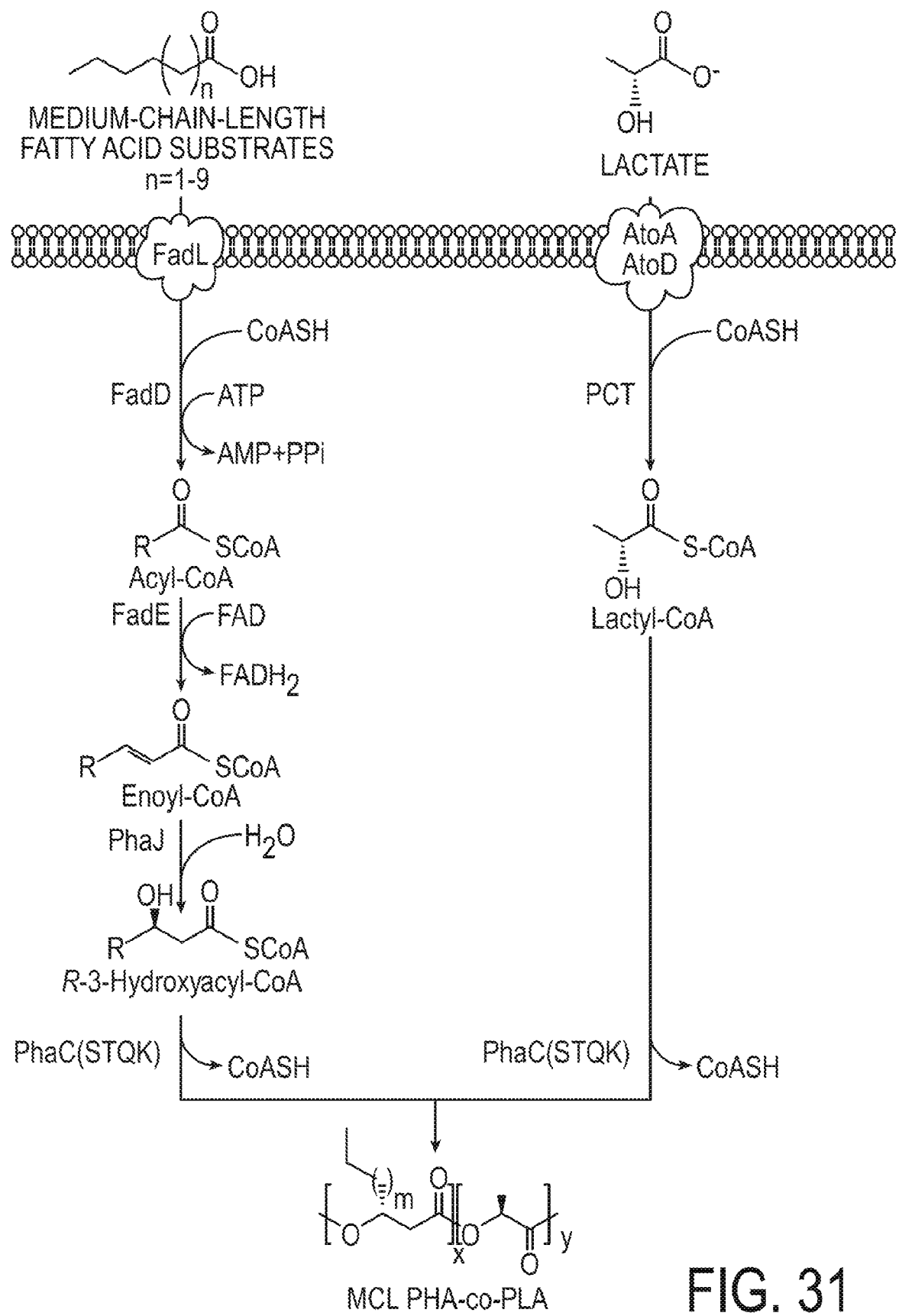

PHA homopolymers (117) and PHA copolymers (115) have been previously produced (see Examples 1 and 2) with defined repeating unit composition by supplying specific ratios of fatty acid feedstocks to the *E. coli* LSBJ strain (FIGS. 27 and 28). This control is extended to PHA-co-PLA copolymers by the co-expression of the pct gene with phaJ4 and phaC1(STQK) in *E. coli* LSBJ and co-feeds of specific concentrations of lactic acid and fatty acids (FIG. 31). The pct gene will be PCR amplified from the pTV118N plasmid (112), subcloned into the pBBR-C1J4SII vector (117) harboring the phaJ4 and phaC1(STQK) genes, and transformed into *E. coli* LSBJ. The transformed strain is grown in the presence of octanoate and lactic acid at various feed ratios (100:0, 90:10, 60:40, 50:50, 40:60, 10:90, and 0:100, octanoate:lactate) to produce MCL PHA-co-PLA copolymers with defined repeating unit compositions.

REFERENCES

1. Abe, H., and Y. Doi. 2002. Side-chain effect of second monomer units on crystalline morphology, thermal properties, and enzymatic degradability for random copolyesters of (R)-3-hydroxybutyric acid with (R)-3-hydroxyalkanoic acids. Biomacromolecules 3:133-138.
2. Agus, J., P. Kahar, H. Abe, Y. Doi, and T. Tsuge. 2006. Altered expression of polyhydroxyalkanoate synthase gene and its effect on poly[(R)-3-hydroxybutyrate] synthesis in recombinant *Escherichia coli*. Polym Degrad Stab 91:1645-1650.
3. Agus, J., P. Kahar, H. Abe, Y. Doi, and T. Tsuge. 2006. Molecular weight characterization of poly[(R)-3-hydroxybutyrate] synthesized by genetically engineered strains of *Escherichia coli*. Polym Degrad Stab 91:1138-1146.
4. Ahn, W. S., S. J. Park, and S. Y. Lee. 2000. Production of poly(3-hydroxybutyrate) by fed-batch culture of recombinant *Escherichia coli* with a highly concentrated whey solution. Appl Environ Microbiol 66:3624-7.
5. Akiyama, M., T. Tsuge, and Y. Doi. 2003. Environmental life cycle comparison of polyhydroxyalkanoates produced from renewable carbon resources by bacterial fermentation. Polym Degrad Stab 80:183-194.
6. Anderson, A. J., and E. A. Dawes. 1990. Occurrence, metabolism, metabolic role, and industrial uses of bacterial polyhydroxyalkanoates. Microbiol Rev 54:450-72.
7. Anderson, A. J., G. W. Haywood, and E. A. Dawes. 1990. Biosynthesis and composition of bacterial poly(hydroxyalkanoates). Int J Biol Macromol 12:102-5.
8. Aoyagi, Y., Y. Doi, and T. Iwata. 2003. Mechanical properties and highly ordered structure of ultra-high-molecular-weight poly[(R)-3-hydroxybutyrate] films: Effects of annealing and two-step drawing. Polym. Degrad. Stab. 79:209-216.
9. Ashby, R. D., D. K. Y. Solaiman, G. D. Strahan, C. Zhu, R. C. Tappel, and C. T. Nomura 2012. Glycerine and levulinic acid: Renewable co-substrates for the fermentative synthesis of short-chain poly(hydroxyalkanoate) biopolymers. Biores Technol 118:272-280.
10. Auras, R., B. Harte, and S. Selke. 2004. An overview of polylactides as packaging materials. Macomol Biosci 4:835-864.
11. Blattner, F. R., G. Plunkett III, C. A. Bloch, N. T. Perna, V. Burland, M. Riley, J. Collado-Vides, J. D. Glasner, C. K. Rode, G. F. Mayehw, J. Gregor, N. W. Davis, H. A. Kirkpatrick, M. A. Goeden, D. J. Rose, B. Mau, and Y. Shao. 1997. The complete genome sequence of *Escherichia coli* K-12. Science 277:1453-1462.
12. Bunch, P. K., F. Mat-Jan, N. Lee, and D. P. Clark. 1997. The ldhA gene encoding the fermentative lactate dehydrogenase of *Escherichia coli*. Microbiology 143:187-195.
13. Campos-Garcia, J., A. D. Caro, R. Najera, R. M. Miller-Maier, R. A. Al-Tahhan, and G. Soberon-Chavez. 1998. The *Pseudomonas aeruginosa* rhlG gene encodes an NADPH-dependent beta-ketoacyl reductase which is specifically involved in rhamnolipid synthesis. J Bacteriol 180:4442-51.
14. Cheng, X., L. Kovac, and J. C. Lee. 1995. Probing the mechanism of CRP activation by site-directed mutagenesis: The role of serine 128 in the allosteric pathway of cAMP receptor protein activation. Biochemistry 34:10816-10826.
15. Cho, B.-K., E. M. Knight, and B. O. Palsson. 2006. Transcriptional regulation of the fad regulon genes of *Escherichia coli* by ArcA. Microbiology 152:2207-2219.
16. Choi, J., and S. Y. Lee. 2004. High level production of supra molecular weight poly((R)-3-hydroxybutyrate) by metabolically engineered *Escherichia coli*. Biotechnol Bioprocess Eng 9:196-200.
17. Cirino, P. C., J. W. Chin, and L. O. Ingram. 2006. Engineering *Escherichia coli* for xylitol production from glucose-xylose mixtures. Biotechnol Bioeng 95:1167-1176.
18. Datsenko, K. A., and B. L. Wanner. 2000. One-step inactivation of chromosomal genes in *Escherichia coli* K-12 using PCR products. Proc Natl Acad Sci USA 97:6640-5.

19. Davis, M. S., and J. E. Cronan, Jr. 2001. Inhibition of *Escherichia coli* acetyl coenzyme A carboxylase by acyl-acyl carrier protein. J Bacteriol 183:1499-503.
20. Davis, M. S., J. Solbiati, and J. E. Cronan Jr. 2000. Overproduction of acetyl-CoA carboxylase activity increases the rate of fatty acid biosynthesis in *Escherichia coli*. J Biol Chem 275:28593-28598.
21. Dellomonaco, C., J. M. Clomburg, E. N. Miller, and R. Gonzalez. 2011. Engineered reversal of the of β-oxidation cycle for the synthesis of fuels and chemicals. Nature 476:355-359.
22. Dellomonaco, C., C. Rivera, P. Campbell, and R. Gonzalez. 2010. Engineered respiro-fermentative metabolism for the production of biofuels and biochemicals from fatty acid-rich feedstocks. Appl Environ Microbiol 76:5067-5078.
23. Dodds, D. R., and R. A. Gross. 2007. Chemistry. Chemicals from biomass. Science 318:1250-1251.
24. Drumright, R. E., P. R. Gruber, and D. E. Henton. 2000. Polylactic acid technology. Adv Mater 12:1841-1846.
25. Feng, Y., and J. E. Cronan. 2010. Overlapping repressor binding sites result in additive regulation of *Escherichia coli* FadH by FadR and ArcA. J Bacteriol 192:4289-4299.
26. Fiedler, S., A. Steinbuchel, and B. H. Rehm. 2000. PhaG-mediated synthesis of poly(3-hydroxyalkanoates) consisting of medium-chain-length constituents from nonrelated carbon sources in recombinant *Pseudomonas fragi*. Appl Environ Microbiol 66:2117-24.
27. Fukui, T., S. Yokomizo, G. Kobayashi, and Y. Doi. 1999. Co-expression of polyhydroxyalkanoate synthase and (R)-enoyl-CoA hydratase genes of *Aeromonas caviae* establishes copolyester biosynthesis pathway in *Escherichia coli*. FEMS Microbiol Lett 170:69-75.
28. Gao, X., J. C. Chen, Q. Wu, and G. Q. Chen. 2011. Polyhydroxyalkanoates as a source of chemicals, polymers, and biofuels. Curr Opin Biotechnol 22:768-774.
29. Garges, S., and C. Adhya. 1985. Sites of allosteric shift in the structure of the cyclic AMP receptor protein. Cell 41:745-751.
30. Gibson, D. G., H. O. Smith, C. A. Hutchinson III, J. C. Venter, and C. Merryman. 2010. Chemical synthesis of the mouse mitochondrial genome. Nat Methods 7:901-903.
31. Gibson, D. G., L. Y. Young, R. Y. Chuang, J. C. Venter, C. A. Hutchinson III, and H. O. Smith. 2009. Enzymatic assembly of DNA molecules up to several hundred kilobases. Nat Methods 6:343-345.
32. Görke, B., and J. Stülke. 2008. Carbon catabolite repression in bacteria: many ways to make the most out of nutrients. Nat Rev Microbiol 6:613-624.
33. Groff, D., P. I. Benke, T. S. Batth, G. Bokinsky, C. J. Petzold, P. D. Adams, and J. D. Keasling. 2012. Supplementation of intracellular XylR leads to coutilization of hemicellulose sugars. Appl Environ Microbiol 78:2221-2229.
34. Harding, K. G., J. S. Dennis, H. von Blottnitz, and S. T. L. Harrison. 2007. Environmental analysis of plastic production processes: Comparing petroleum-based polypropylene and polyethylene with biologically-based poly-beta-hydroxybutyric acid using life cycle analysis. J Biotechnol 130:57-66.
35. Haynes, D., N. K. Abayasinghe, G. M. Harrison, K. J. Burg, and D. W. Smith. 2007. In sit copolyesters containing poly(L-lactide) and poly(hydroxyalkanoate) units. Biomacromolecule 8:1131-1137.
36. Heath, R. J., and C. O. Rock. 1995. Regulation of malonyl-CoA metabolism by acyl-acyl carrier protein and β-ketoacyl-acyl carrier protein synthases in *Escherichia coli*. J Biol Chem 270:15531-8.
37. Higashitani, A., Y. Nishimura, H. Hara, H. Aiba, T. Mizuno, and K. Horiuchi. 1993. Osmoregulation of the fatty acid receptor gene fadL in *Escherichia coli*. Mol Gen Genet 240:339-347.
38. Hiroe, A., T. Tsuge, C. T. Nomura, M. Itaya, and T. Tsuge. 2012. Rearrangement of phaABC gene order leads to effective production of ultra-high-molecular-weight poly[(R)-3-hydroxybutyrate] in genetically engineered *Escherichia coli*. Appl Environ Microbiol 78:3177-3184.
39. Hoffmann, N., A. Steinbuchel, and B. H. Rehm. 2000. Homologous functional expression of cryptic phaG from *Pseudomonas oleovorans* establishes the transacylase-mediated polyhydroxyalkanoate biosynthetic pathway. Appl Microbiol Biotechnol 54:665-70.
40. Hoffmann, N., A. Steinbuchel, and B. H. Rehm. 2000. The *Pseudomonas aeruginosa* phaG gene product is involved in the synthesis of polyhydroxyalkanoic acid consisting of medium-chain-length constituents from non-related carbon sources. FEMS Microbiol Lett 184:253-9.
41. Hong, Z., X. Qiu, J. Sun, M. Deng, X. Chen, and X. Jing. 2004. Grafting polymerization of L-lactide on the surface of hydroxyapatite nano-crystals. Polymer 45:6699-6706.
42. Imam, S. H., L. Chen, S. H. Gordon, R. L. Sogren, D. Weisleder, and R. V. Greene. 1998. Biodegradation of injection molded starch-poly(3-hydrocybutyrate-co-3-hydroxyvalerate) blends in a natural compost environment. J Polym Environ 6:91-98.
43. Imam, S. H., S. H. Gordon, R. L. Shogren, T. R. Tosteson, N. S. Govind, and R. V. Greene. 1999. Degradation of starch-poly(β-hydroxybutyrate-co-β-hydroxyvalerate) bioplastic in tropical coastal waters. Appl Environ Microbiol 65:431-437.
44. Ishida, K., R. Hortensius, X. Luo, and P. T. Mather. 2012. Soft bacterial polyester-based shape memory nanocomposites featuring reconfigurable nanostructure. J Polym Sci Part B: Polym Phys 50:387-393.
45. Ishizuka, H., A. Hanamura, T. Inada, and H. Aiba. 1994. Mechanism of the down-regulation of cAMP receptor protein by glucose in *Escherichia coli*: role of autoregulation of the crp gene. EMBO J 13:3077-3082.
46. Iwata, T. 2005. Strong fibers and films of microbial polyesters. Macromol Biosci 5:689-701.
47. Jendrossek, D., and R. Handrick. 2002. Microbial degradation of polyhydroxyalkanoates. Annu Rev Microbiol 56:403-32.
48. Jenkins, L. S., and W. D. Nunn. 1987. Genetic and molecular characterization of the genes involved in short-chain fatty acid degradation in *Escherichia coli*: The ato system. J Bacteriol 169:42-52.
49. Jiang, G. R., S. Nikolova, and D. P. Clark. 2001. Regulation of the ldhA gene, encoding the fermentative lactate dehydrogenase of *Escherichia coli*. Microbiology 147:2437-2446.
50. Jung, Y. K., and S. Y. Lee. 2011. Efficient production of polylactic acid and its copolymers by metabolically engineered *Escherichia coli*. J Biotechnol 151:94-101.
51. Kahar, P., J. Agus, Y. Kikkawa, K. Taguchi, Y. Doi, and T. Tsuge. 2005. Effective production and kinetic characterization of ultra-high-molecular-weight poly[(R)-3 hydroxybutyrate] in recombinant *Escherichia coli*. Polym Degrad Stab 87:161-169.

52. Karimova, G., D. Ladant, and A. Ullmann. 2004. Relief of catabolite repression in a cAMP-independent catabolite gene activator mutant of *Escherichia coli*. Res Microbiol 155:76-79.
53. Khankal, R., J. W. Chin, D. Ghosh, and P. C. Cirino. 2009. Transcriptional effects of CRP* expression in *Escherichia coli*. J Biol Eng 3:13.
54. Kim, S., and B. E. Dale. 2008. Energy and greenhouse gas profiles of polyhydroxybutyrates derived from corn grain: a life cycle perspective. Environ Sci Technol 42:7690-7695.
55. Klinke, S., Q. Ren, B. Witholt, and B. Kessler. 1999. Production of medium-chain-length poly(3-hydroxyalkanoates) from gluconate by recombinant *Escherichia coli*. Appl Environ Microbiol 65:540-8.
56. Kovach, M. E., P. H. Elzer, D. S. Hill, G. T. Robertson, M. A. Farris, R. M. Roop, and K. M. Peterson. 1995. Four new derivatives of the broad-host range cloning vector pBBR1MCS, carrying different antibiotic-resistance cassettes. Gene 166:175.
57. Kusaka, S., H. Abe, S. Y. Lee, and Y. Doi. 1997. Molecular mass of poly[(R)-3-hydroxybutyric acid] produced in a recombinant *Escherichia coli*. Appl Microbiol Biotechnol 47:140-3.
58. Kusaka, S., T. Iwata, and Y. Doi. 1999. Properties and biodegradability of ultra-high-molecular-weight poly [(R)-hydroxybutyrate] produced by a recombinant *Escherichia coli*. Int J Biol Macromol 25:87-94.
59. Lee, S. Y., and H. N. Chang. 1995. Production of poly(3-hydroxybutyric acid) by recombinant *Escherichia coli* strains: genetic and fermentation studies. Can J Microbiol 41 Suppl 1:207-15.
60. Lennen, R. M., D. J. Braden, R. M. West, J. A. Dumesic, and B. F. Pfleger. 2010. A process for microbial hydrocarbon synthesis: Overproduction of fatty acids in *Escherichia coli* and catalytic conversion to alkanes. Biotechnol Bioeng 106:193-202.
61. Lennen, R. M., M. A. Kruziki, K. Kumar, R. A. Zinkel, K. E. Burnum, M. S. Lipton, S. W. Hoover, D. R. Ranatunga, T. M. Wittkopp, W. D. Marner II, and B. F. Pfleger. 2011. Membrane stresses induced by overproduction of free fatty acids in *Escherichia coli*. Appl Environ Microbiol 77:8114-8128.
62. Leonard, E., K. H. Lim, P. N. Saw, and M. A. G. Koffas. 2007. Engineering central metabolic pathways for high-level flavonoid production in *Escherichia coli*. Appl Environ Microbiol 73:3877-3886.
63. Liu, Q., G. Luo, X. R. Zhou, and G. Q. Chen. 2010. Biosynthesis of poly(3-hydroxydecanoate) and 3-hydroxydodecanoate dominating polyhydroxyalkanoates by beta-oxidation pathway inhibited *Pseudomonas putida*. Metab Eng.
64. Liu, X., and P. De Wulf. 2004. Probing the ArcA-P modulon of *Escherichia coli* by whole genome transcriptional analysis and sequence recognition profiling. J Biol Chem
65. Lu, J., R. C. Tappel, and C. T. Nomura. 2009. Mini-review: Biosynthesis of poly(hydroxyalkanoates). Polym Rev 49:226-248.
66. Luo, S., and A. N. Netravali. 2003. A study of physical and mechanical properties of poly(hydroxybutyrate-co-hydroxyvalerate) during composting. Polym Degrad Stab 80:59-66.
67. Matsumoto, K., A. Ishiyama, K. Sakai, T. Shiba, and S. Taguchi. 2011. Biosynthesis of glycolate-based polyesters containing medium-chain-length 3-hydroxyalkanoates in recombinant *Escherichia coli* expressing engineered polyhydroxyalkanoate synthase. J Biotechnol 156:214-217.
68. Matsumoto, K., T. Murata, R. Nagao, C. T. Nomura, S. Arai, Y. Arai, K. Takase, H. Nakashita, S. Taguchi, and H. Shimada. 2009. Production of short-chain-length/medium-chain-length polyhydroxyalkanoate (PHA) copolymer in the plastid of *Arabidopsis thaliana* using an engineered 3-ketoacyl-acyl carrier protein synthase III. Biomacromolecules 10:686-90.
69. Matsumoto, K., and S. Taguchi. 2010. Enzymatic and whole-cell synthesis of lactate-containing polyesters: toward the complete biological production of polylactate. Appl Environ Microbiol 85:921-932.
70. Mueller, A. P., and C. T. Nomura. 2012. Mutations to the active site of 3-ketoacyl-ACP synthase III (FabH) increase polyhydroxyalkanoate biosynthesis in transgenic *Escherichia coli*. J Biosci Bioeng 113:300-306.
71. Nikel, P. I., M. J. Pettinari, M. A. Galvagno, and B. S. Mendez. 2008. Poly(3-hydroxybutyrate) synthesis from glycerol by a recombinant *Escherichia coli* arcA mutant in fed-batch microaerobic cultures. Appl Microbiol Biotechnol: 1255-1257.
72. Nikel, P. I., M. J. Pettinari, M. A. Galvagno, and B. S. Méndez. 2006. Poly(3-hydroxybutyrate) synthesis by recombinant *Escherichia coli* arcA mutants in microaerobiosis. Appl Environ Microbiol 72:2614-2620.
73. Nizam, S. A., and K. Shimizu 2008. Effects of arcA and arcB knockout on the metabolism in *Escherichia coli* under anaerobic and microaerobic conditions. Biochem Eng J 42:229-236.
74. Noda, I., E. B. Bond, P. R. Green, D. H. Melik, K. Narasimhan, L. A. Schechtman, and M. M. Satkowski. 2003. Preparation, properties, and utilization of bio-based biodegradable Nodax™ PHA copolymers. Abstracts of Papers of the American Chemical Society 226:U396-U396.
75. Noda, I., P. R. Green, M. M. Satkowski, and L. A. Schechtman. 2005. Preparation and properties of a novel class of polyhydroxyalkanoate copolymers. Biomacromolecules 6:580-6.
76. Noda, I., M. M. Satkowski, A. E. Dowrey, and C. Marcott. 2004. Polymer alloys of Nodax copolymers and poly(lactic acid). Macromol Biosci 4:269-75.
77. Nomura, C. T., and Y. Doi. 2006. Metabolic engineering of recombinant *Escherichia coli* for short-chain-length-medium-chain-length polyhydroxyalkanoate biosynthesis. In K. Khemani and C. Scholz (ed.), Degradable Polymers and Materials-Principles and Practice. American Chemical Society, Washington, D.C.
78. Nomura, C. T., and B. R. Lundgren. 2012. Molecular roadblocks for RpoN binding sites.
79. Nomura, C. T., K. Taguchi, Z. Gan, K. Kuwabara, T. Tanaka, and Y. Doi. 2005. Expression of 3-ketoacyl-ACP reductase (fabG) enhances polyhydroxyalkanoate copolymer production from glucose in recombinant *Escherichia coli* JM109. Appl Environ Microbiol 71.
80. Nomura, C. T., K. Taguchi, S. Taguchi, and Y. Doi. 2004. Coexpression of genetically engineered 3-ketoacyl-ACP synthase III (fabH) and polyhydroxyalkanoate synthase (phaC) genes leads to short-chain-length-medium-chain-length polyhydroxyalkanoate copolymer production from glucose in *Escherichia coli* JM109. Appl Environ Microbiol 70:999-1007.
81. Nomura, C. T., T. Tanaka, T. E. Eguen, A. S. Appah, K. Matsumoto, S. Taguchi, C. L. Ortiz, and Y. Doi. 2008. FabG mediates polyhydroxyalkanoate production from both related and nonrelated carbon sources in recombinant *Escherichia coli* LS5218. Biotechnol Prog 24:342-51.
82. Nomura, C. T., T. Tanaka, Z. Gan, K. Kuwabara, H. Abe, K. Takase, K. Taguchi, and Y. Doi. 2004. Effective enhancement of short-chain-length (SCL)-medium-chain-length (MCL) polyhydroxyalkanoate copolymer production by co-expression of genetically engineered 3-ketoacyl-acyl-carrier protein synthase III (fabH) and polyhydroxyalkanoate synthesis genes. Biomacromolecules 5:1457-1464.
83. Examples 1 and 2
84. Pan, W., J. A. Perrotta, A. J. Stipanovic, C. T. Nomura, and J. P. Nakas. 2012. Production of polyhydroxyalkanoates by *Burkholderia cepacia* ATCC 17759 using a detoxified sugar maple hemicellulosic hydrolysate. J Ind Microbiol Biotechnol 39:459-469.
85. Park, S. J., and S. Y. Lee. 2003. Identification and characterization of a new enoyl coenzyme A hydratase involved in biosynthesis of medium-chain-length polyhydroxyalkanoates in recombinant *Escherichia coli*. J Bacteriol 185:5391-7.
86. Park, S. J., T. W. Lee, S. C. Lim, T. W. Kim, H. Lee, M. K. Kim, S. H. Lee, B. K. Song, and S. Y. Lee. 2012. Biosynthesis of polyhydroxyalkanoates containing 2-hydroxybutyrate from unrelated carbon source by metabolically engineered *Escherichia coli*. Appl Microbiol Biotechnol 93:273-283.
87. Park, S. J., and S. Yup Lee. 2004. New FadB homologous enzymes and their use in enhanced biosynthesis of medium-chain-length polyhydroxyalkanoates in FadB mutant *Escherichia coli*. Biotechnol Bioeng 86:681-6.
88. Patnaik, P. R. 2005. Perspectives in the modeling and optimization of PHB production by pure and mixed cultures. Crit Rev Biotechnol 25:153-171.
89. Pauli, G., and P. Overath. 1972. ato Operon: a highly inducible system for acetoacetate and butyrate degradation in *Escherichia coli*. Eur J Biochem 29:553-562.
90. Pietrini, M., L. Roes, M. K. Patel, and E. Chielini. 2007. Comparative life cycle studies on poly(3-hydroxybutyrate)-based composites as potential replacement for conventional petrochemical plastics. Biomacromolecules 8:2210-2218.
91. Rai, R., D. M. Yunos, A. R. Boccaccini, J. C. Knowles, I. A. Barker, S. M. Howdle, G. D. Tredwell, T. Keshavarz, and I. Roy. 2011. Poly-3-hydroxyoctanoate P(3HO), a medium chain length polyhydroxyalkanoate homopolymer from *Pseudomonas mendocina*. Biomacromolecules 12: pp 2126-2136.
92. Rehm, B. H., T. A. Mitsky, and A. Steinbuchel. 2001. Role of fatty acid de novo biosynthesis in polyhydroxyalkanoic acid (PHA) and rhamnolipid synthesis by pseudomonads: establishment of the transacylase (PhaG)-mediated pathway for PHA biosynthesis in *Escherichia coli*. Appl Environ Microbiol 67:3102-9.
93. Ren, Q., N. Sierro, B. Witholt, and B. Kessler. 2000. FabG, an NADPH-dependent 3-ketoacyl reductase of *Pseudomonas aeruginosa*, provides precursors for medium-chain-length poly-3-hydroxyalkanoate biosynthesis in *Escherichia coli*. J. Bacteriol 182:2978-2981.
94. Rhie, H. G., and D. Dennis. 1995. Role of fadR and atoC(Con) mutations in poly(3-hydroxybutyrate-co-3-hydroxyvalerate) synthesis in recombinant pha+ *Escherichia coli*. Appl Environ Microbiol 61:2487-92.
95. Rios, L. M., P. R. Jones, C. Moore, and U. V. Narayan. 2010. Quantitation of persistent organic pollutants adsorbed on plastic debris from the Northern Pacific Gyre's "eastern garbage patch". J Environ Monit 12:2226-2236.
96. Salis, H. M. 2011. The Ribosome Binding Site Calculator. Methods Enzymol 498:19-42.
97. Salis, H. M., E. A. Mirsky, and C. A. Voight. 2009. Automated design of synthetic ribosome binding sites to precisely control protein expression. Nat Biotechnol 27:946-950.
98. Sato, S., H. Kanazawa, and T. Tsuge. 2011. Expression and characterization of (R)-specific enoyl coenzyme A hydratases making a channeling route to polyhydroxyalkanoate biosynthesis in *Pseudomonas putida*. Appl Microbiol Biotechnol 90:951-9.
99. Schreck, K. M., and M. A. Hillmyer. 2007. Block copolymers and melt blends of polylactide with Nodax™ microbial polyesters: Preparation and mechanical properties. J Biotechnol 132:287-295.
100. Selmer, T., A. Willanzheimer, and M. Hetzel. 2002. Propionate CoA-transferase from *Clostridium propionicum*. Cloning of the gene and identification of glutamate 324 at the active site. Eur J Biochem 269:372-380.
101. Shi, J., N. M. Alves, and J. F. Mano. 2007. Thermally responsive biomineralization on biodegradable substrates. Adv Funct Mater 17:3312-3318.
102. Shozui, F., K. Matsumoto, R. Motohashi, M. Yamada, and S. Taguchi. 2010. Establishment of a metabolic pathway to introduce the 3-hydroxyhexanoate unit into LA-based polyesters via a reverse reaction of β-oxidation in *Escherichia coli* LS5218. Polym Degrad Stab 95:1340-1344.
103. Shozui, F., K. Matsumoto, T. Nakai, M. Yamada, and S. Taguchi. 2010. Biosynthesis of novel terpolymers poly (lactate-co-3-hydroxybutyrate-co-3-hydroxyvalerate) in lactate-overproducing mutant *Escherichia coli* JW0885 by feeding propionate as a precursor of 3-hydroxyvalerate. Appl Microbiol Biotechnol 85:949-954.
104. Sim, S. J., K. D. Snell, S. A. Hogan, J. Stubbe, C. Rha, and A. J. Sinskey. 1997. PHA synthase activity controls the molecular weight and polydispersity of polyhydroxybutyrate in vivo. Nat Biotechnol 15:63-67.
105. Slater, S. C., W. H. Voige, and D. E. Dennis. 1988. Cloning and expression in *Escherichia coli* of the *Alcaligenes eutrophus* H16 poly-beta-hydroxybutyrate biosynthetic pathway. J Bacteriol 170:4431-6.
106. Södergård, A., and M. Stolt. 2002. Properties of lactic acid based polymers and their correlation with composition. Prog Polym Sci 27:1123-1163.
107. Sparks, J., and C. Scholz. 2009. Evaluation of a cationic poly(beta-hydroxyalkanoate) as a plasmid DNA delivery system. Biomacromolecules 10:1715-1719.
108. Sparks, J., and C. Scholz. 2008. Synthesis and characterization of a cationic poly(beta-hydroxyalkanoate). Biomacromolecules 9:2091-2096.
109. Steinbüchel, A., and H. E. Valentin. 1995. Diversity of bacterial polyhydroxyalkanoic acids. FEMS Microbiol Lett 128:219-228.
110. Sudesh, K., H. Abe, and Y. Doi. 2000. Synthesis, structure and properties of polyhydroxyalkanoates: biological polyesters. Prog. Polym. Sci. 25:1503-1555.
111. Taguchi, K., Y. Aoyagi, H. Matsusaki, T. Fukui, and Y. Doi. 1999. Co-expression of 3-ketoacyl-ACP reductase and polyhydroxyalkanoate synthase genes induces PHA production in *Escherichia coli* HB101 strain. FEMS Microbiol Lett 176:183-90.
112. Taguchi, S., M. Yamada, K. Matsumoto, K. Tajima, Y. Satoh, M. Munekata, K. Ohno, K. Kohda, T. Shimamura, H. Kambe, and S. Obata. 2008. A microbial factory for lactate-based polyesters using a lactate-based polyesters using a lactate-polymerizing enzyme. Proc Natl Acad Sci USA 105:17323-17327.
113. Tajima, K., X. Han, Y. Satoh, A. Ishii, Y. Araki, M. Munekata, and S. Taguchi. 2012. In vitro synthesis of polyhydroxyalkanoate (PHA) incorporating lactate (LA) with a block sequence by using a newly engineered thermostable PHA synthase from *Pseudomonas* sp. SG4502 with acquired LA-polymerizing activity. Appl Microbiol Biotechnol 94:365-376.
114. Takase, K., S. Taguchi, and Y. Doi. 2003 Enhanced synthesis of poly(3-hydroxybutyrate) in recombinant *Escherichia coli* by means of error-prone PCR mutagenesis, saturation mutagenesis, and in vitro recombination of the type II polyhydroxyalkanoate synthase gene. J Biochem 133:139-145.
115. Example 2
116. Tappel, R. C., and C. T. Nomura. 2012. Recent Advances in Polyhydroxyalkanoate Biosynthesis in *Escherichia coli* In K. Khemani and C. Scholz (ed.), Degradable Polymers and Materials: Principles and Practice (2nd Edition). Oxford University Press, New York.
117. Example 1
118. Tsuge, K., K. Matsui, and M. Itaya. 2003. One step assembly of multiple DNA fragments with a designed order and orientation in *Bacillus subtilis* plasmid. Nucleic Acids Res 31:e133.
119. Tsuge, T., T. Fukui, H. Matsusaki, S. Taguchi, G. Kobayashi, A. Ishizaki, and Y. Doi. 2000. Molecular cloning of two (R)-specific enoyl-CoA hydratase genes from *Pseudomonas aeruginosa* and their use for polyhydroxyalkanoate synthesis. FEMS Microbiol Lett 184:193-8.
120. Tsuge, T., T. Hisano, S. Taguchi, and Y. Doi. 2003. Alteration of chain length substrate specificity of *Aeromonas caviae* R-enantiomer-specific enoyl-coenzyme A hydratase through site-directed mutagenesis. Appl Environ Microbiol 69:4830-6.
121. Tsuge, T., K. Taguchi, T. Seiichi, and Y. Doi. 2003. Molecular characterization and properties of (R)-specific enoyl-CoA hydratases from *Pseudomonas aeruginosa*: metabolic tools for synthesis of polyhydroxyalkanoates via fatty acid beta-oxidation. Int J Biol Macromol 31:195-205.
122. Tsuji, H. 2005. Poly(lactide) stereocomplexes: formation, structure, properties, degradation, and applications. Macomol Biosci 5.
123. Tsuji, H., K. Suzuyoshi, Y. Tezuka, and T. Ishida. 2003. Environmental degradation of biodegradable polyesters: 3. Effects of alkali treatment on biodegradation of poly (e-caprolactone) and poly[(R)-3-hydroxybutyrate) films in controled soil. J Polym Environ 11:57-65.
124. U. S. Department of Energy, E. I. A. 2009. How much oil is used to make plastic? In U. E. I. Administration (ed.).
125. U. S. Environmental Protection Agency, O. o. R. C. a. R. 2009. Municipal Solid Waste Generation, Recycling, and Disposal in the United States Detailed Tables and Figures for 2008. Report.
126. Wang, F., and S. Y. Lee. 1997. Production of poly(3-hydroxybutyrate) by fed-batch culture of filamentation-suppressed recombinant *Escherichia coli*. Appl Environ Microbiol 63:4765-4769.
127. Wang, H. H., X. R. Li, Q. Liu, and G. Q. Chen. 2011. Biosynthesis of polyhydroxyalkanoate homopolymers by *Pseudomonas putida*. Appl Microbiol Biotechnol 89:1497-1507.
128. Wang, H. H., X. T. Li, and G. Q. Chen. 2009. Production and characterization of homopolymer polyhydroxyheptanoate (P3HHp) by a fadBA knockout mutant *Pseudomonas putida* KTOY06 derived from *P. putida* KT2442. Process Biochem 44:106-111.
129. Wang, Q., A. P. Mueller, C. R. Leong, K. Matsumoto, K. Taguchi, and C. T. Nomura. 2010. Quick and efficient method for genetic transformation of biopolymer-producing bacteria. J Chem Technol Biotechnol 85:775-778.
130. Wang, Q., and C. T. Nomura. 2010. A survey of biodegradable plastics in the U.S. BioPla 36:18-23.
131. Wang, Q., and C. T. Nomura. 2010. Monitoring differences in gene expression levels and polyhydroxyalkanoate (PHA) production in *Pseudomonas putida* KT2440 grown on different carbon sources. J Biosci Bioeng 110: 653-659.
132. Wang, Q., R. C. Tappel, C. Zhu, and C. T. Nomura. 2012. Development of a new strategy for production of medium-chain-length polyhydroxyalkanoates (MCL-PHAs) from inexpensive non-fatty acid feedstocks in recombinant *Escherichia coli*. Appl Environ Microbiol 78:519-527.
133. Wang, Q., C. Zhu, T. J. Yancone, and C. T. Nomura. 2012. The effect of co-substrate feeding on polyhydroxyalkanoate (PHA) homopolymer and copolymer production in recombinant *Escherichia coli* LS5218. J Bioprocess Eng Biorefinery 1:1-7.
134. Yamada, M., K. Matsumoto, T. Nakai, and S. Taguchi. 2009. Microbial production of lactate-enriched poly[(R)-lactate-co-(R)-3-hydoxybutyrate] with novel thermal properties. Biomacromolecules 10:677-681.
135. Yamada, M., K. Matsumoto, K. Shimizu, S. Uramoto, T. Nakai, F. Shozui, and S. Taguchi. 2010. Adjustable mutations in lactate (LA)-polymerizing enzyme for the microbial production of LA-based polyesters with tailormade monomer composition. Biomacromolecules 11:815-9.
136. Yamada, M., K. Matsumoto, S. Uramoto, R. Motohashi, H. Abe, and S. Taguchi. 2011. Lactate fraction dependent mechanical properties of semitransparent poly (lactate-co-3-hydroxybutyrate)s produced by control of lactyl-CoA monomer fluxes in recombinant *Escherichia coli*. J Biotechnol 154:255-260.
137. Yang, T. H., Y. K. Jung, H. O. Kang, T. W. Kim, S. J. Park, and S. Y. Lee. 2011. Tailor-made type II *Pseudomonas* PHA synthases and their use for the biosynthesis of polylactic acid and its copolymer in recombinant *Escherichia coli*. Appl Microbiol Biotechnol 90:603-614.
138. Yang, T. H., T. W. Kim, H. O. Kang, S. H. Lee, E. J. Lee, S. C. Lim, S. O. Oh, A. J. Song, S. J. Park, and S. Y. Lee. 2010. Biosynthesis of polylactic acid and its copolymers using evolved propionate CoA transferase and PHA synthase. Biotechnol Bioeng 105:150-160.
139. Youn, H., R. L. Kerby, M. Conrad, and G. P. Roberts. 2006. Study of highly constitutively active mutants suggests how cAMP activates cAMP receptor protein. J Biol Chem 281:1119-1127.
140. Zhou, L., Z. R. Zuo, X. Z. Chen, D. D. Niu, K. M. Tian, B. A. Prior, W. Shen, G. Y. Shi, S. Singh, and Z. X. Wang. 2011. Evaluation of Genetic Manipulation Strategies on D-Lactate Production by *Escherichia coli*. Curr Microbiol 62:981-989.

141. Zhu, C., C. T. Nomura, J. A. Perrotta, A. J. Stipanovic, and J. P. Nakas. 2010. Production and characterization of poly-3-hydroxybutyrate from biodiesel-glycerol by *Burkholderia cepacia* ATCC 17759. Biotechnol Prog 26:424-30.
142. Zhu, C., C. T. Nomura, J. A. Perrotta, A. J. Stipanovic, and J. P. Nakas. 2012. The effect of nucleating agents on physical properties of poly-3-hydroxybutyrate (PHB) and poly-3-hydroxybutyrate-co-3-hydroxyvalerate (PHB-co-HV) produced by *Burkholderia cepacia* ATCC 17759. Polym Testing 31:579-585.
143. Zinn, M., B. Witholt, and T. Egli. 2001. Occurrence, synthesis and medical application of bacterial polyhydroxyalkanoate. Adv Drug Deliv Rev 53:5-21.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

While embodiments of the present disclosure have been particularly shown and described with reference to certain examples and features, it will be understood by one skilled in the art that various changes in detail may be effected therein without departing from the spirit and scope of the present disclosure as defined by claims that can be supported by the written description and drawings. Further, where exemplary embodiments are described with reference to a certain number of elements it will be understood that the exemplary embodiments can be practiced utilizing either less than or more than the certain number of elements.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A recombinant bacterium for producing a prescribed unit size of a poly(3-hydroxyalkanoate) (PHA) polymer, wherein the bacterium:
   metabolizes a short to long chain fatty acid substrate without induction,
   deletes the gene for the (S)-specific enoyl-CoA hydratase (fadB) and the gene fadJ (also known as yfcX) which is involved in the β-oxidation pathway;
   expresses an (R)-specific enoyl-CoA hydratase and a PHA synthase, and
   produces exclusively a prescribed unit size PHA polymer from a fatty acid substrate, the fatty acid substrate being of equal carbon length to the prescribed unit size of the PHA polymer to be produced.

2. The recombinant bacterium of claim 1, wherein the bacterium is not a native or natural producer of PHA or lacks enzymes to degrade PHA once synthesized.

3. The recombinant bacterium of claim 1, wherein the recombinant bacterium is a recombinant *E. coli*.

4. The recombinant bacterium of claim 1, wherein the bacterium comprises a plasmid comprising an (R)-specific enoyl-CoA hydratase gene and a PHA synthase gene.

5. The recombinant bacterium of claim 1, wherein β-oxidation is blocked in the recombinant bacterium.

6. The recombinant bacterium of claim 1, wherein at least one gene encoding an enzyme for β-oxidation is inactive or deleted from the chromosome of the recombinant bacterium.

7. The recombinant bacterium of claim 1, wherein the recombinant bacterium constitutively expresses a positive regulator of an operon, wherein the operon promotes uptake of short chain fatty acids for β-oxidation.

8. The recombinant bacterium of claim 3, wherein the recombinant *E. coli* constitutively expresses AtoC.

9. The recombinant bacterium of claim 1, wherein the recombinant bacterium expresses propionyl-CoA transferase (PCT).

10. The recombinant bacterium of claim 1, wherein the recombinant bacterium has gene deletions for a negative transcriptional regulator of the β-oxidation pathway.

* * * * *